(12) United States Patent
Main et al.

(10) Patent No.: US 12,357,239 B2
(45) Date of Patent: Jul. 15, 2025

(54) INTELLIGENT PATIENT MONITORING SYSTEM

(71) Applicant: XSENSOR Technology Corporation, Calgary (CA)

(72) Inventors: Ian Main, Calgary (CA); Mohammad Najafi, Calgary (CA); Mitchell Robert Knight, Calgary (CA); Adele Syt Fu Chui, Calgary (CA); Dylan Heckbert, Calgary (CA); Murray Ross Vince, Seattle, WA (US); Bruce Malkinson, Calgary (CA); Tim Gorjanc, Calgary (CA)

(73) Assignee: XSENSOR Technology Corporation, Calgary (CA)

( * ) Notice: Subject to any disclaimer, the term of this patent is extended or adjusted under 35 U.S.C. 154(b) by 19 days.

(21) Appl. No.: 17/339,401

(22) Filed: Jun. 4, 2021

(65) Prior Publication Data
US 2022/0087617 A1     Mar. 24, 2022

Related U.S. Application Data

(60) Provisional application No. 63/170,091, filed on Apr. 2, 2021, provisional application No. 63/080,271, filed on Sep. 18, 2020.

(51) Int. Cl.
*A61B 5/00* (2006.01)
*A61B 5/11* (2006.01)
*G16H 50/20* (2018.01)

(52) U.S. Cl.
CPC .......... *A61B 5/7275* (2013.01); *A61B 5/1117* (2013.01); *A61B 5/447* (2013.01);
(Continued)

(58) Field of Classification Search
CPC ................ A61B 5/6892; A61B 5/6894; A61B 2562/0247; A61B 2562/0271;
(Continued)

(56) References Cited

U.S. PATENT DOCUMENTS

| 2,378,039 A | 6/1945 | Schenker |
| 2,804,129 A | 8/1957 | Propst |

(Continued)

FOREIGN PATENT DOCUMENTS

| AU | 48619/93 | 5/1994 |
| AU | 649391 B3 | 5/1994 |

(Continued)

OTHER PUBLICATIONS

Bates-Jensen, et.al., "Subepidermal moisture detection of pressure induced tissue damage on the trunk: The pressure ulcer detection study outcomes," Wound Repair and Regeneration, 2017. https://doi.org/10.1111/wrr.1254.8. (Year: 2017).*

(Continued)

*Primary Examiner* — Aurelie H Tu
(74) *Attorney, Agent, or Firm* — Fenwick & West LLP

(57) ABSTRACT

Embodiments may relate to an intelligent patient monitoring system, which may include a weight support device, a computer, and a display. The weight support device supports a patient and includes a sensor grid layer with a plurality of sensors to measure pressure data. The computer predicts a pressure injury outcome and/or a fall outcome based on the pressure data. The pressure injury outcome includes a prediction of risk of the patient developing a pressure injury. The fall outcome includes a prediction of risk of the patient experiencing a fall. The computer may utilize a machine learning model to determine either or both outcomes. The display presents a notification generated based on the pressure injury outcome or fall outcome. The notification indi- (Continued)

cates that an adjustment of a positioning of the patient is needed to aid in the prevention of the pressure injury or the fall.

18 Claims, 28 Drawing Sheets

(52) U.S. Cl.
CPC .......... *A61B 5/6892* (2013.01); *A61B 5/6894* (2013.01); *A61B 5/7267* (2013.01); *G16H 50/20* (2018.01); *A61B 2562/0247* (2013.01); *A61B 2562/0271* (2013.01); *A61B 2562/029* (2013.01); *A61B 2562/066* (2013.01)

(58) Field of Classification Search
CPC . A61B 2562/029; A61B 5/447; A61B 5/7275; A61B 5/1117; A61B 5/7267; A61B 2562/066; A61B 5/015; A61B 5/1122; A61B 2505/07; A61B 2562/046; A61B 5/02055; G16H 50/20; G16H 40/67; G16H 50/30

See application file for complete search history.

(56) References Cited

U.S. PATENT DOCUMENTS

| | | | |
|---|---|---|---|
| 2,976,725 A | 3/1961 | Byer |
| 3,100,992 A | 8/1963 | Davis |
| 3,195,347 A | 7/1965 | Janapol |
| 3,334,517 A | 8/1967 | Janapol |
| 3,413,849 A | 12/1968 | Janapol |
| 3,565,195 A | 2/1971 | Miller et al. |
| 3,826,926 A | 7/1974 | White et al. |
| 3,875,481 A | 4/1975 | Miller et al. |
| 4,005,438 A | 1/1977 | Meltzer et al. |
| 4,134,063 A | 1/1979 | Nicol et al. |
| 4,266,263 A | 5/1981 | Haberl et al. |
| 4,370,697 A | 1/1983 | Haberl et al. |
| 4,554,930 A | 11/1985 | Kress |
| 4,584,625 A | 4/1986 | Kellogg |
| 4,662,012 A | 5/1987 | Torbet |
| 4,827,763 A | 5/1989 | Bourland et al. |
| 4,986,136 A | 1/1991 | Brunner et al. |
| 5,010,772 A | 4/1991 | Bourland et al. |
| 5,148,706 A | 9/1992 | Masuda et al. |
| 5,231,717 A | 8/1993 | Scott et al. |
| 5,306,912 A | 4/1994 | Sibbald et al. |
| 5,401,922 A | 3/1995 | Asta |
| 5,447,076 A | 9/1995 | Ziegler |
| 5,487,196 A | 1/1996 | Wilkinson et al. |
| 5,514,832 A | 5/1996 | Dusablon et al. |
| 5,653,939 A | 8/1997 | Hollis et al. |
| 5,693,886 A | 12/1997 | Seimiya et al. |
| 5,745,940 A | 5/1998 | Roberts et al. |
| 5,815,865 A | 10/1998 | Washburn et al. |
| 5,848,450 A | 12/1998 | Oexman et al. |
| 5,963,997 A | 10/1999 | Hagopian |
| 5,970,789 A | 10/1999 | Meyer et al. |
| 5,993,400 A | 11/1999 | Rincoe et al. |
| 6,192,538 B1 | 2/2001 | Fogel |
| 6,280,392 B1 | 8/2001 | Yoshimi et al. |
| 6,585,328 B1 | 7/2003 | Oexman et al. |
| 6,826,968 B2 | 12/2004 | Manaresi et al. |
| 7,067,979 B2 | 6/2006 | Sakamoto |
| 7,107,642 B2 | 9/2006 | Wong et al. |
| 7,378,975 B1 | 5/2008 | Smith et al. |
| 7,467,058 B2 | 12/2008 | Boyd |
| 7,580,030 B2 | 8/2009 | Marten |
| 7,609,178 B2 | 10/2009 | Son et al. |
| 7,638,350 B2 | 12/2009 | Deconde et al. |
| 7,937,239 B2 | 5/2011 | Boyd |
| 8,011,041 B2 | 9/2011 | Hann |
| 8,121,800 B2 | 2/2012 | Altman et al. |
| 8,272,276 B2 | 9/2012 | Gorjanc et al. |
| 8,458,042 B1 | 6/2013 | Roberts et al. |
| 8,463,006 B2 | 6/2013 | Prokoski |
| 8,544,336 B2 | 10/2013 | Main et al. |
| 8,893,561 B2 | 11/2014 | Gorjanc et al. |
| 9,186,479 B1 | 11/2015 | Franceschetti et al. |
| 9,320,665 B2 | 4/2016 | Main et al. |
| 9,659,322 B2 | 5/2017 | Gorjanc et al. |
| 9,848,712 B2 | 12/2017 | Main et al. |
| 9,860,982 B1 | 1/2018 | Main et al. |
| 10,314,407 B1 | 6/2019 | Main et al. |
| 10,562,412 B1 | 2/2020 | Main et al. |
| 10,729,876 B2 | 8/2020 | Main et al. |
| 10,973,344 B2 | 4/2021 | Poodeh et al. |
| 2002/0155728 A1 | 10/2002 | Khandros et al. |
| 2002/0184711 A1 | 12/2002 | Mahoney et al. |
| 2003/0121101 A1 | 7/2003 | Corzani et al. |
| 2004/0133092 A1 | 7/2004 | Kain |
| 2005/0012219 A1 | 1/2005 | Liou |
| 2005/0165284 A1 | 7/2005 | Gefen |
| 2005/0173144 A1 | 8/2005 | Federighi et al. |
| 2005/0241409 A1 | 11/2005 | Taylor |
| 2007/0069642 A1 | 3/2007 | Kitai et al. |
| 2007/0257821 A1 | 11/2007 | Son et al. |
| 2008/0052837 A1 | 3/2008 | Blumberg |
| 2008/0062176 A1 | 3/2008 | Arya |
| 2008/0180390 A1 | 7/2008 | Yoshikawa |
| 2008/0201856 A1 | 8/2008 | Howard |
| 2008/0275349 A1 | 11/2008 | Halperin et al. |
| 2009/0062693 A1 | 3/2009 | Woolfson et al. |
| 2009/0070939 A1 | 3/2009 | Hann |
| 2009/0093717 A1 | 4/2009 | Carneiro et al. |
| 2009/0209830 A1 | 8/2009 | Nagle et al. |
| 2009/0216466 A1 | 8/2009 | Altman et al. |
| 2009/0240514 A1 | 9/2009 | Oexman et al. |
| 2010/0022850 A1 | 1/2010 | McKenna et al. |
| 2010/0174198 A1 | 7/2010 | Young et al. |
| 2010/0191541 A1 | 7/2010 | Prokoski |
| 2010/0317930 A1 | 12/2010 | Oexman et al. |
| 2010/0318239 A1 | 12/2010 | Oexman et al. |
| 2011/0010014 A1 | 1/2011 | Oexman et al. |
| 2011/0112442 A1 | 5/2011 | Meger et al. |
| 2011/0245732 A1 | 10/2011 | Mravyan et al. |
| 2011/0308019 A1 | 12/2011 | Terawaki et al. |
| 2012/0296156 A1 | 11/2012 | Auphan |
| 2012/0311790 A1 | 12/2012 | Nomura et al. |
| 2013/0000047 A1 | 1/2013 | McCann et al. |
| 2013/0006151 A1 | 1/2013 | Main et al. |
| 2013/0090571 A1* | 4/2013 | Nourani ................ G16H 20/30 |
| | | | 600/587 |
| 2013/0144751 A1 | 6/2013 | Gorjanc et al. |
| 2013/0283530 A1 | 10/2013 | Main et al. |
| 2014/0343889 A1 | 11/2014 | Ben Shalom et al. |
| 2014/0366277 A1 | 12/2014 | Niederkrom et al. |
| 2015/0320352 A1 | 11/2015 | Ben Shalom et al. |
| 2015/0371522 A1* | 12/2015 | Mravyan ................ H04W 4/80 |
| | | | 340/573.1 |
| 2017/0281073 A1 | 10/2017 | Drennan et al. |
| 2018/0027988 A1 | 2/2018 | Poodeh et al. |
| 2018/0064402 A1 | 3/2018 | Leydon |
| 2019/0026957 A1 | 1/2019 | Gausebeck |
| 2020/0155059 A1* | 5/2020 | Kayser ................ A61B 5/6891 |
| 2020/0405217 A1* | 12/2020 | Jayaraman ............ A61B 5/746 |
| 2021/0196055 A1 | 7/2021 | Poodeh et al. |
| 2022/0142834 A1* | 5/2022 | Hamilton ............. G08B 21/182 |

FOREIGN PATENT DOCUMENTS

| | | |
|---|---|---|
| CN | 101803983 A | 8/2010 |
| EP | 2182339 A1 | 5/2010 |
| FR | 2720622 A1 | 12/1995 |
| JP | H04-325116 | 11/1992 |
| JP | 2009-119082 A | 6/2009 |
| WO | WO 01/00089 A1 | 1/2001 |
| WO | WO 2009/102361 A1 | 8/2009 |
| WO | WO 2010/045741 A1 | 4/2010 |
| WO | WO 2011/066151 A1 | 6/2011 |
| WO | WO 2011/091517 A1 | 8/2011 |

(56) References Cited

FOREIGN PATENT DOCUMENTS

| | | |
|---|---|---|
| WO | WO 2012/160502 A1 | 11/2012 |
| WO | WO 2013/085785 A1 | 6/2013 |
| WO | WO 2014/145436 A1 | 9/2014 |

OTHER PUBLICATIONS

A Good Mattress is a Dream Come True, New York Times News Service, Mar. 29, 1998, 1 page, available at http://articles.chicagotribune.com/1998-03-29/news/9803290437.sub.--1.sub-.--mattress-sleep-wake-disorder-center-bed.

Amazon.com, "Honeywell Home RCHW3610WF1006/N Water Leak Detector," Apr. 20, 2018, nine pages, [Online] [Retrieved on Aug. 31, 2021] Retrieved from the Internet <URL: https://www.amazon.ca/Honeywell-RCHW3610WF1006-Water-Leak-Detector/dp/B07CJG91DM/ref=asc_df_B07CJG91DM/?tag=googleshopc0c-20&linkCode=df0&hvadid=292938317460&hvpos=&hvnetw=g&hvrand=9101712106439063987&hvpone=&hvptwo=&hvqmt=&hvdev=c&hvdvcmdl=&hvlocint=&hvlocphy=9001314&hvtargid=pla-554077522699&psc=1>.

Barhyte, et al., Selection of a Standard Hospital Mattress: Data-Based Decision Making, vol. 22, No. 6 Journal of Wound Ostomy & Continence Nursing, Nov. 1995, pp. 267-270, vol. 22, No. 6.

Bayer L., et al., "Rocking synchronizes brain waves during a short nap," Current Biology, 2011, pp. R461-R462, vol. 21, No. 12.

Brienza, et al., A Method for Custom-Contoured Cushion Design Using Interface Pressure Measurements, IEEE Transactions on Rehabilitation Engineering, Mar. 1999, pp. 99-108, vol. 7, No. 1.

Brienza, et al., Seat Cushion Optimization: a Comparison of Interface Pressure and Tissue Stiffness Characteristics for Spinal Cord Injured and Elderly Patients, vol. 79, Archives of Physical Medicine & Rehabilitation, Apr. 1998, pp. 388-394, vol. 79.

Chiradejnant, A., The Study of the Reliability and Validity of the Ergocheck Measurement System, School of Physiotherapy, University of South Australia, 1998. 74 pages.

Clark, M., "Comparison of the Pressure Redistributing Attributes of a Selection of Bed Mattresses Used to Prevent Pressure Sores," The Journal of Tissue Viability, Jul. 1991, pp. 65-67, vol. 1 No. 3.

Cork, Russel, "Xsensor technology: A pressure imaging overview", Published in Sensor Review on 27.1 (2007): 24.; extracted for PQ dialog search on May 11, 2015.

Defloor, T. et al., "Sitting Posture and Prevention of Pressure Ulcers," Applied Nursing Research, Aug. 1999, pp. 137-142, vol. 12 No. 3.

Digi-Key, "Water Contact Indicator Tape," Date Unknown, three pages, [Online] [Retrieved on Aug. 31, 2021] Retrieved from the Internet <URL: https://www.digikey.ca/en/product-highlight/3/3m-tc/water-contact-indicator-tape>.

Ergocheck Brochure: Ergocheck Fulfils One of the Essential Demands of the Bedding Trade, ABW, 1994, 3 pages.

Ergocheck Measuring System, 1994 Ergocheck v.2.0 Reference Manual, 105 pages.

"Force Sensing Array Version 3.1 User Manual," 2 ed., Vista Medical Ltd., 1996, 66 pages.

Fronczek, R., et al., "Manipulation of Core Body and Skin Temperature Improves Vigilance and Maintenance of Wakefulness in Narcolepsy," Sleep, 2008, pp. 233-240, vol. 31, No. 2.

Gignac, Tamara; "Xsensor's body maps guide manufacturers: Pressure-point technology has manyapplications"; [Final Edition] Publication info: Calgary Herald [Calgary, Alta] Mar. 13, 2006: B8.

Harstall, C., "Interface Pressure Measurement Systems for Management of Pressure Sores," Alberta Heritage Foundation for Medical Research, Sep. 1996, 21 pages.

Kreutz, D., Computerized Pressure Mapping, Advance for Directors in Rehabilitation, Nov. 11-12, 1997, 3 pages.

Krouskop, T.A. et al., "Factors Affecting the Pressure-Distributing Properties of Foam Mattress Overlays," Journal of Rehabilitation Research and Development, Jul. 1986, pp. 33-39, vol. 23, No. 3.

Lipka, D., "An Overview of Pressure-Mapping System," Technology Special Interest Section Quarterly, Dec. 1997, pp. 1-6, vol. 7 No. 4.

Machiel Van Der Loos, H.F. et al., "Development of Sensate and Robotic Bed Technologies for Vital Signs Monitoring and Sleep Quality Improvement," Autonomous Robots, 2003, pp. 67-79, vol. 15.

Malacaria, C., A Thin, Flexible, Matrix-Based Pressure Sensor, Sensors Magazine, Sep. 1998, 5 pages.

Malakuti, K., "Towards an Intelligent Bed Sensor: Non-Intrusive Monitoring of Sleep Disturbances via Computer Vision Techniques," Thesis, University of Victoria, 2008, 93 pages.

Nicol, K. et al., "Pressure Distribution on Mattresses," Journal of Biomechanics, 1993, pp. 1479-1486, vol. 26, No. 12.

Oxford Pressure Monitor, Operating Instructions (received by the Food and Drug Administration on Dec. 9, 1991), 32 pages.

Park, S.J. et al., "Measurement and Analysis of Pressure Distribution on the Bed," Proceedings of the Human Factors and Ergonomics Society 39.sup.th Annual Meeting, 1995, pp. 297-300.

Raymann, R., et al., "Skin deep: enhanced sleep depth by cutaneous temperature manipulation," Brain, 2008, pp. 500-513, vol. 131.

Reswick, J.B. et al., Experience at Rancho Los Amigos Hospital with Devices and Techniques to Prevent Pressure Sores, in Bedsore Biomechanics 301, 307-08 (University Park Press 1976).

Reynolds, A. et al., Pressure-Reducing Capability of Conforma II Mattress Overlay, Advances in Wound Care, Jul. 1994, pp. 36-40, vol. 7, No. 4.

Rithalia, S. V.S. et al., "Assessment of Alternating Air Mattresses Using a Time-Based Interface Pressure Threshold Technique," Journal of Rehabilitation Research and Development, Jun. 1998, pp. 225-230, vol. 35 No. 2.

Shelton, et al., Full-Body Interface Pressure Testing as a Method for Performance Evaluation of Clinical Support Surfaces, Applied Ergonomics, 1998, pp. 491-497, vol. 29, No. 6.

SparkFun, "SparkFun Soil Moisture Sensor," Date Unknown, nine pages, [Online] [Retrieved on Aug. 31, 2021] Retrieved from the Internet <URL: https://www.sparkfun.com/products/13322>.

Talley Pressure Monitor 3, Operating Manual 1st Ed. Preliminary (received by the Food and Drug Administration on Dec. 9, 1991), 44 pages.

Telefax from A. Ahrens to L. Larson, Mar. 14, 1995, 1 page.

The Canadian Patient Safety Institute, "Never Events for Hospital Care in Canada," Sep. 2015, 11 pages, [Online] [Retrieved on Aug. 31, 2021] Retrieved from the Internet <URL: https://www.patientsafetyinstitute.ca/en/toolsResources/NeverEvents/Documents/Never Events for Hospital Care in Canada.pdf>.

U.S. Appl. No. 17/019,090, filed Sep. 11, 2020, Inventors: Ian Main, Mohammad Najafi, Mitchell Rovert Knight, Adele Syt Fu Chui, Dylan Heckbert, Murray Ross Vince.

Yousefi, R. et al., "A Smart Bed Platform for Monitoring & Ulcer Prevention," 2011 4.sup.th International Conference on Biomedical Engineering and Informatics (BMEI), IEEE, 2011, pp. 1362-1366.

Yousefi, R. et al., "Bed Posture Classification for Pressure Ulcer Prevention," 2011 Annual International Conference of the IEEE, Engineering in Medicine and Biology Society, EMBC, Aug. 30, 2011-Sep. 3, 2011, pp. 7175-7178.

Zabel, M., "Buying Mattresses for Comfort," University of Minnesota, 1969, 15 pages.

PCT International Search Report and Written Opinion, PCT Application No. PCT/IB2021/000598, Feb. 18, 2022, 14 pages.

PCT Invitation to Pay Additional Fees, PCT Application No. PCT/IB2021/000598, Jan. 5, 2022, two pages.

United States Office Action, U.S. Appl. No. 17/019,090, filed Feb. 3, 2023, 10 pages.

\* cited by examiner

INTELLIGENT PATIENT MONITORING SYSTEM

CROSS-REFERENCE TO RELATED APPLICATIONS

This application claims the benefit of U.S. Provisional Patent Application No. 63/080,271, filed Sep. 18, 2020, and U.S. Provisional Patent Application No. 63/170,091, filed Apr. 2, 2021, both of which are incorporated by reference in their entirety.

TECHNICAL FIELD

The present disclosure generally relates to a weight support device, in particular to a weight support device that includes a sensor grid that can detect pressure data of a person.

BACKGROUND

Pressure injuries (e.g., bedsores, pressure ulcers, pressure sores, or decubitus ulcers) are a common problem in clinical or at-home settings. Oftentimes, the presence of a pressure injury in a patient may lead to an increase in time spent at a hospital, an increase in medical costs (e.g., Medicare no longer covers the cost of hospital-acquired pressure ulcers), and/or permanent damage suffered by the patient. There are four stages of pressure injury: Stage I—The skin is a slightly different color, but there are no open wounds, Stage II—The skin breaks open and an ulcer forms, Stage III—The sore becomes worse and creates a crater in the tissue, and Stage IV—The sore is very deep causing extensive damage and can harm muscle, bone and tendons. Stage III and IV ulcers can lead to serious complications such as infections of the bone or blood (sepsis). Depending on the healthcare region, these injuries are considered 'never events', which are patient safety incidents that result in serious patient harm or death, and that can be prevented by using organizational checks and balances.

A typical prevention strategy to avoid pressure injury in a patient is a turn regimen where a healthcare professional or other caregiver re-positions the patient periodically to relieve localized pressure before the patient's skin integrity is breached and a wound begins to form. Unfortunately, currently-used turn regimens are not personalized to each patient or optimized for efficiency of the healthcare professional's time.

Additionally, injuries caused by a fall are common problems in clinical or at-home settings. For example, decreasing an amount of injuries caused by a fall from a wheelchair or from a bed is desirable in many patient settings. One patient setting where detecting a fall would provide an important service is in settings where high-risk populations like seniors are treated. Seniors and other high-risk populations are more prone to injury and extended periods of healing after a fall, thus detecting when a patient is about to fall and preventing the fall is important in reducing amount of time spent at a hospital for the patient, a decrease in medical costs, and/or prevention of any injury due to fall for those patients.

SUMMARY

Embodiments disclosed relate to a continuous patient monitoring solution that is proactive with patient positioning, prevention of pressure injury, and/or prevention of fall. With a continuous collection of patient data and a high-resolution visualization of areas of high pressure, the patient monitoring solution helps clinicians improve patient safety. Patient data includes at least pressure data with position tracking and machine learning model(s) that individualize care for the patient. This solution uses AI-powered algorithms that inform advanced prevention strategies. The prevention strategies can maintain healthy skin for patients and/or prevent injuries caused by a fall. In some embodiments, clinicians and patients are provided visual, easy-to-understand pressure images that identify areas that are experiencing elevated pressures so that body position adjustments can be made efficiently and effectively.

The disclosed system may include a fitted mattress cover overlay or a fully-integrated mattress solution. Both options are embedded with a network of sensors (e.g., thousands of sensors) that continuously measure the patient's body surface pressures. A touch screen monitor displays visual representations of pressures with markers that clearly identify areas of the body (e.g., areas experiencing sustained pressure). A patient turn clock can track the time since a last position adjustment, visually notifying the clinician that it's time to adjust the patient's body position. The recent turns and pressure exposure screen can allow caregivers to see at a glance the turn or movement history of the patient.

With highly accurate and affordable skin and pressure sensors available, corresponding sensor data is fast becoming big data. Analytics and artificial intelligence can convert patient big data into patient smart data by distilling big data and providing actionable, empirically-based guidance to improve patient outcomes. Where automation and medical devices can be applied to the process, smart data for machine learning will continually refine and improve patient outcomes in terms of quality, cost, efficiency, time, and improved patient outcomes. The disclosed system may include advanced intelligent dynamic pressure sensors collecting sensor data and a database of patient health data (age, weight, height, gender, etc.) with AI models that takes big data from the patient and turns it into smart actionable data. The smart actional data is concise and can be provided in a simple manner for healthcare professionals to know when and how to adjust the positioning of the patient to alleviate pressure on the skin and/or to prevent a fall.

Embodiments may relate to a pressure injury prevention system for a patient, which may include a weight support device, a computer, and a display. The weight support device supports the patient and comprises a sensor grid layer. The sensor grid layer includes a plurality of sensors configured to measure pressure data. The computer predicts a pressure injury outcome based on the pressure data. The pressure injury outcome includes at least a prediction of risk of the patient developing a pressure injury. The display presents a notification generated based on the pressure injury outcome. The notification indicating that an adjustment of a positioning of the patient is needed.

Embodiments may also relate to a method for determining a risk of a patient developing a pressure injury. The method may include receiving pressure data from a weight support device that comprises a sensor grid. The sensor grid includes a plurality of sensors that generates the pressure data. The method may also include predicting, based on the pressure data, a pressure injury outcome of the patient supported by the weight support device. The pressure injury outcome includes at least a prediction of the risk of the patient developing the pressure injury. The method may further include providing, for display, a notification generated based on the pressure injury outcome. The notification indicating that an adjustment of a positioning of the patient is needed.

Embodiments may relate to a fall prevention system for a patient, which may include a weight support device, a computer, and a display. The weight support device supports the patient and comprises a sensor grid layer. The sensor grid layer includes a plurality of sensors configured to measure pressure data. The computer predicts a fall outcome based on the pressure data. The fall outcome includes at least a prediction of risk of the patient falling off of the weight support device. The display presents a notification generated based on the fall outcome. The notification indicating that an adjustment of a positioning of the patient is needed.

Embodiments may also relate to a method for determining a risk of a patient experiencing a fall. The method may include receiving pressure data from a weight support device that comprises a sensor grid. The sensor grid includes a plurality of sensors that generates the pressure data. The method may also include predicting, based on the pressure data, a fall outcome of the patient supported by the weight support device. The fall outcome including at least a prediction of the risk of the patient falling off of the weight support device. The method may further include providing, for display, a notification generated based on the fall outcome. The notification indicating that an adjustment of a positioning of the patient is needed.

Figure 1A:
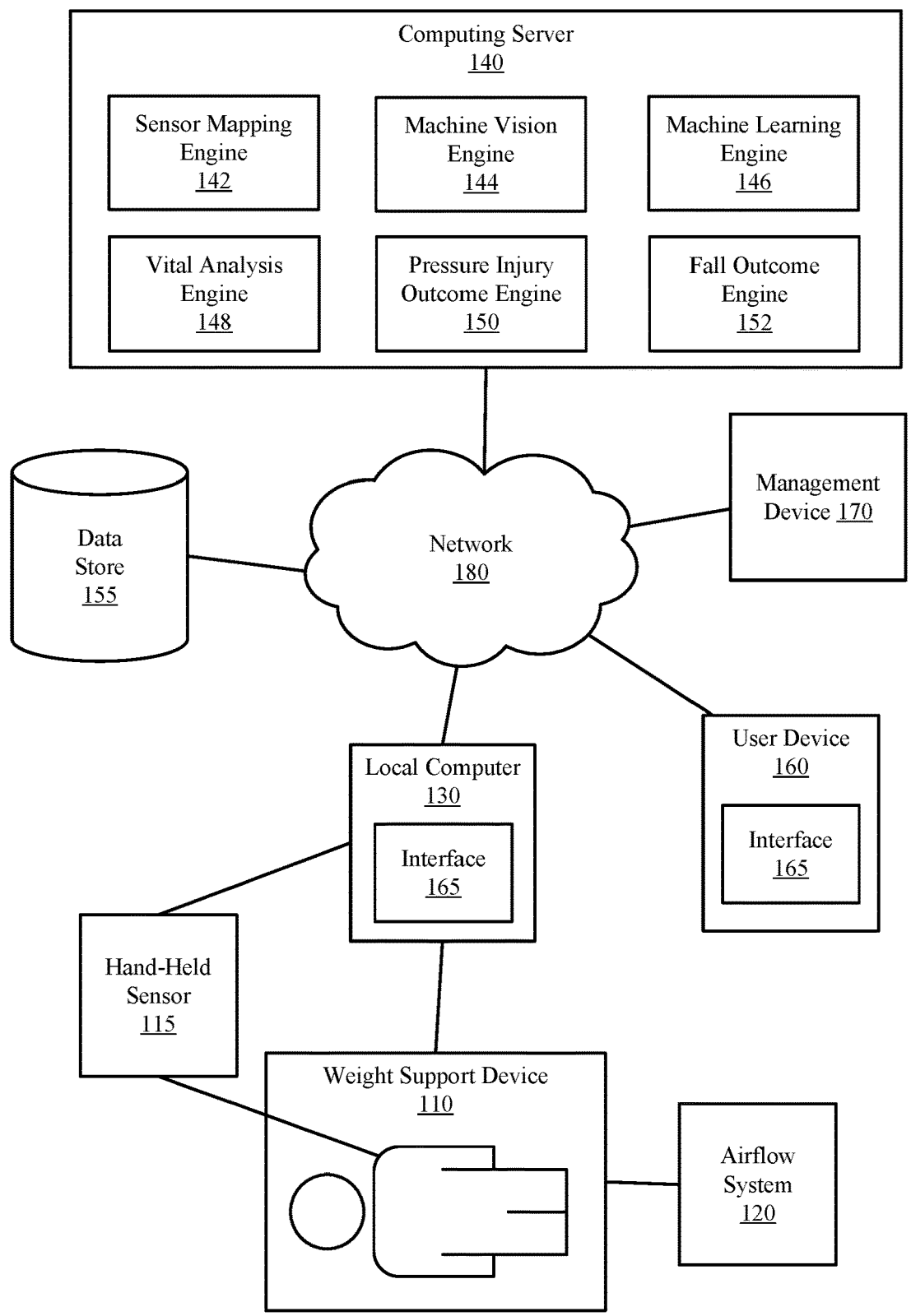
FIG. 1A is a block diagram illustrating an example system environment, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Embodiments described herein relate to a weight support device, which may be referred to as an intelligent sheet (or surface), for wireless monitoring of pressure, surface moisture, surface temperature, vital signs, and a variety of other useful clinical information. The intelligent surface may take the form of a portable and flexible mat that can provide the clinical information without any direct wiring connected to an individual supported by the weight support device. The individual may include a patient in a hospital, a patient in an elderly care setting, a person at home, etc. In some embodiments, the intelligent surface simply serves as a pad, a mattress, or a support layer for the individual to sleep, sit, or otherwise rest upon. The weight support device may include a fitted sheet, mattress, overlay, or topper with one or more embedded capacitive sensor layers, which may be combined with other sensing technologies including piezoelectric sensors, accelerometers, thermistors, or others.

In accordance with some embodiments, the weight support device can include a thin and flexible capacitive sensor grid layer that includes two types of electrodes: columns, where a sinusoidal electrical signal may be injected; and rows, where an attenuated sinusoidal signal may be detected. The electrodes are separated by a compressible, permeable dielectric material. In some embodiments, when the material is compressed by the weight from an individual, the injected electoral signal is attenuated as it passes through the dielectric. In some embodiments, when the dielectric is exposed to moisture, the injected electoral signal is attenuated as it passes through the dielectric. The attenuation is measured by sensor electronics. By arranging these sensels, or electrode pairs, on a sensor mat, a matrix of pressure values and/or surface moisture values can be captured.

Alternative or additional sensing technologies that may be used in the weight support device include piezoelectric sensors, accelerometers, electrodes, resistive pressure sensors, and thermistors. In some embodiments, the signals from these sensors can supplement the information provided by the matrix of pressure values and/or matrix of surface moisture values to provide richer information for use in a pressure injury outcome detection system and/or in a fall outcome detection system.

In accordance with some embodiments, several signal processing techniques and machine learning models are used to detect pressure injury outcomes, fall outcomes, body/joint/limb position, body movement, respiration rate, heart rate, activity level, seizures, surface/bed occupancy, incontinency issues, respiration/heart failure, and other activities such as speaking, coughing, eating, and drinking. Biometrics can be derived from the signals of the intelligent surface may include but are not limited to body position, joint locations, movement monitoring, respiration rate, and heart rate. The intelligent surface may be associated with an artificial intelligence system, which may use multiple types of machine learning models to identify the individual's pressure injury outcome (e.g., a risk of developing a pressure injury, an area of the individual's body at risk of developing the pressure injury, and an amount of time that indicates when an adjustment of a positioning of the individual is needed to avoid pressure injury) and/or the individual's fall outcome (e.g., a risk of falling off the weight support device (the intelligent surface) and an indication a fall took place).

In some embodiments, for the pressure injury outcome detection, a computer may receive raw pressure data (e.g., generated from an embedded capacitive sensor layer), raw surface moisture data (e.g., generated from an embedded capacitive sensor layer), raw surface temperature data (e.g., generated from the thermistors), a health record of an individual, or any combination thereof. The computer may generate respective extracted features. The extracted features may include various position data associated with the individual, pressure data at particular body part locations with respect to the individual, determined areas of high shear at particular body part locations with respect to the individual, surface moisture of weight support device at particular body part locations with respect to the individual, surface temperature of weight support device at particular body part locations with respect to the individual, and risk factors of the individual that may contribute to developing a pressure injury. In some embodiments, the features are fed into a system that uses a rules-based approach and/or machine learning models to automatically determine the pressure injury outcome for the individual. In some embodiments, the raw sensor data and health record may be fed directly into the rule-based approach and/or a machine learning model to determine the pressure injury outcome for the individual.

In some embodiments, for the fall outcome detection, a computer may receive raw pressure data (e.g., generated from an embedded capacitive sensor layer), a health record of an individual, or any combination thereof. The computer may generate respective extracted features. The extracted features may include various position data associated with the individual based on the pressure data and/or health record data. In some embodiments, the features are fed into a system that uses a rule-based approach, a machine learning model, or a combination of both to automatically determine a fall outcome for the individual. In some embodiments, the raw sensor data and health record may be fed directly into the rule-based approach and/or the machine learning model to determine the fall outcome for the individual.

Example System Environments

Referring now to Figure (FIG. 1A, shown is a block diagram illustrating an embodiment of an example system environment 100, in accordance with some embodiments. The components in the system environment 100 may be combined in the system with secure, password authenticated network transport, storage and retrieval of patient information compliant with healthcare information regulations and legislation. By way of example, the system environment 100 includes a weight support device 110, a hand-held sensor 115, an airflow system 120, a local computer 130, a computing server 140, a data store 155, a user device 160, a management device 170, and network 180. In various embodiments, the system environment 100 may include fewer or additional components. The system environment 100 also may include different components. Also, while some of the components in the system environment 100 may sometimes be described in a singular form, the system environment 100 may include one or more of each of the components.

The weight support device 110 may include layers that support the weight or part of the weight of a person (e.g., a patient) and include sensors that monitor various data associated with the person. Examples of the weight support device 110 include a bedding system (e.g., a mattress), a seating system (e.g., a wheelchair, a dining chair, an office chair, a car seat), a sheet, a cushion, a pillow, a pad, etc. The weight support device 110 may also be referred to as an intelligent surface. While in this disclosure the weight support device 110 is often described as a bedding system, various features and components of the bedding system may also be applied to other types of the weight support device 110 without explicitly referring to those types of the weight support device 110. The weight support device 110 may come in various sizes and different forms. For example, a bedding system may be an intelligent mattress that may include various comfort layers such as foam. In another example, a bedding system may be a pad that is intended to complement a conventional mattress (e.g., being laid on top of the mattress). A bedding system may also be used in a special setting such as in the hospital or elderly care facility. The weight support device 110 may also be a seating system that can be used as an intelligent office seat that monitors the posture of a person, a car seat (or a cushion for a car seat), or a wheelchair seat. Other examples of the weight support device 110 are also possible.

The weight support device 110 may include one or more types of sensors that are used to monitor various data about and certain vital information of the person sleeping, seating, or otherwise resting on the weight support device 110. The sensors may include a pressure sensor grid that includes an array of pressure sensing elements and a surface moisture sensor grid that includes an array of surface moisture sensing elements. The pressure sensing elements may take the form of resistive pressure sensors, fiber-optic pressure sensors, or capacitive pressure sensors. The surface moisture sensing elements may take the form of capacitive surface moisture sensors. The weight support device 110 may also include other types of sensors such as piezoelectric sensors, accelerometers, and thermistors.

The weight support device 110 may include various comfort features such as one or more microclimate fabric layers that may be used to regulate the humidity, airflow, and temperature of the surface of the weight support device 110. The sensor grid(s) may also be formed from air permeable materials so that the sensor grid layer(s) is also air permeable. The weight support device 110 may also include a comfort layer that adjusts the firmness of the device. Structures and various components of different embodiments of the weight support device 110 will be discussed in further detail with reference to FIG. 2A through FIG. 3B.

The weight support device 110 may further include an inlet that can be connected to an active air source such as the airflow system 120 to enhance the air circulation and flow inside the weight support device 110. For example, the airflow system 120 may be a fan or a pump that moves air into some of the inner layers of the weight support device 110. In turn, the air is circulated through the air-permeable layers to exit the weight support device 110 through its surfaces. The airflow system 120 may be computer-controlled based on readings from temperature sensors and humidity sensors installed at the weight support device 110 to actively regulate the microclimate of the system. The weight support device 110 may also include various accessory devices such as temperature control devices, temperature sensors, white noise generators, audio sensors, biofeedback sensors, lighting controls, and light sensors. Communication and control of the accessory devices can be performed via a Universal Serial Bus (USB) port, Firewire port, or via Bluetooth or WiFi wireless connections. Some example additional comfort features are discussed in U.S. Patent Application Publication 2018/0027988, dated Feb. 1, 2018, entitled "Bedding System with a CNN Based Machine Vision Process," which is incorporated by reference herein for all purposes.

The weight support device 110 may include an automatically adjustable surface. The weight support device 110 may receive instructions from the local computer 130, the computing server 140, or the management device 170 to adjust the surface such that a positioning of the person supported by the weight support device 110 is adjusted. For example, the surface may be adjusted via inflation bladders or servo motors. The weight support device 110 may automatically adjust its positioning, for example, by decreasing its height off of the ground. The weight support device 110 may additionally include one or more guard rails positioned on one or more sides of the weight support device 110. The guard rails may be automatically adjusted by the weight support device 110.

The weight support device 110 may generate sensor signals and be in communication with a computer to automatically detect a pressure injury outcome and/or a fall outcome of the person. The weight support device 110 may take the form of a portable flexible mat that can provide biometric information without any direct wiring connected to the person. The weight support device 110 may measure the pressure exerted by the person using a sensor grid to generate a matrix of pressure readings. The matrix of pressure readings and other sensor readings (e.g., surface moisture readings), which may be supplemented with other supporting sensors, may be provided to a computer with an artificial intelligence system which uses one or more types of machine learning networks (a convolutional neural network (CNN), a long short term memory (LSTM) network, etc.) to identify the pressure injury outcome (e.g., a risk of the person developing a pressure injury). The matrix of pressure readings and other sensor readings may also be used to deduce other information about the person that may include, but is not limited to, respiration rate, heart rate, and/or position data that includes body position, joint locations, and movement monitoring. The pressure readings and other information may be utilized by the computer with an artificial intelligence system which uses one or more types of machine learning networks to identify the fall outcome (e.g., a risk of the person falling off of the weight support device 110). Several data processing and machine learning techniques will be discussed in further detail below with reference to FIG. 5A through FIG. 6 and FIG. 8A through FIG. 11. The techniques can identify the pressure injury outcome of the person and/or the fall outcome of the person with a minimally disruptive sensing system such as the weight support device 110.

The person on the weight support device 110 may also be monitored by one or more hand-held sensors 115 that measure an amount of moisture under the person's skin and/or the person's vitals such as heart rate, respiration rate, body temperature, blood pressure, blood sugar level, etc. Depending on embodiments, the hand-held sensors 115 may be part of the weight support device 110 or independent devices. For example, in one embodiment, the weight support device 110 is equipped with sensors that can detect the heart rate, respiration rate, and body temperature. In another embodiment, the amount of moisture under the person's skin may be detected through an external hand-held sensor 115 that is not part of the weight support device 110. For example, the hand-held sensor 115 may be an edema sensor that takes the form of a device that transmits a radio frequency, an infrared frequency, or some other type of frequency light signal towards a portion of skin of the person and receive a reflected signal that provides information about the amount of moisture under the person's skin. For example, the hand-held sensor 115 may be an infrared tissue oxygenation sensor or a blood flow sensor. The hand-held sensors 115 may be professionally graded or customer graded. For example, in a hospital setting, the weight support device 110 may be used as a hospital bed for a patient who is monitored by different kinds of medically graded hand-held sensors 115. In some embodiments, the hand-held sensor 115 can inform a user (e.g., a healthcare professional) of a pressure injury outcome. In another example, one of the hand-held sensors 115 may simply be a wearable electronic device such as APPLE WATCH or a FITBIT smartwatch. For example, the heart rate of the person may be input from an external device that is embedded into the weight support device 110 or attached to the person outside of the weight support device 110. The hand-held sensors 115 may also include a pulse oximeter.

In some embodiments, the weight support device 110 and the hand-held sensors 115 may be connected to a local computer 130 that is located, for example, in the same place as the weight support device 110 (e.g., in a patient's hospital room). In some embodiments, the weight support device 110 may be equipped with processing power such as having built-in CPUs or the local computer 130 being part of the weight support device 110. In other embodiments, the local computer 130 may be a separate computer that connects to the weight support device 110 and the hand-held sensors 115 to collect data from those devices. The local computer 130 may upload the data via the network 180 to the computing server 140 for further processing. In some embodiments, the local computer 130 may also have software installed to analyze the data from the weight support device 110 and/or the hand-held sensors 115. For example, in a hospital setting, the local computer 130 may be a bedside monitor that provides analyses of various data in real-time and display the data associated the patient. In other embodiments, the local computer 130 simply collect data or perform certain data processing (such as compression, conversion of formats) for the computing server 140 to further analyze the data. The role of the local computer 130 may vary in different implementations and settings. In some embodiments, local computer 130 may not be present. For example, the weight support device 110 may be equipped with a wireless capability that can directly transmit its data to the computing server 140 for processing.

In some embodiments, a weight support device 110 (or a computer that processes the raw data of the weight support device 110) may transmit data such as visual representations of motions and positions/poses of the person, pressure data, surface moisture data, and/or surface temperature data in a secure network environment to a user (e.g., a healthcare professional) via a management dashboard (e.g., at a nursing station, front management desk in a retirement home, etc.) of a management device 170 to highlight the state and status of the individual being monitored. The management device 170 may also provide an alert system alerting the user that a patient is at risk of developing a pressure injury and/or at risk of falling off of the weight support device 110, that an adjustment of a positioning of the patient is needed, when the adjustment is needed, etc. The management device 170 may be communicatively coupled to more than one weight support device 110 and provide the status of multiple individuals to the user. The management device 170 may prioritize the individuals and provide their status accordingly based on each individual's risk of developing a pressure injury and/or risk of falling, when each individual needs their positioning adjusted, and/or how long an area or areas of each individual has been experiencing high-pressure. Also, the alert system may alert the user should there be any trends or behavior outside of preestablished parameters (e.g., oxygen level).

The computing server 140 may be a remote server that is used to analyze data collected from the weight support device 110 and the hand-held sensors 115 to predict a pressure injury outcome and/or a fall outcome of a person supported by the weight support device 110. The computing server 140 may take the form of a combination of hardware and software, such as engines 142 through 152. The computing server 140 may include some or all example components of a computing machine described with FIG. 11. The computing server 140 may take different forms. In one embodiment, the computing server 140 may be a server computer that executes code instructions to cause one or more processors to perform various processes described herein. In another case, the computing server 140 may be a pool of computing devices that may be located at the same geographical location (e.g., in a server room) or be distributed geographically (e.g., cloud computing, distributed computing, or in a virtual server network). The computing server 140 may also include one or more virtualization instances such as a container, a virtual machine, a virtual private server, a virtual kernel, or another suitable virtualization instance.

Figure 5A:
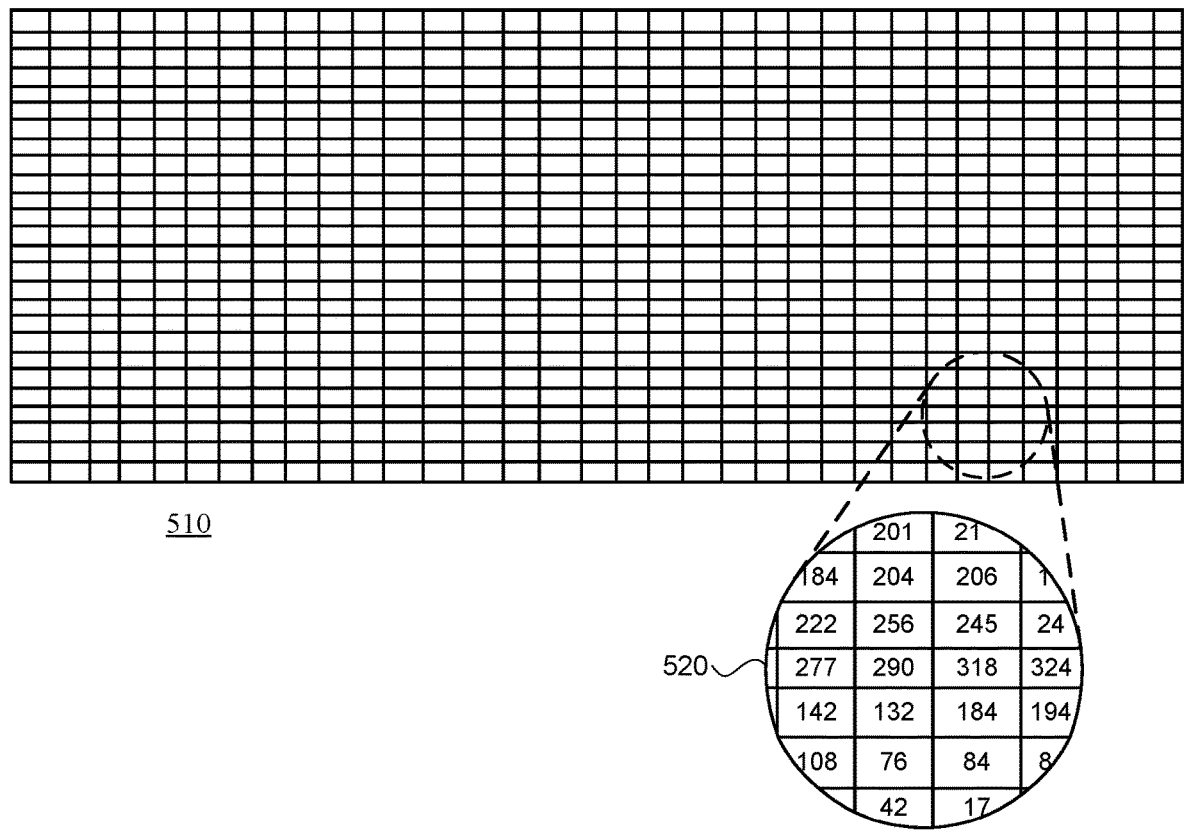
FIG. 5A is a conceptual diagram of a matrix of sensor readings generated by a sensor grid layer, in accordance with some embodiments.
Figure 5B:
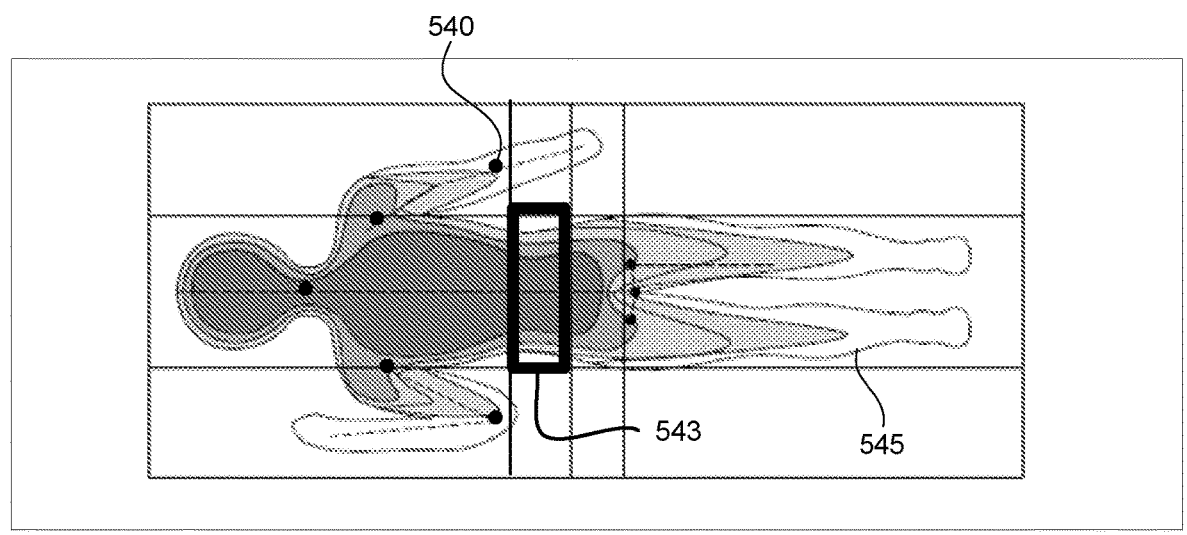
FIG. 5B is a conceptual diagram illustrating an example pressure heatmap that is generated by a matrix of sensor readings, in accordance with some embodiments.

The computing server 140 may include various algorithms for data analysis. The sensor mapping engine 142 may perform basic functions such as receiving data from the weight support device 110 and the hand-held sensors 115 and organizing the received data. For example, the sensor mapping engine 142 may organize the data measured by the array of pressure sensing elements into an array of measurements representative of the sensor array. An example of an array of sensor measurements is shown in FIG. 5A. The sensor mapping engine 140 may generate a visual representation of the array of sensor measurements. For example, the sensor mapping engine 140 may generate a two-dimensional image representation of a person, as shown in FIG. 5B. In this example, the sensor measurements are pressure measurements and areas of high-pressure (e.g., areas that correspond to pressure measurements above a threshold pressure measurement value) may be shown in a dark shade compared to areas of low-pressure (e.g., areas that correspond to pressure measurements below a threshold pressure measurement value).

The sensor mapping engine 142 may also calculate a number of parameters that are derived from the image representation. For example, a contact area can be calculated for the entire sensing area of the weight support device 110. The contact area is based on areas that correspond to pressure measurements above a minimum threshold. The contact area may provide a visual outline (e.g., a body outline) of the individual supported by the weight support device 110. Based on the body outline of the individual, the sensor mapping engine 142 may provide instruction to the weight support device 110 to only collect sensor data from the surface moisture sensing elements and/or the thermistors located on the weight support device 110 within the contact area.

In another example, the sensor mapping engine 142 may calculate an average peak pressure over the entire sensing area of the weight support device 110. In one approach, the sensor mapping engine 142 may calculate an average peak pressure by isolating a group of sensing points with the highest measured pressures (the peak pressures), then averaging those pressure values to obtain the result. A sensing point is an individual sensing element within the sensor array. For example, using a bed sensor with 1664 sensing points in the sensor area, the 16 sensing points with the highest pressure measurements could be averaged to determine the average peak pressure. The number of sensing points averaged could be 25% to 0.5%, or preferably 1%, of the total number of sensing points in the array. The number of sensing points averaged could also be 25% to 0.5%, or preferably 1%, of the total number of sensing points in the array that are above a pressure threshold, for example, 10 mmHg. The sensor mapping engine 142 may reject certain peak pressures in order to reduce the impact of creases in the sensor grid, objects in the customer's pockets, or hard edges in the customer's clothing. For example, the three highest pressure measurements can be excluded from the average peak pressure calculation.

The sensor mapping engine 142 may calculate a load calculation (e.g., another pressure-related parameter) based on the sensor data. For example, a load calculation could be used to estimate a person's weight. The sensor mapping engine 142 may estimate the person's height by adding the number of sensing points associated with a minimum pressure from the person's head to their toes when they are lying on their back.

The sensor mapping engine 142 may determine one or more areas of high shear (e.g., another pressure-related parameter). In some embodiments, the sensor mapping engine 142 determines an area of high shear based on pressure gradients between sensing points. For example, a gradient between adjacent sensing points that is greater than a threshold gradient value corresponds to an area with high shear. In some embodiments, the sensor mapping engine 142 determines one or more areas of high shear based on surface contour of the weight support device 110.

Figure 5C:
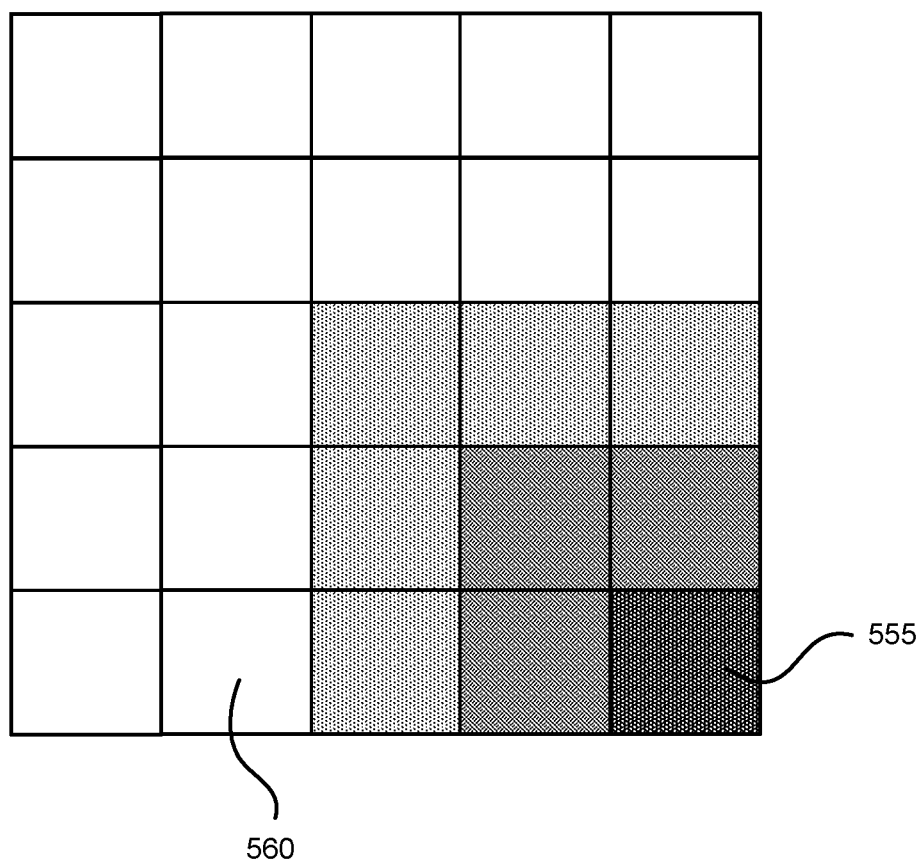
FIG. 5C is a conceptual diagram illustrating an example surface moisture heatmap that is generated by a matrix of sensor readings, in accordance with some embodiments.

The sensor mapping engine 142 may generate a visual representation of the array of sensor measurements related to surface moisture. For example, the sensor mapping engine 140 may generate a two-dimensional image representation of a surface of the weight support device 110, as shown in FIG. 5C. In this example, areas of high-moisture (e.g., areas that correspond to surface moisture measurements above a threshold measurement value) may be shown in a dark shade compared to areas of low-moisture (e.g., areas that correspond to surface moisture measurements below a threshold measurement value). The sensor mapping engine 142 may overlay the visual representation of the surface of the weight support device 110 with the visual representation of the person. The sensor mapping engine 142 may detect areas where the outline of the person overlaps with areas of high-moisture.

The machine vision engine 144 analyzes the arrays of sensor measurements, visual representations, and other parameters determined by the sensor mapping engine 142 to identify body types and to identify body position of the person supported by the weight support device 110. The machine vision engine 144 may include one or more algorithms (which could include AI or not) that extracts features from the information received from the sensor mapping engine 142. For example, when a person first lies on the weight support device 110 (as a bedding system), the machine vision engine 144 analyzes the two-dimensional visual representation of the person and derives a physical profile. The machine vision engine 144 may match the physical profile to a physical profile previously stored in the data store 155. The machine vision engine 144 may determine an identity of the person and pass this information to other components. The weight support device 110 can then be configured appropriately for that person based on information in their physical profile.

A "physical profile" is at least one physical attribute of an individual and may include attributes such as measurements of certain body features, for example, height, weight, shoulder-width, hip-width or waist-width; or ratios of these measurements, for example, shoulder to hip ratio, shoulder to waist ratio, or waist to hip ratio; body type, for example, endomorph, ectomorph, endomorph; or Body Mass Index (BMI).

The machine vision engine 144 may calculate a mass distribution for the person. For example, the machine vision engine 144 creates a peak pressure curve along a length of a person lying on their back or side. The mass distribution may be calculated from applied pressure over a given unit area. For example, the machine vision engine 144 may calculate a mass for each individual sensing point in the sensing array by multiplying the measured pressure by the area of the sensing point. Mass can also be calculated for larger areas by averaging pressure measurements over a group of sensing points, for example, 2×2 or 4×4 sensing points. The machine vision engine 144 can create a body mass curve along the length of a person lying on their back or side. The peak pressure curve and/or the body mass curve can also be used for matching a person to their physical profile. The machine vision engine 144 may calculate a center of mass for the person based on the mass calculations for all areas within the contact area and a position of each area in the contact area.

The machine learning engine 146 can detect positions and poses of the person and target body parts of the person supported by the weight support device 110. The machine learning engine 146 can continuously monitor and process the pressure data to determine a person's body position and pose. For example, position classifications can include "on back," "left side," or "right side." The machine learning engine 146 may also determine the joint locations of the person and the movement of the person. For example, changes in pressure may indicate movement or restlessness. For example, if the pressure sensing points in the contact area above a minimum pressure threshold show little variation over a period of time, then the person can be considered motionless. A variation threshold of 10% to 100% of the measured pressure can be used to determine if there is movement on a particular sensing point or group of sensing points. Details of the visioning process are further discussed with reference to FIG. 6B, FIG. 6C, and FIG. 8B.

The vital analysis engine 148 analyzes data from the weight support device 110 and the hand-held sensors 115 to determine one or more biometrics that describe the vitals of the person. For example, the vital analysis engine 148 may rely on the machine learning engine 146 and the machine vision engine 144 to determine a target body part of the person. The vital analysis engine 148 may focus on sensor data associated with the target body part to determine certain vital information of the person.

The pressure injury outcome engine 150 may be part of the machine learning engine 146 and may use information from the sensor mapping engine 142, the machine vision engine 144, the machine learning engine 146, and the vital analysis engine 148 to predict a pressure injury outcome for a person supported by the weight support device 110. The pressure injury outcome can include a risk of the person developing a pressure injury, an area of the person at risk of developing the pressure injury, and/or an amount of time that indicates when an adjustment of the positioning of the person is needed to help avoid pressure injury.

In some embodiments, the pressure injury outcome engine 150 may utilize a rules-based (or heuristics-based approach) to predict the pressure injury outcome. An example rules-based approach for predicting pressury injury outcome is discussed in U.S. Pat. No. 9,320,665, patented on Apr. 26, 2016, entitled "Risk Modeling for Pressure Ulcer Formation," which is incorporated by reference herein for all purposes.

In some embodiments, the pressure injury outcome engine 150 may utilize a machine learning model to predict the pressure injury outcome. Inputs into the machine learning model may include at least the raw sensor data measured by the pressure sensing elements. The inputs may further include one or more of: raw sensor data measured by the surface moisture sensing elements (e.g., the moisture sensing elements included in the weight support device 110), raw surface temperature data generated from the thermistors, a health record of an individual, sensor data from the hand-held sensors 115 (e.g., moisture data from a hand-held edema sensor), any additional information input by a user (e.g., results of a blanch test), information from the sensor mapping engine 142, and information from the machine visions engine 146.

In some embodiments, the pressure injury outcome engine 150 provides an alert, notification, and/or message to a user (e.g., a nurse or a caregiver) that the positioning of the person should be adjusted. In some examples, the notification may instruct the user at what time the adjustment should take place and/or which area(s) of the person needs its position adjusted. The notification may also provide a visual representation to the user of the person with at least one area of the person's body called out as the area of the person that needs positioning adjustment.

In some embodiments, the pressure injury outcome engine 150 provides instructions to the weight support device 110 based on the pressure injury outcome determination. For example, the pressure injury outcome engine 150 may instruct the weight support device 110 to adjust the positioning of the person.

The fall outcome engine 152 may be part of the machine learning engine 146 and may use information from the sensor mapping engine 142, the machine vision engine 144, and the machine learning engine 146 to predict a fall outcome for a person supported by the weight support device 110. The fall outcome can include a risk of the person falling off of the weight support device 110 and/or an indication that the person has experienced a fall.

In some embodiments, the fall outcome engine 152 may utilize a rule-based approach for predicting the fall outcome. In some embodiments, the fall outcome engine 152 may utilize a machine learning model to predict the fall outcome. Inputs into the rule-based approach or the machine learning model may include at least the raw sensor data measured by the pressure sensing elements (e.g., pressure readings). The inputs may further include one or more of: a health record of an individual, information from the sensor mapping engine 142, and information from the machine visions engine 146. In some embodiments, the fall outcome engine 152 provides an alert, notification, and/or message to the user that the positioning of the person should be adjusted to avoid a fall, or the person needs assistance after experiencing a fall. In some examples, the notification may instruct the user how best to adjust the positioning of the person.

In some embodiments, the fall outcome engine 152 provides instructions to the weight support device 110 based on the fall outcome determination. For example, the fall outcome engine 152 may instruct the weight support device 110 to adjust the positioning of the person.

The data store 155 includes one or more storage units such as memory that takes the form of non-transitory and non-volatile computer storage medium to store various data that may be uploaded by the local computer 130, by the weight support device 110, or by other components of the system environment 100. The computer-readable storage medium is a medium that does not include a transitory medium such as a propagating signal or a carrier wave.

The data store 155 may store health records of person(s) supported by the weight support device 110. The health records may have been input into the data store 155 by the local computer 130, the user device 160, the management device 170, etc. at any time. Each health record corresponds to a particular person and includes information about the person, such as an age, mobility information, nutrition information, pre-existing skin conditions, incontinent issues, medical history, current medications, results of blanch test, etc. The health record may also include information about one or more areas of the person (e.g., a wound site, a surgical site, etc.) that are to avoid pressure. The data store 155 may store sensor data (e.g., pressure data) captured by the weight support device 110 and also analysis results generated by the computing server 140, such as determined position data, pressure injury outcome(s), and/or fall outcome(s). The sensor data and analysis results corresponding to a particular person may be associated with a health record of that person and stored within the health record. In some embodiments, the data store 155 aggregates sensor data received from multiple weight support devices 110 by which the person has been supported. For example, in a hospital setting, a patient may be admitted to the hospital by a wheelchair, be treated on a first bedding system (e.g., a stretcher) in an emergency care and be transferred to a second bedding system (e.g., a hospital bed) in a patient room. The data store 155 may receive data from the wheelchair, the first bedding system, and the second bedding system for the computing server 140 to continuously monitor the pressure readings related to the patient. The data store 155 may additionally store sensor data received from the hand-held sensors 115.

The data store 155 may store historical patient data. The historical patient data includes health record data, sensors data, and analysis results for patients that have historically been supported by the weight support device 110. The historical patient data may be utilized by one or more machine learning models to train the models to determine pressure injury outcomes and/or fall outcomes for current or future patients.

The data store 155 may take various forms. In one embodiment, the data store 155 communicates with other components by the network 180. This type of data store 155 may be referred to as a cloud storage server. Example cloud storage service providers may include AWS, AZURE STORAGE, GOOGLE CLOUD STORAGE, etc. In another embodiment, instead of a cloud storage server, the data store 155 is a storage device that is controlled and connected to the computing server 140. For example, the data store 155 may take the form of memory (e.g., hard drives, flash memories, discs, ROMs, etc.) used by the computing server 140 such as storage devices in a storage server room that is operated by the computing server 140.

The user device 160 may be a portable electronic device for transmitting data. The user device 160 may be possessed by the person using (e.g., supported by) the weight support device 110. The user device 160 may be possessed by a different user in the system environment 100. For example, the user device 160 may be used by a healthcare professional, caregiver, etc. Examples of user devices 160 include personal computers (PCs), desktop computers, laptop computers, tablet computers, smartphones, wearable electronic devices such as smartwatches, or any other suitable electronic devices. The user device 160 may include an application such as a software application provided by the computing server 140. The application may provide various results and analyses of the sensor data collected by the weight support device 110 and hand-held sensor 115 and may also allow the person and/or the user to adjust various settings associated with weight support device 110, such as the airflow system 120. An application may be of different types. In one case, an application may be a web application that runs on JavaScript, etc. In the case of a web application, the application cooperates with a web browser to render a front-end interface 165. In another case, an application may be a mobile application. For example, the mobile application may run on Swift for iOS and other APPLE operating systems or on JAVA or another suitable language for ANDROID systems. In yet another case, an application may be a software program that operates on a desktop computer that runs on an operating system such as LINUX, MICROSOFT WINDOWS, MAC OS, or CHROME OS.

An interface 165 may be a suitable interface for the local computer 130 and/or the user device 160 to interact with the computing server 140. The interface 165 may include various visualizations and graphical elements to display notifications and/or information to users and may also include input fields to accept inputs from users. A user may communicate to the application and the computing server 140 through the interface 165. The interface 165 may take different forms. In one embodiment, the interface 165 may be a web browser such as CHROME, FIREFOX, SAFARI, INTERNET EXPLORER, EDGE, etc. and the application may be a web application that is run by the web browser. In another application, the interface 165 is part of the application. For example, the interface 165 may be the front-end component of a mobile application or a desktop application. The interface 165 also may be referred to as a graphical user interface (GUI) which includes graphical elements to display a digital heatmap, other pressure injury-related information, or other fall-related information. In another embodiment, the interface 165 may not include graphical elements but may communicate with the computing server 140 via other suitable ways such as application program interfaces (APIs).

The various functionalities of the computing server 140 may also be performed by the local computer 130 or the user device 160, depending on the implementation and configuration. For example, the software algorithms that perform the various process associated with engines 142, 144, 146, 148, 150, and 152 in the computing server 140 may also reside in the local computer 130 or a mobile application of the user device 160 so that the local computer 130 or the user device 160 may directly analyze the sensor data generated by the weight support device 110. Results generated may be displayed at the user device 160, at the local computer 130, or at both devices. The computing server 140 may manage a mobile application that can cause the local computer 130 or the user device 160 to generate a user interface 165 that displays various results, predictions, determinations, notifications, visual representations, and graphical illustrations of sensor data generated by the weight support device 110. In some embodiments, the weight support device 110 may also include computing components and software for analyzing the data directly and display the results.

The network 180 provide connections to the components of the system environment 100 through one or more sub-networks, which may include any combination of the local area and/or wide area networks, using both wired and/or wireless communication systems. In one embodiment, the network 180 use standard communications technologies and/or protocols. For example, a network 180 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 180 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 180 may be represented using any suitable format, such as hypertext markup language (HTML), extensible markup language (XML), JavaScript object notation (JSON), structured query language (SQL). In some embodiments, all or some of the communication links of a network 180 may be encrypted using any suitable technique or techniques such as secure sockets layer (SSL), transport layer security (TLS), virtual private networks (VPNs), Internet Protocol security (IPsec), etc. The network 180 also include links and packet switching networks such as the Internet.

Figure 1B:
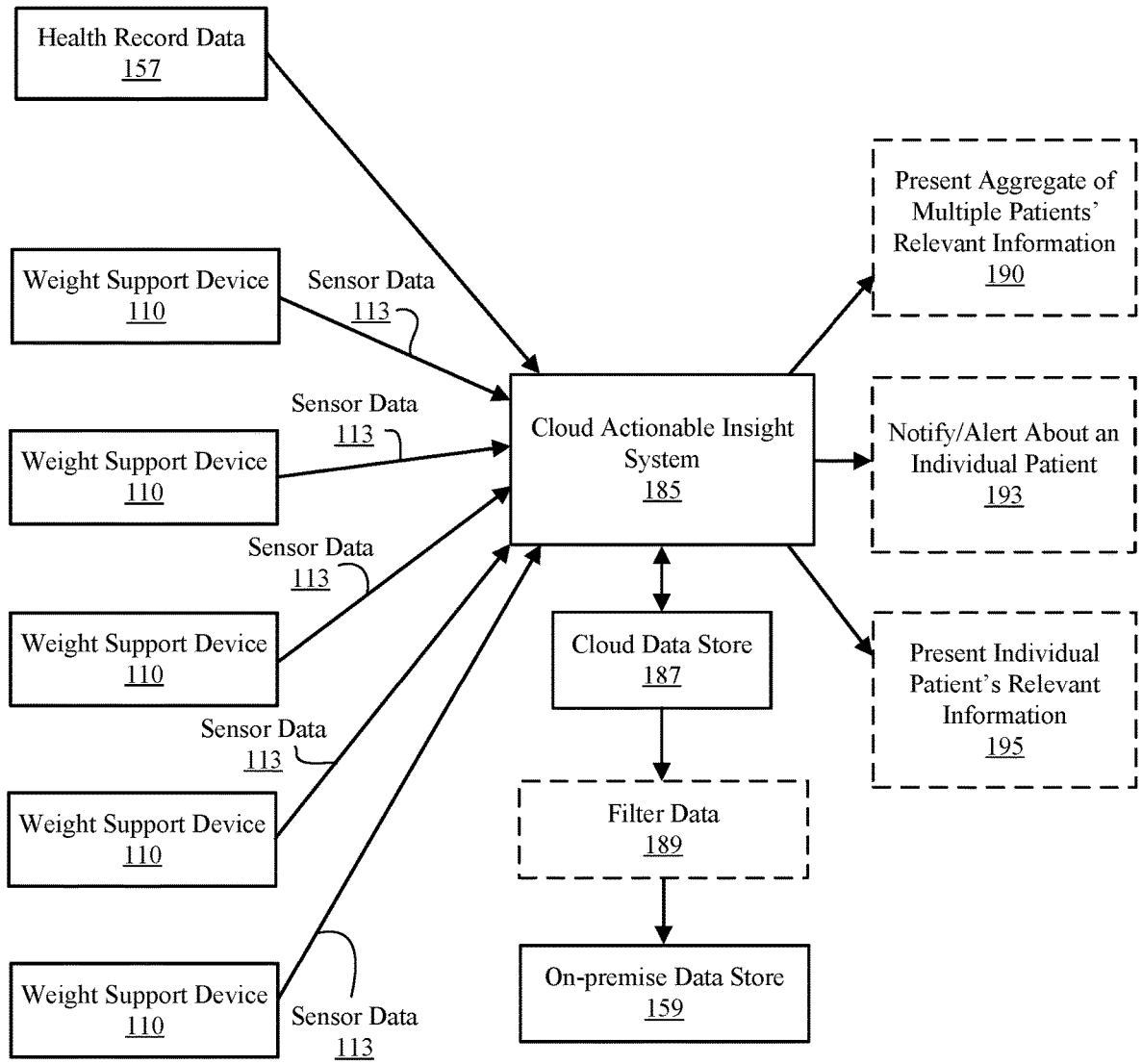
FIG. 1B is a block diagram illustrating a continuity of care example system environment for a patient, in accordance with some embodiments.

FIG. 1B is a block diagram illustrating a continuity of care example system environment 105 for a patient, in accordance with some embodiments. In some example scenarios of patients' stays at a hospital, the patients coming out of an operating room may eventually develop a pressure injury while in a hospital bed recovering from surgery—but the injury may have actually started with the patient experiencing high pressures while sedated in the operating room during their surgery. In a hospital setting with a multitude of patients, each patient can be supported by different weight support devices 110 throughout their stay (e.g., from a wheelchair, to a first bedding system, to a second bedding system, and so on), a system to monitor and track the pressure injury outcomes may provide better visibility regarding where a pressure injury or risk of pressure injury first started. The system to monitor and track the fall outcomes may provide better visibility regarding how best to position a patient to avoid a fall from the weight support devices 110.

The continuity of care example system environment 105 for a patient tracks sensor data 113 received from various weight support devices 110. The sensor data 113 may include pressure data, surface moisture data, surface temperature data, and any other data measured by each weight support device 110. Additional data may be supplied by the data store 155. For example, the health record data 157 associated with the patient is monitored in the system environment 105. The sensor data 113 and health record data 163 are provided to a cloud actionable insight system 185 that may include the computing server 140. The cloud actionable insight system 185 may store the sensor data 113 and the health record data 157 in the cloud data store 187. The data in the cloud data store 187 may be filtered 189 and stored in the on-premise data store 159 (e.g., at the hospital). The cloud actionable insight system 185 analyzes the sensor data 113 and the health record data 157 to determine a pressure injury outcome and/or a fall outcome for the patient as described above.

In some embodiments, the cloud actionable insight system 185 presents 190 an aggregate of the multiple patients' relevant information to the healthcare professional and/or caregivers via the local computer 130, the user device 160, and/or the management device 170. In some embodiments, the cloud actionable insight system 185 may prioritize how and/or when each patient's relevant information is presented. For example, the cloud actionable insight system 185 may determine to display information about a patient with a higher risk of developing a pressure injury and/or a patient at risk of developing a pressure injury sooner to the healthcare professional before displaying information about a patient with a lower risk and/or a patient at risk of developing a pressure injury later. In another example, the cloud actionable insight system 185 may determine to display information about a patient with a higher risk of experiencing a fall and/or a patient at risk of experiencing a fall sooner to the healthcare professional before displaying information about a patient with a lower risk and/or a patient at risk of experiencing a fall later. The relevant information may include a visual representation of all patients currently being support by a weight support device 110 and any corresponding pressure injury outcomes and/or fall outcomes for those patients.

In some embodiments, the cloud actionable insight system 185 may notify and/or alert 193 the healthcare professional, caregivers, and/or patient via the local computer 130, the user device 160, and/or the management device 170 that a patient is at risk of developing a pressure injury and/or at risk of falling off of the weight support device 110. The notification and/or alert may also provide information about where the patient is at risk of developing the pressure injury, when the patient is at risk of developing the pressure injury, how to adjust a positioning of the patient to prevent the pressure injury, and/or to adjust the positioning of the patient to prevent the fall. In some embodiments, the cloud actionable insight system 185 may notify and/or alert 193 the healthcare professional, caregivers, and/or patient that an area of the patient that is to avoid pressure is currently experiencing pressure and that an adjustment of the positioning of the patient is needed immediately. In some embodiments, the cloud actionable insight system 185 may present 195 to the healthcare professional and/or caregivers via the local computer 130, the user device 160, and/or the management device 170 an individual patient's relevant information. The relevant information may include a visual representation of the patient currently being support by a weight support device 110 and any corresponding pressure injury and/or fall outcomes for that patient. In some embodiments, the relevant information may provide a record of the patient's skin condition throughout their hospital stay for more targeted and efficient care by giving the healthcare providers/caregivers historical patient data that can be used by the cloud actionable insight system 185 for recommendations for treatment.

The continuity of care system environment 105 can translate to better patient outcomes due to the visibility of the patient's condition across every stage of their clinical journey. In an example, the cloud actionable insight system 185 can track the patient at arrival (e.g., on a first mattress), at pre-operation (e.g., on a second mattress), during surgery (e.g., on a third mattress), during post-op (e.g., on a fourth mattress), and at home (e.g., with a take-home mattress). In this example, the cloud actionable insight system 185 (e.g., via the pressure injury outcome engine 150) may determine the patient became at risk of developing a pressure injury on their right hip during surgery, as such the cloud actionable insight system 185 notified/alerted 193 the nurse in post-op to position the patient such that the right hip of the patient will have little to no pressure. In post-op, the cloud actionable insight system 185 determines the patient is at risk of developing a pressure injury on their right shin, as such the cloud actionable insight system 185 notified/alerted 193 the nurse in post-op to adjust the positioning of the patient such that the right shin experiences little to no pressure. At home, the cloud actionable insight system 185 recommends to the patient or other caregiver to position the patient on their left side to allow the patient's body parts that were at risk of developing pressure injury to recover. In this example, the cloud actionable insight system 185 (e.g., via the fall outcome engine 152) may determine the patient in post-op is at risk of falling off of the weight support device 110 via the patient's left side on several occasions (e.g., at three different time instances), as such the cloud actionable insight system 185 notified/alerted 193 the nurse in post-op to adjust the positioning of the patient so that a fall could be avoided. At home, the cloud actionable insight system 185 recommends to the patient or other caregiver to position the patient with a bolster along their left side to aid in the prevention of the patient becoming at risk of falling or experiencing a fall.

In some embodiments, the cloud actionable insight system 185 may compile one or more compliance reports related to pressure injury outcomes and/or fall outcomes of patient(s). For example, a compliance report may include how many (or a percentage of) patients that had their positioning adjusted within a specified amount of time after the cloud actionable insight system 185 provided a corresponding notification to a healthcare professional, how many (or a percentage of) patient positioning adjustments that took place without the patient(s) developing any pressure injury, how many (or a percentage of) patient positioning adjustments that took place without the patient(s) experiencing a fall, how many (or a percentage of) patient positioning adjustments that took place where the patient(s) did develop a pressure injury and where the pressure injury developed, how many (or a percentage of) patient positioning adjustments that were initiated by the patient, the healthcare professional, and/or the weight support device. The compliance reports may be provided by the cloud actionable insight system 185 to the cloud data store 179 and/or the on-premise data store 159.

While a hospital and home setting are provided as an example, continuity of care may also be applied in other settings in various embodiments.

Example Weight Support Device Configurations

Figure 2A:
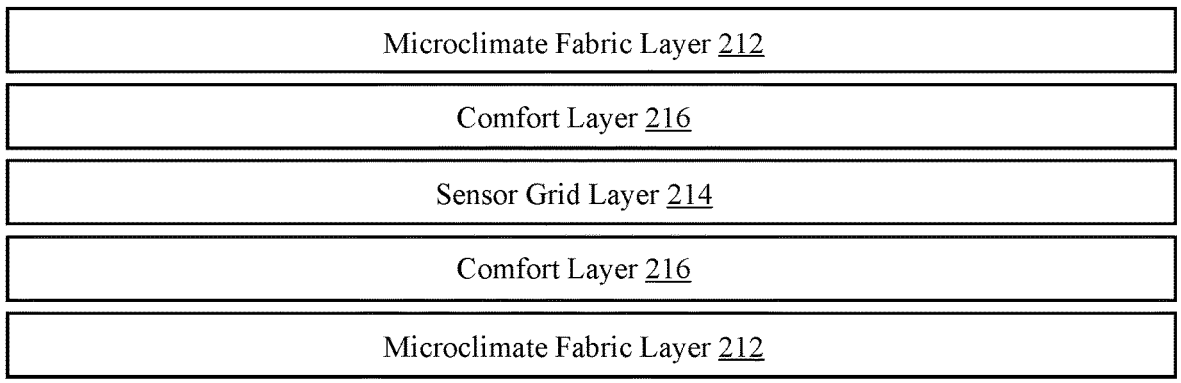
FIGS. 2A, 2B, and 2C are block diagrams illustrating cross-sectional views of various example configurations of weight support devices, in accordance with some embodiments.
Figure 2B:
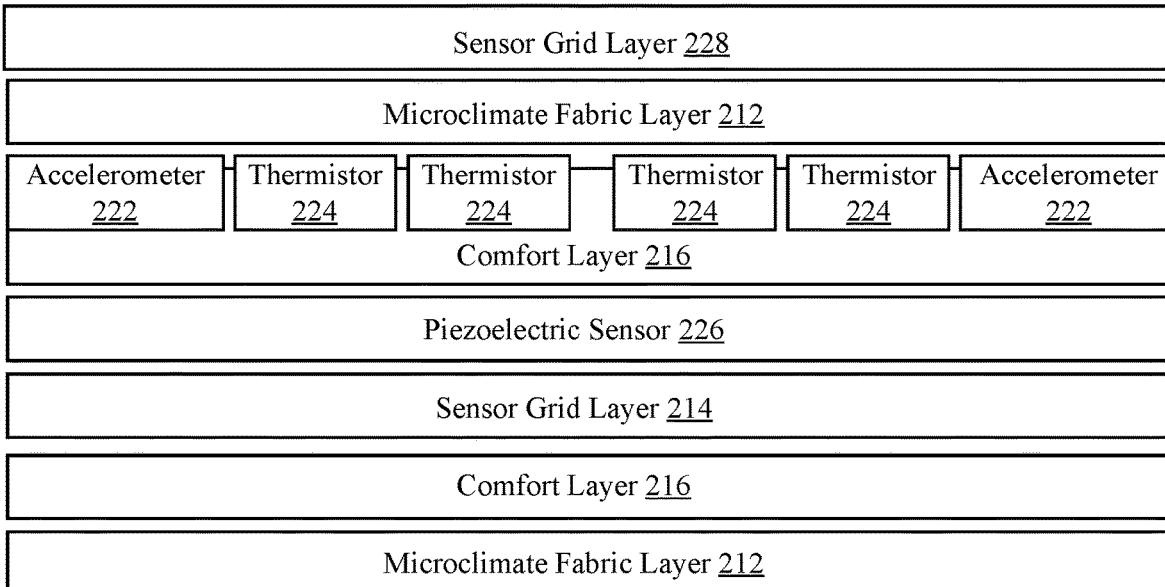
Figure 2C:
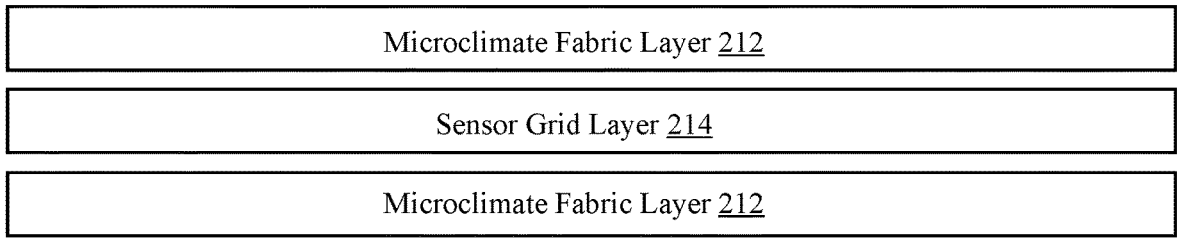

FIGS. 2A, 2B, and 2C are block diagrams illustrating cross-sectional views of various example configurations of weight support devices, in accordance with some embodiments. The weight support devices 210, 220, and 230 are examples of the weight support device 110 shown in FIG. 1A. The configurations and layers shown in FIG. 2A through FIG. 2C are for example only. In various embodiments, a weight support device may include different, fewer, or additional layers. Certain orders of the layers may also be changed. Furthermore, the layer configuration in one example may be combined with that in another example. Depending on embodiments, the weight support device may be one-sided or two-sided. One or more layers may be removable from the weight support device for washing and cleaning. Also, while many example embodiments discussed herein have air-permeable structure or features, an embodiment of the weight support device 110 may also be not air-permeable or some of the air-permeable structure may not be present.

Referring to FIG. 2A, the weight support device 210 includes microclimate fabric layers 212 as outer layers, a sensor grid layer 214 as a middle layer, and one or more comfort layers 216 that may be used to sandwich or cover the sensor grid layer 214. The entire weight support device 210 may be wrapped by one or more microclimate fabric layers 212.

A microclimate fabric layer 212 may provide regulation to microclimates such as moisture, air, heat, cooling, humidity to the weight support device 210, particularly for the microclimate that may be formed between its surface and the skin of a person. For example, the microclimate fabric layer 212 may be used to reduce the skin temperature and limit the skin's moisture level. The microclimate fabric layer 212 may be a layer that is intended to be directly in contact with the person. The microclimate fabric layer 212 may be medical-graded. The fabric used may be air permeable and washable. The fabric may be formed from suitable materials such as polyester, polyamide, or a composite fabric. To further reduce build-up of moisture, the fabric may be coated with a water-resistant material.

The comfort layer 216 may be formed from foam or other suitable materials that may be used in mattresses, cushions, or seats. The comfort layer 216 may be located below the microclimate fabric layer 212 and above the sensor grid layer 214 to serve as a cushion layer to reduce the potential discomfort brought by the sensor grid layer 214 that might include more rigid components. The material and the thickness of the comfort layer 216 may be selected based on the sensitivity of the sensor grid layer 214. Although the comfort layer 216 may reduce the sensitivity of the sensor grid layer 214, the material of the comfort layer 216 selected should allow the sensor grid layer 214 to perform measurements such as pressure that are related to the person supported by the weight support device 210. Also, in some embodiments, to make the entire weight support device 210 air permeable, air-permeable material such as foam may be selected. The thickness of the comfort layer 216 may also be adjusted based on a balance of the comfort provided by the comfort layer 216 and the sensitivity of the sensor grid layer 214.

The sensor grid layer 214 includes one or more sensor grids, which may include a plurality of sensing points distributed in a target area or substantially the entire surface of the weight support device 210 for taking measurements at different locations. The sensor grid layer 214 may include a pressure sensor grid that includes an array of pressure sensing elements. The pressure sensing elements may take the form of resistive pressure sensors, fiber-optic pressure sensors, or capacitive pressure sensors. In some embodiments, the sensor grid layer 214 may have a configuration that makes the sensor grid layer 214 air permeable. An example of the configuration of the sensor grid layer 214 will be discussed in further detail below with reference to FIG. 3A and FIG. 3B.

In one example embodiment, the sensor grid layer 214 may take the form of a thin and flexible capacitive pressure sensor that includes two types of electrodes: columns and rows. Sinusoidal electrical signals are injected at the column electrodes while attenuated sinusoidal signals are detected at the row electrodes, or vice versa. The layer of column electrodes and the layer of row electrodes may be separated by a compressible dielectric material. As a result of the material being compressed by the weight of the person supported by the weight support system 210, the injected electoral signal is attenuated as the signal passes through the dielectric. The attenuation is measured by sensor electronics. A plurality of sensing points that may be formed at the intersections of the column and row electrodes. By arranging the sensing points on a sensor mat, a matrix of pressure values can be captured.

Referring to FIG. 2B, a second example of a weight support device 220 is illustrated. The weight support device 220 may include additional layers (e.g., a moisture sensor grid layer 228 positioned above the microclimate fabric layer 212) and/or additional sensors compared to the weight support device 210.

The moisture sensor grid layer 228 measures surface moisture data. The moisture sensor grid layer 228 may include a surface moisture sensor grid that includes an array of surface moisture sensing elements. The surface moisture sensing elements may take the form of capacitive surface moisture sensors. The capacitive surface moisture sensors may include two types of electrodes: columns and rows. Sinusoidal electrical signals are injected at the column electrodes while attenuated sinusoidal signals are detected at the row electrodes, or vice versa. The column electrodes and the row electrodes may be separated by a permeable dielectric material. As a result of the material being exposed to moisture, the injected electoral signal is attenuated as the signal passes through the dielectric. The attenuation is measured by sensor electronics. A plurality of sensing points that may be formed at the intersections of the column and row electrodes. By arranging the sensing points on a sensor mat, a matrix of surface moisture values can be captured.

The weight support device 220 may include additional sensors, for example one or more accelerometers 222, one or more thermistors 224, a piezoelectric sensor 226, and one or more inertial measurement unit (IMU) sensors (not shown). The accelerometers 222 and the thermistors 224 may be located above the comfort layer 216 so that the sensors are closer to the person. The accelerometers 222 may be used to monitor the movement of the person. The movement data generated by the accelerometers 222 may be used to deduce certain vital measurements such as the heart rate and the respiration rate. The movement data may also be used to deduce the person's condition, such as the person's sleep condition. The thermistors 224 may be used to directly measure the person's skin temperature or serve as proxies to measure the person's temperature (e.g., by measuring a surface temperature). The piezoelectric sensor 226 may also take the form of a sensor grid and may be used as another pressure sensor that is specialized in making certain measurements. For example, the piezoelectric sensor 226 may be specialized in generating pressure data that can be used to deduce the person's heart rate. On the other hand, the sensor grid layer 214 may generate sensor data that is used to deduce other biometrics, such as respiration rates, and poses. The IMU sensors may be used to directly measure surface contours on the surface of the weight support device 110. For example, a change in the IMU sensor's orientation may directly map to a change in the surface of the weight support device 110. A location with a significant change in surface contour (e.g., a location with a deep valley or tall peak) corresponds to a location with high shear.

The signals (sensor data) from the additional layers and/or sensors shown in the weight support device 220 can supplement the information provided by the matrix of pressure values generated by the sensor grid layer 214 to provide richer information for use in the pressure injury outcome detection system and or fall outcome detection system. Alternatively, or additionally, moisture readings, such as skin moisture levels, may also be measured by a hand-held sensor 115 such as a tissue edema sensor.

Conventional methods for measuring surface moisture include one of the following form factors: (1) a one-time use disposable sticker that changes color when exposed to a certain level of moisture, (2) a reusable rigid prong(s) that measure the change in conductivity of the material they are embedded in that results from changing levels of moisture, and (3) a water detection cable or probe connected to a unit for leak detection. These conventional methods are not ideal as they either involve human intervention for the measurement to take place or are not comfortable for a patient. The moisture sensor grid layer 228 with array of surface moisture sensing elements disclosed herein can provide a multiple, thin, flexible, and reusable form factor with little to no human intervention required for measurements to take place. The form factor may be a single strip/sensing element or a high-resolution matrix of sensing elements.

Figure 2D:
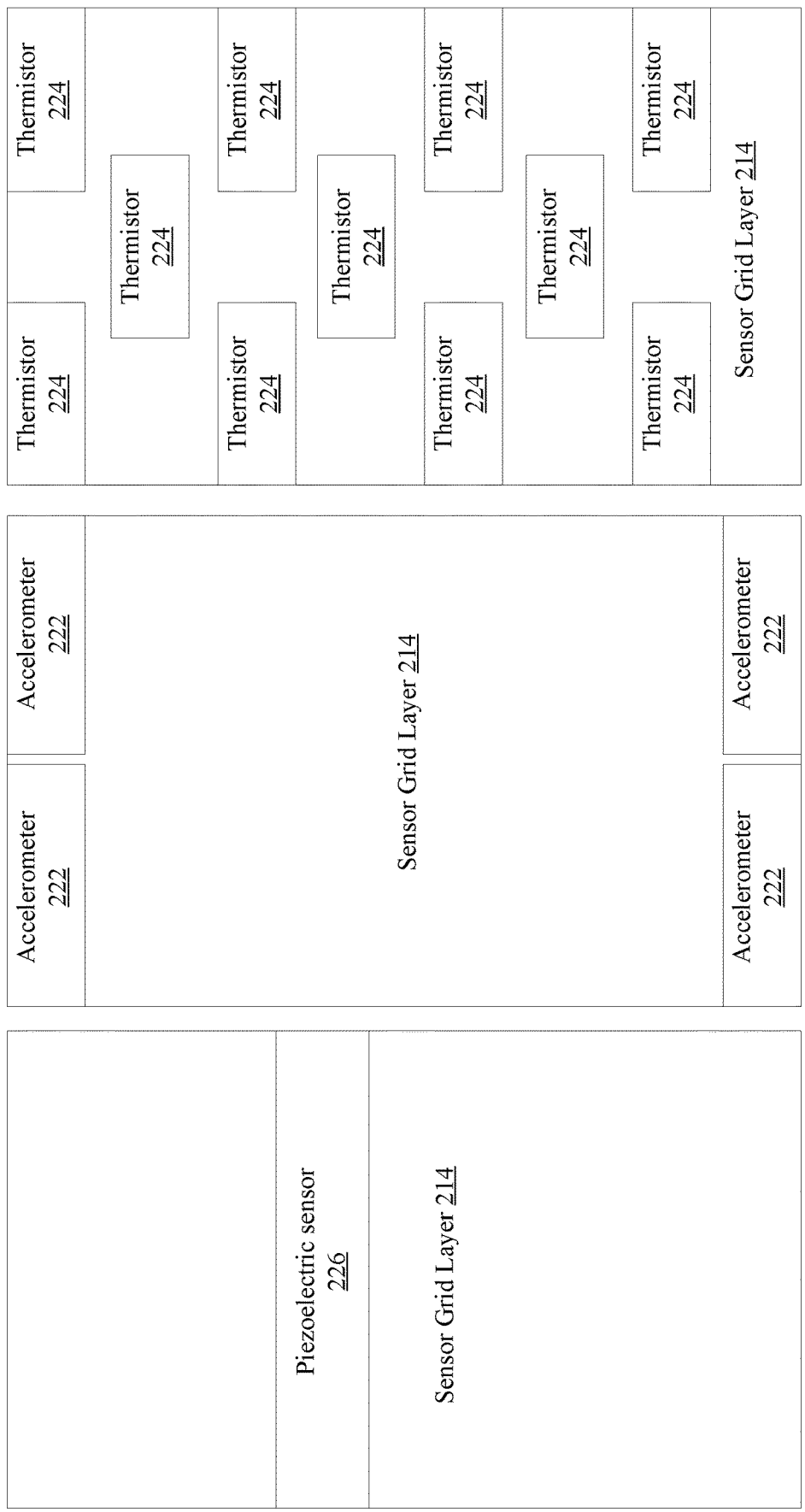
FIG. 2D is a conceptual diagram that shows several example top views of various weight support devices, in accordance with some embodiments.

FIG. 2D is a conceptual diagram that shows several example top views of various weight support devices as bedding systems to illustrate example positions of various sensors locations, in accordance with various embodiments. The sensor grid layer 214 may be located throughout substantially the entire surface of the bedding system. The piezoelectric sensor 226 may be specialized in measuring the heart rates of the person and may be located in the area that corresponds to the person's main body, such as the chest area. For example, in one embodiment, the piezoelectric sensor 226 may be located in the area, lengthwise, between 20% of the length and the midpoint of the length. The accelerometers 222 may be located at the corners of the bedding system to monitor the movement of the person. The thermistors 224 may be distributed throughout the area of the bedding system to measure a surface temperature at different parts of the weight support system. The distribution may be uniform or may be more concentrated in particular target areas. The positions of the sensors may change based on the type of weight support devices. For example, in a seating system, the piezoelectric sensor 226 may be located at the back support of the seating system.

The structure of the weight support device can be changed to meet the implementation needs. For example, for short term monitoring applications, the structure of the weight support device can be simplified to just the microclimate fabric layer 212 and the sensor grid layer 214, as illustrated in FIG. 2C as the weight support device 230. The simplification of the weight support device 230 may reduce the cost of manufacturing and also reduce the thickness of the system for easier storage. For a longer-term but basic monitoring applications, such as in household situations where end users would like to monitor their day-to-day sleep conditions, body position, joint locations, movement monitoring, respiration rate, and heart rate the sensor grid layer 214 may be used (or, in some situations, with the addition of the piezoelectric sensor 226). The simpler weight support device 210 may be used in these situations. For more complex and long-term monitoring applications, such as in intensive care situations or in other hospital settings, where various biometrics may need to be monitored, the addition of the second sensor grid layer 214 and supplementary sensors such as accelerometers 222, thermistors 224, and hand-held sensors 115 may be used to supplement the weight support device 220.

Figure 2E:
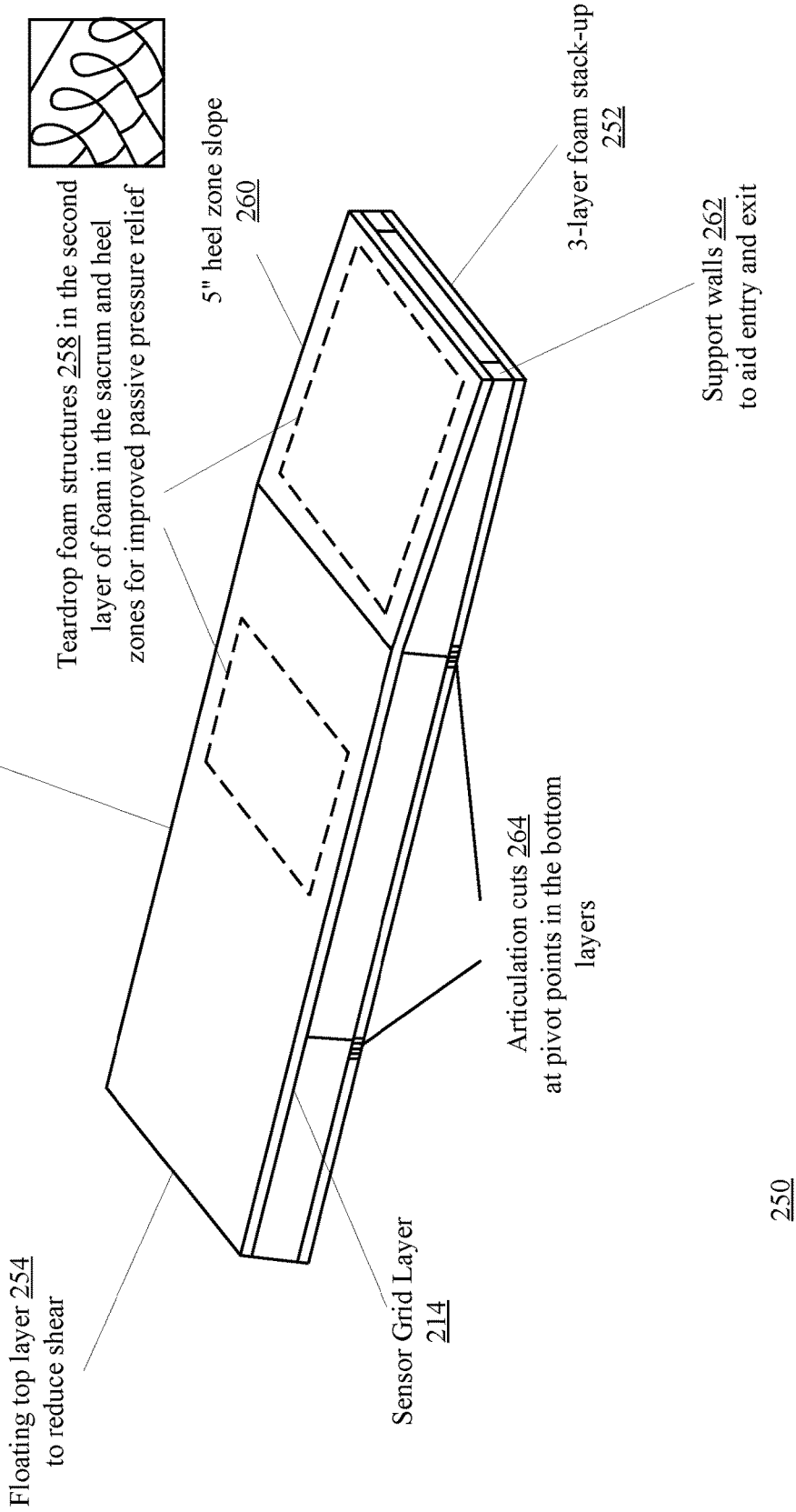
FIG. 2E is a perspective view of an example weight support device, in accordance with some embodiments.

FIG. 2E is a perspective view of an example weight support device 250 that illustrates one or more additional features that may or may not present in various implementations, in accordance with some embodiments. The weight support device 250 may be an example of the weight support device 110 and may not include a microclimate fabric layer 212, or at least is not shown in FIG. 2E. The weight support device 250 includes a 3-layer foam stack up 252 and a floating top layer 254 to reduce shear. The top layer 254 may be floating in a sense that it is not entirely securely attached to the rest of the layers. The top layer 254 may be an open-cell polyurethane foam 256 to prevent overheating characteristics of other memory foams. The weight support device 250 may also include teardrop foam structures 258 in the second layer of foam in the sacrum and heel zones for improved passive pressure relief. The weight support device 250 may further include a heel zone slope 260 for increased comfort. At both side edges, the weight support device 250 may include support walls 262 to aid entry and exit. The weight support device 250 may further include articulation cuts 264 at pivot points in the bottom layers. The articulation cuts 264 reduces the image artifacts of the sensor grid layer 214.

Example Sensor Grid Configuration

Figure 3A:
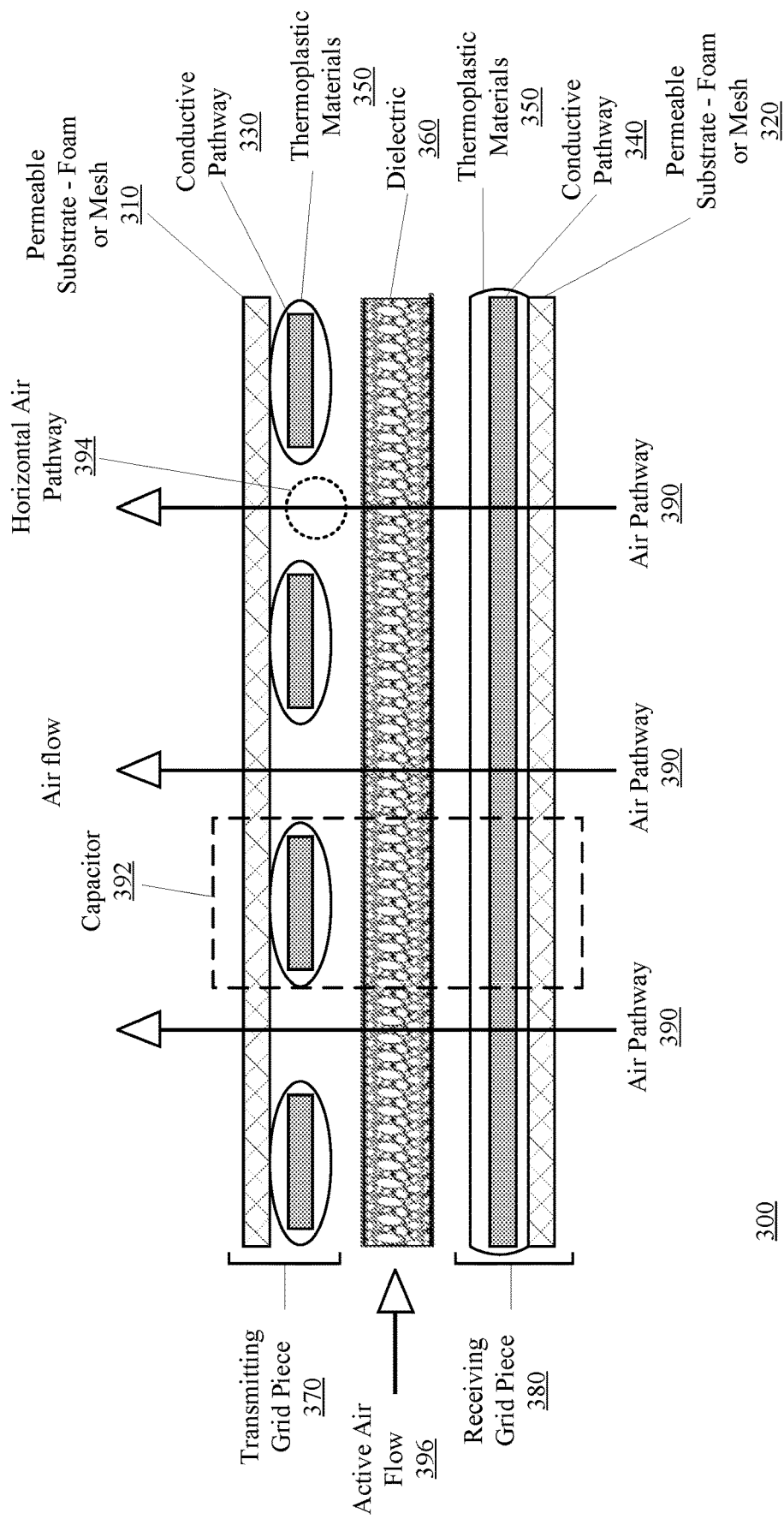
FIG. 3A is a conceptual diagram illustrating a cross-sectional view of an example sensor grid layer, in accordance with some embodiments, in accordance with some embodiments.
Figure 3B:
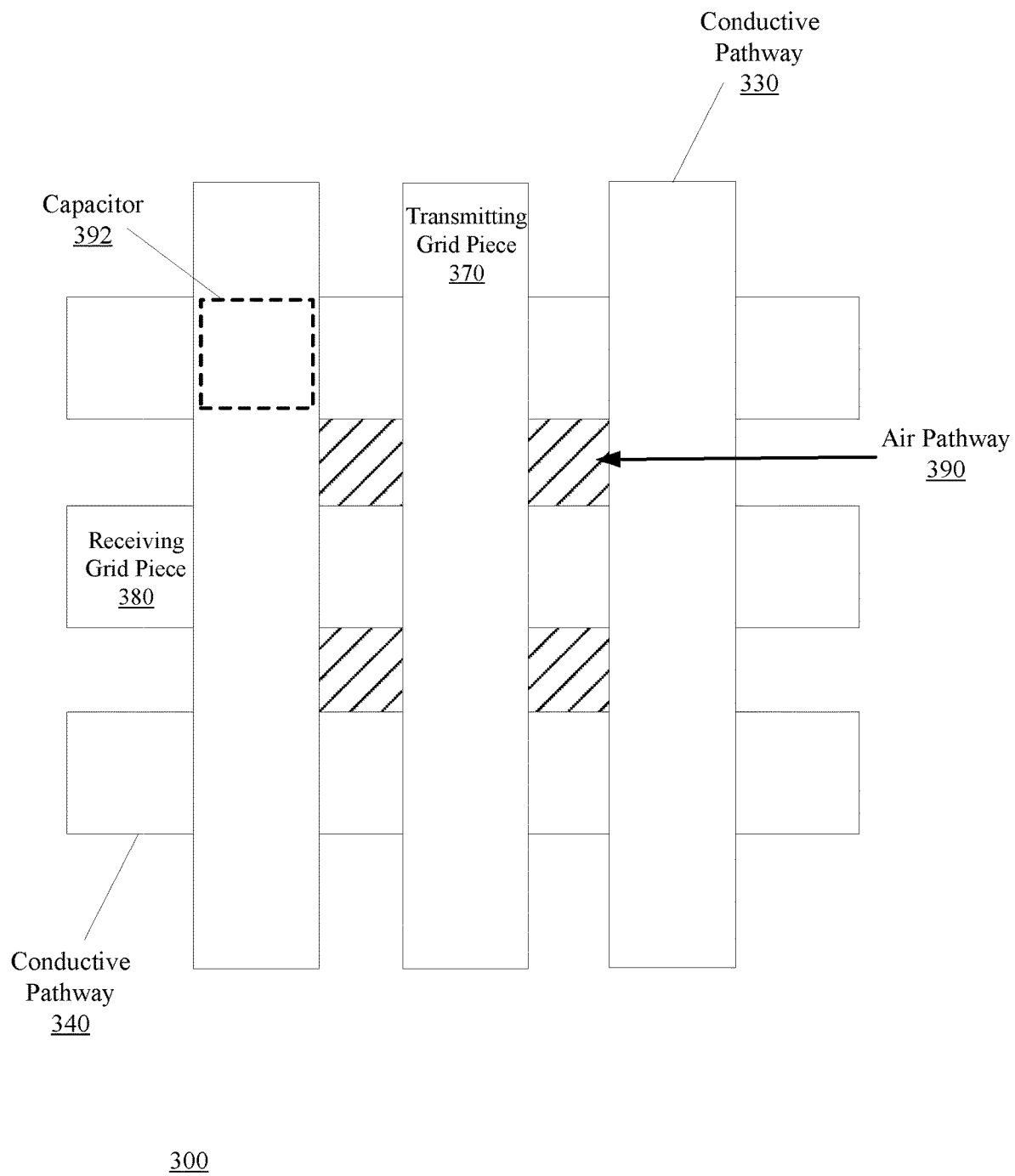
FIG. 3B is a conceptual diagram illustrating the top view of the sensor grid layer shown in FIG. 3A.

FIG. 3A is a conceptual diagram illustrating a cross-sectional view of an example sensor grid layer 300, in accordance with some embodiments. FIG. 3B is a conceptual diagram illustrating the top view of the sensor grid layer 300. The example configuration shown in FIGS. 3A and 3B is an air-permeable sensor grid layer 300 that promotes the airflow of an entire weight support device 110. The sensor grid layer 300 is an embodiment of the sensor grid layer 214 or the moisture sensor grid layer 228. Conventionally, capacitive grid sensors are produced by bonding conductive strips to a continuous elastomer, which serves as the physical substrate holding the conductive strips in place. This elastomer is non-permeable by design. When this style of the grid is combined with a dielectric material to form a capacitive pressure sensor, the impermeable elastomer substrate is present throughout the entire sensor grip area, rendering the sensor grid layer impermeable.

Referring to FIG. 3A, the air-permeable capacitive sensor grid layer 300 includes a first permeable substrate 310, a second permeable substrate 320, a first set of electrically conductive pathways 330, a second set of electrically conductive pathways 340, thermoplastic materials 350, and a dielectric layer 360. The first set of electrically conductive pathways 330 bonded to the first permeable substrate 310 may serve as the transmitting grid piece 370 that transmits electrical signals and the second set of the electrically conductive pathways 340 bonded to the second permeable substrate 320 may serve as the receiving grid piece 380 where attenuated electrical signals are detected. The transmitting grid piece 370 and the receiving grid piece 380 may be identical or substantially similar, except the receiving grid piece 380 is flipped and rotated 90 degrees so that the first set of electrically conductive pathways 330 are arranged in the longitudinal direction and the second set of electrically conductive pathways 340 are arranged in the lateral direction. The sublayers shown in FIG. 3A of the sensor grid layer 300 may simply be referred to as layers.

The first permeable substrate 310 and a second permeable substrate 320 may be formed from air permeable materials such as foam or meshes, or any materials or fabrics that largely do not obstruct airflow through the substrates. An example material may be an open-cell compressible thermoplastic polyurethane (TPU) elastomer. The first permeable substrate 310 and a second permeable substrate 320 may allow free airflow to basically the entire surface area of the substrates. The first permeable substrate 310 and a second permeable substrate 320 each carries a plurality of electrically conductive pathways and the conductive pathways may be securely coupled (e.g., bonded) to the substrate. In some embodiments, the substrates securely position the electrically conductive pathways to define the sensor grid. In addition, the substrates may also securely position the electrically conductive pathways that are impermeable to air to be spaced apart to define a plurality of air pathways 390 to create an air-permeable capacitive sensor grid. In one embodiment, the first permeable substrate 310 and a second permeable substrate 320 may have a moisture vapor transmission rate of at least 270 g/m²/24 h. In one embodiment, the first permeable substrate 310 and a second permeable substrate 320 may have a moisture vapor transmission rate of 1214 g/m²/24 h. Air permeability may be tested under ASTM E96—Standard Test Methods for Water Vapor Transmission of Materials.

The first set of electrically conductive pathways 330 and the second set of electrically conductive pathways 340 are formed from conductive materials such as metallic conductive strips or wires. Owing to the materials used, the electrically conductive pathways may be air impermeable. For example, the electrically conductive pathways may be individually encapsulated or otherwise covered by a thermoplastic material 350 that insulates the electrically conductive pathways. The thermoplastic material 350 may also be air impermeable. The first set of electrically conductive pathways 330 may be arranged in a first orientation and the second set of electrically conductive pathways 340 may be arranged in a second orientation that is different from the first orientation. The first and second sets of electrically conductive pathways 330, 340 cross over each other to form intersections that have a dielectric layer 360 sandwiched between the two conductive pathways, thereby forming a capacitor 392 at each intersection. Each capacitor 392 is a sensing point of the sensor grid layer 300 and the network of intersections form a matrix of sensing points that can generate different measures of capacitance across different areas of the weight support device. In some embodiments, the capacitance may be proportional to or otherwise correlated with the force and pressure exerted on the area as the pressure compresses the area of the sensor grid layer 300 and reduces the distances between the top conductive pathway and the bottom conductive pathway. In some embodiments, the capacitance may be proportional to or otherwise correlated with an amount of moisture on a surface (e.g., on a surface of the first permeable substrate 310) of the sensor grid layer 300.

The arrangement of the electrically conductive pathways that are in longitudinal and lateral directions shown in FIG. 3B is only an example configuration. In various embodiments, the first set of electrically conductive pathways 330 and the second set of electrically conductive pathways 340 may be arranged relative to each other in any suitable manners and directions, perpendicular or not, regularly or not, symmetrical or not. The electrically conductive pathways in each set may also be arranged in a manner that is different from the configuration shown in FIG. 3B, whether the electrically conductive pathways are straight or curved, branched or unbranched, evenly spaced or not, aligned parallelly or not, and with same orientation or not. For example, instead of having evenly distributed electrically conductive pathways so that the weight support device has roughly the same number of sensing points in various areas, in some embodiments the electrically conductive pathways may be spaced more densely in certain target areas so that the target areas have a higher number of sensing points compared to other peripheral areas.

Each electrically conductive pathway in the first set 330 and the second set 340 may be spaced apart from the neighboring electrically conductive pathways to create horizontal air pathways 394. The horizontal air pathways 394 created by the first set of electrically conductive pathways 330 and the horizontal air pathways (not shown) created by the second set of electrically conductive pathways 340 may be oriented differently due to the different orientations of the electrically conductive pathways in the first and second set. The intersections of the horizontal air pathways 394 form vertical air pathways 390. In some embodiments, the vertical air pathways 390 may contain only the permeable substrates 310 and 320 and the permeable dielectric layer 360. In some embodiments, in order to further promote the airflow in the vertical air pathways 390, the dielectric layer 360 may be cut out at the vertical air pathways 390. In some embodiment, to even further promote the airflow, the permeable substrates 310 and 320 may also be cut out at the vertical air pathways 390.

Each electrically conductive pathway may be individually encapsulated by a thermoplastic material 350. The thermoplastic material 350 may be formed from flexible, insulating, and dielectric materials that are preferably as thin as possible. For example, in some embodiment, the thermoplastic material 350 may be an elastomer such as urethane. Other thermoplastic elastomers (TPE) or thermoplastic polyurethanes (TPU) may also be possible. The thermoplastic material 350 provides insulation and protection to each electrically conductive pathway to prevent short circuit or cross talk of the conductive pathways. The thermoplastic material 350 also surrounds the conductive pathway and serves as a bonding medium to secure the conductive pathway to the permeable substrate 310 or 320. While other insulating materials may be used, the thermoplastic material 350 is used in the example shown in FIG. 3A so that the thermoplastic material 350 can be heat activated to be heat laminated and thermally bonded to the permeable substrate 310 or 320. In some embodiments, each electrically conductive pathway is individually encapsulated so that the encapsulated electrically conductive pathway can be spaced apart and form horizontal air pathways to promote the air permeability of the sensor grid layer 214.

The dielectric layer 360 is sandwiched between the transmitting grid piece 370 and the receiving grid piece 380. The dielectric layer 360 may be formed of a permeable material such as polyurethane foam so that air can pass through the layers of the weight support device. In some embodiments, both the dielectric layer 360 and the permeable substrates 310 and 320 may use the same types of materials, such as open-cell polyurethane foam.

An air-permeable sensor grid offers various advantages over conventional urethane laminated sensor grid. For example, an air-permeable sensor produces significantly less noise generated when layers around the sensor rub against the air-permeable grid. An air-permeable sensor grid also increases user comfort due to airflow through permeable grid layers. An air-permeable sensor grid also decreases heat retention from the reduction in urethane and increased permeability in the sensing layer. An air-permeable sensor grid further simplifies surface temperature and humidity monitoring. An air-permeable sensor grid also allows an integration of active cooling technologies for moisture and surface temperature control such as low air loss mattresses. For example, an active airflow source 396 (e.g., generated from the airflow system 120 in FIG. 1A) may direct air into inner layers of the sensor grid.

Example Sensor Grid Production Process

Figure 4A:
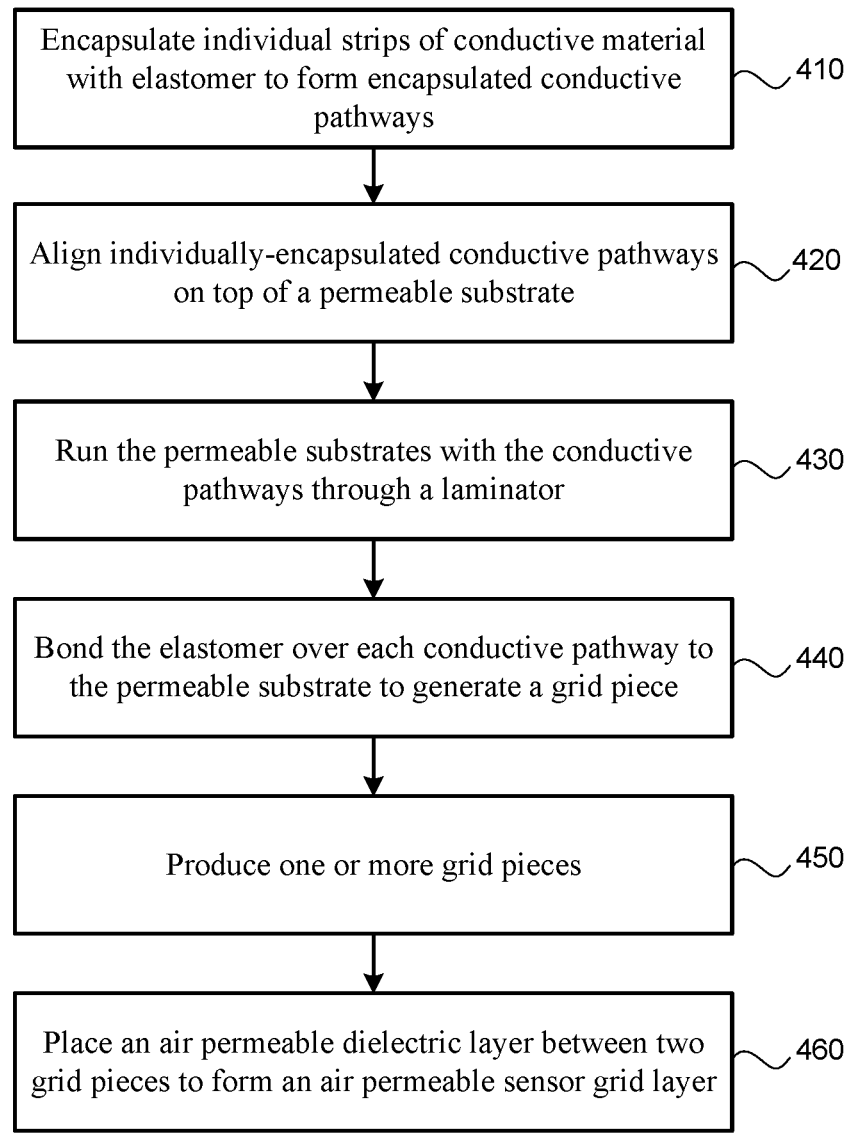
FIG. 4A is a flowchart depicting an example process for producing an air-permeable sensor grid layer, in accordance with some embodiments.
Figure 4B:
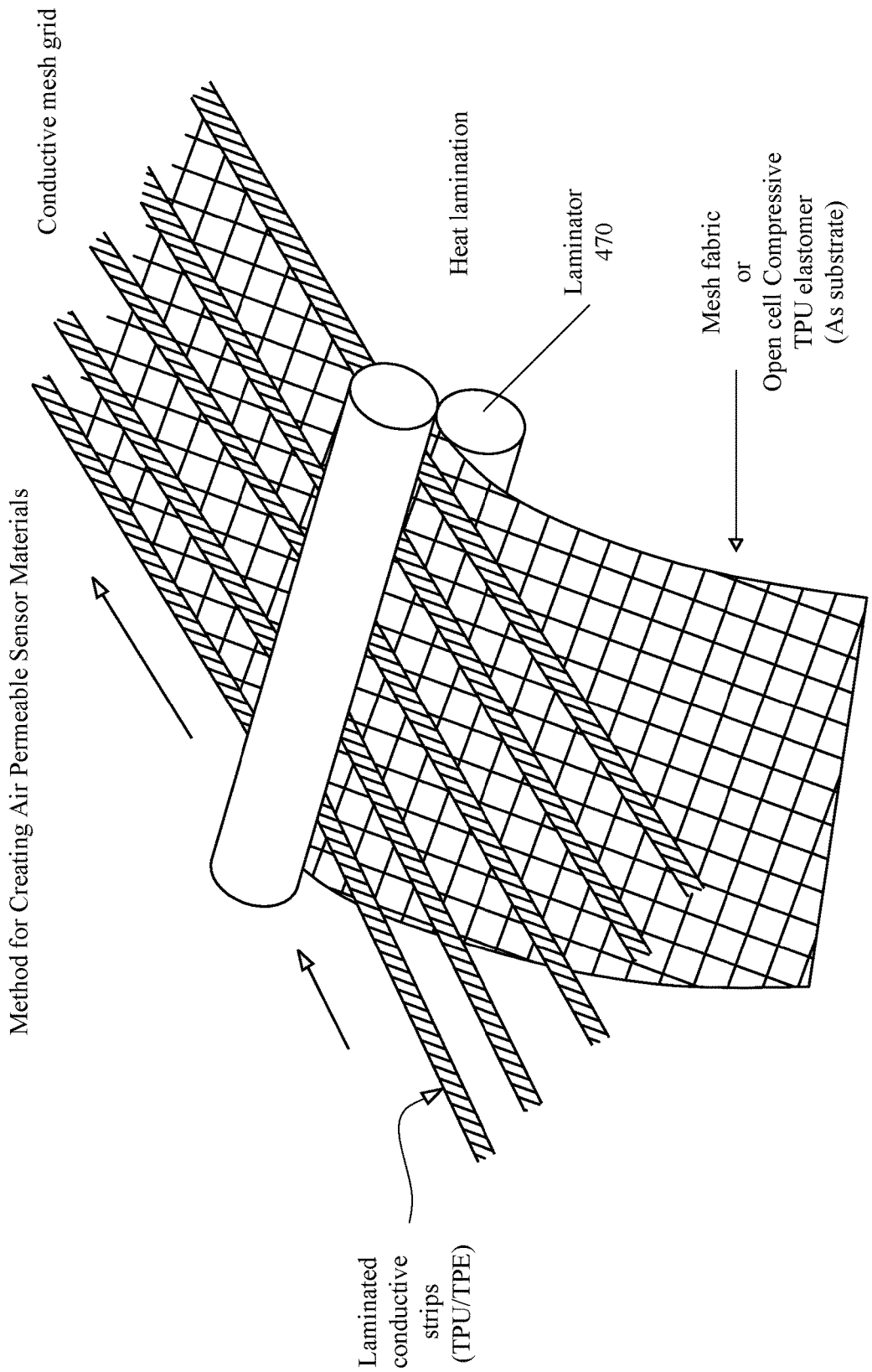
FIG. 4B illustrates an example lamination process, in accordance with some embodiments.

FIG. 4A is a flowchart depicting an example process 400 for producing an air-permeable sensor grid layer 300, in accordance with some embodiments. During the production process 400, individual strips of conductive material may be encapsulated 410 with a thermoplastic elastomer such as urethane to form encapsulated conductive pathways. The elastomer serves to physically and electrically isolate each conductive strip to form an individual conductive pathway. By individually encapsulating the conductive pathways in the elastomer, each conductive pathway is not physically connected to its neighboring conductive pathways with continuous elastomer. A series of individually-encapsulated conductive pathways may be aligned 420 on top of a permeable substrate material (e.g., foam or mesh). The permeable substrate (e.g., the permeable substrates 310 or 320) with the conductive pathways may run 430 through a laminator 470. FIG. 4B illustrates an example lamination process, in accordance with some embodiments. The elastomer over each conductive pathway is bonded 440 to the permeable substrate to generate a grid piece (e.g., the transmitting grid piece 370 or the receiving grid piece 380) where the strips are held in alignment (e.g., parallel alignment) and the gaps between strips allow airflow. The conductive pathways with the elastomer may be thermally bonded to the permeable substrate. Alternative bonding methods such as adhesive and pressure bonding may also be used. Two of such grid pieces may be produced 450 using the same or similar method. One of the grid pieces may be flipped and turned 90 degrees. An air-permeable dielectric layer may be placed 460 between the two grid pieces to form an air permeable sensor grid layer 300.

Permeable sensors built with the process 400 have the benefit of being more flexible than their traditional counterparts, as well as being much quieter during use. Traditional sensors must also be built with air handling in mind. To prevent air from becoming trapped between conductive grid layers and impacting capacitance, physical routes of airflow must be built into the sensor. Permeable sensors avoid this problem entirely as air can flow freely through all layers of the sensor. Also, the process 400 simplifies the production process. The permeable substrate 310 or 320 provides a platform to secure individual conductive pathways that need to be spaced apart to generate air pathways. The encapsulation of the conductive pathways provides a way to bond the metallic pathway to the air-permeable substrate.

Example Signal Processing

FIG. 5A is a conceptual diagram of a matrix 510 of sensor readings generated by a sensor grid layer 300, in accordance with some embodiments. The sensor grid layer 300 includes a plurality of sensing points. Each of the sensing points can generate a sensor reading such as a pressure reading or a surface moisture reading. The signals from each sensor grid layer 300 may generate a matrix 510 of sensor readings. The inset 520, which shows an enlarged area of the matrix 510, illustrates that each grid position that corresponds to a sensing point provides an individual sensor reading value. In some embodiments, the sensor mapping engine 142 of the computing server 140 may receive these sensor readings and generate one or more visual representations of the data. As shown in FIG. 5B, a conceptual diagram illustrates an example pressure heatmap 530 generated by a matrix of sensor readings, in accordance with some embodiments. The values of the sensor readings (e.g., the values in matrix 510) may be converted to various colors or greyscales to illustrate pressure distribution on the weight support device 110. For example, the pressure heatmap 530 shows a greyscale heatmap in which higher pressure values are associated with darker colors. Because the area of the weight support device 110 without the person should detect significantly less pressure than the area on which the person is currently positioned on, the area without the person is shown as white. A body outline 545 of the person may be detected based on the sensor readings by the sensor mapping engine 142 as described above. When the person moves by adjusting their position on the weight support device 110, the sensor grid layer 300 generates different sensor readings. The heatmap 530 and the outline 545 of the person are also changed as a result. In some embodiments, the heatmap 530 may also be in a color scheme. For example, low-pressure areas will be shown using cooler colors and high-pressure areas will be shown using warmer colors.

A computer (e.g., the computing server 140, the local computer 130, and the user device 160) may process the data from the sensor grid layer 300 and generate different results related to the person. The computer (e.g., via the machine learning engine 146) may use one or more machine learning models and other data processing techniques to deduce joint locations 540 of the person, a pose of the person, and movement of the person.

Data generated from the weight support device 110 allows a computer to intelligently identify selected areas of the body and extract bio-signals from certain target areas. Both the body and joint locations may be used to identify regions on the body which are then monitored to detect physiological signals. This identification procedure significantly reduces signal noise and allows for more accurate monitoring. For example, the rectangle 543 shown in the heatmap 530 demonstrates how a region of the body can be selected (lumbar) using the joint detection system (convolutional neural network with pre and post processing). This region can then be used to identify a bio-signal associated with the area of the body. For example, the respiration rate may be identified by locating the lumbar region of the body. Another example is temperature monitoring. The user's body outline 545 can be identified based on the sensor readings. The thermistors located within the user's body outline 545 can be used to monitor surface temperature of the weight support system 110 underneath the user's body (e.g., only activate the thermistors within the outline 545).

FIG. 5C is a conceptual diagram illustrating an example surface moisture heatmap 550 that is generated by a matrix of sensor readings, in accordance with some embodiments. The values of the sensor readings may be converted to various colors or greyscales to illustrate the surface moisture distribution on the weight support device 110. For example, the surface moisture heatmap 550 shows a greyscale heatmap in which higher levels of surface moisture are associated with darker colors. For example, greater amounts of surface moisture is detected on a region of the weight support device 110 that corresponds to region 555 of the heatmap 550 and little to no surface moisture is detected on a region of the weight support device 110 that corresponds to region 560 of the heatmap 550. In some embodiments, the heatmap 530 may also be in a color scheme. For example, low-moisture areas will be shown using cooler colors and high-moisture areas will be shown using warmer colors. In alternative embodiments, the sensor readings may correspond to a binary (yes/no) detection of surface moisture. With these embodiments, the heatmap 530 may include two colors (e.g., black and white, red and blue, etc.) for depicting areas with or without surface moisture present.

Example Pressure Injury Outcome Detection Processes

Figure 6A:
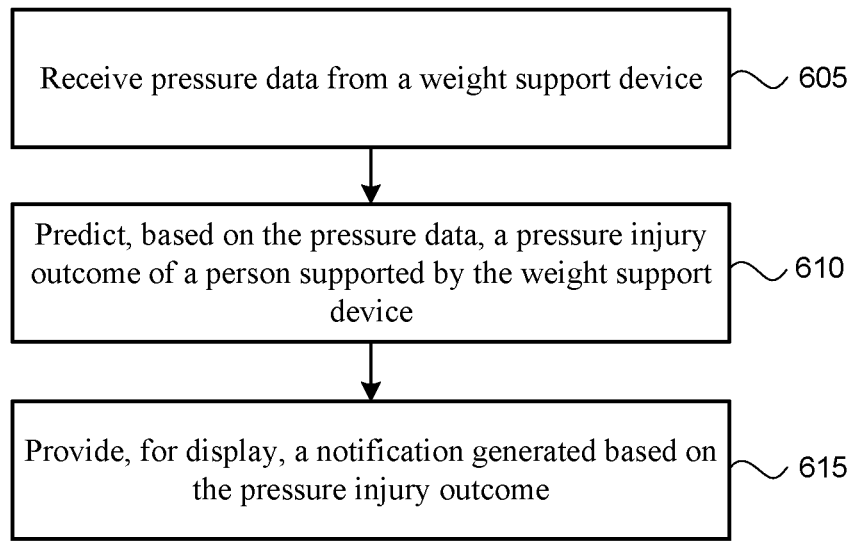
FIG. 6A is a flowchart depicting an example process for determining a pressure injury outcome, in accordance with some embodiments.

FIG. 6A is a flowchart depicting an example process 600 for determining a pressure injury outcome of a person supported by the weight support device 110, in accordance with some embodiments. A computer, which may be the computing server 140, the local computer 130, or the user device 160, may perform the process 600. Other entities may perform some or all of the steps in FIG. 6A in other embodiments. Embodiments may include different and/or additional steps or perform the steps in different orders.

The computer receives 610 pressure data from the weight support device 110. For example, the computer may receive the pressure data from the sensor grid layer 214 of the weight support device 100. The pressure data may be raw pressure data and include a time series of matrix readings similar to the matrix 510. The pressure data may also be processed data whose time series has been digitally filtered by various digital signal processing techniques such as a finite impulse response (FIR) filter, Gaussian filter, smoothing, etc. For each time instance, the pressure data may include two-dimensional data that correspond to the sensor grid of the weight support device 110. In some embodiments, the computer may also receive additional data such as surface moisture data, individual's vital data, temperature data, and other suitable data.

The computer predicts 620, based on the pressure data, the pressure injury outcome of the person supported by the weight support device 110. The prediction may also involve the use of other data such as surface moisture data. In some embodiments, the computer utilizes a rules-based (or heurstics-based approach) to predict the pressure injury outcome. In some embodiments, the computer inputs the pressure data into one or more machine leaning models (e.g., a convolutional neural network (CNN)) to predict the pressure injury outcome. The pressure injury outcome may include a risk of the person developing a pressure injury, an area of the person's body at risk of developing the pressure injury, and an amount of time that indicates when an adjustment of a positioning of the person is needed to avoid pressure injury. The determination of the pressure injury outcome may include using a machine learning model to identify, based on the pressure data, a visual representation of a body outline of the person with various joint locations of the person. The computer may in turn monitor pressures exerted on the joint locations or other locations of the person over time and continue to monitor the natural movement of the person, such as when the person is sleeping on the weight support system 110. The computer may monitor whether the pressure value of a particular part of the person's body exceeds a threshold value and the duration of the pressure value exceeding the threshold to determine whether a notification will need to be sent.

The computer provides 630, for display, a notification generated based on the pressure injury outcome. The notification may be displayed on the local computer 130, the user device 160, and/or the management device 170. The notification may include an alert or message to a user (e.g., a nurse) that the person supported by the weight support device 110 is at risk of developing a pressure injury. In some embodiments, the notification may include an alert or message to the user that the person support by the weight support device 110 is currently experiencing pressure on an area that should not experience pressure. The notification may also provide additional information, such as the area(s) of the person at risk of developing the pressure injury and/or when the positioning of the person should be adjusted to avoid any pressure injuries. The computer may provide, for display, a visual representation of the person and highlight the area(s) of the person at risk of developing pressure injury. The notification and visual representations are described in more detail in FIGS. 7A-7D.

The notifications may be routine or reactive. For example, some notifications may be periodically generated that includes pressure values and vital information of the individual's different body parts. Other notifications may be alerts that are sent when actions (such as turning the patient or warning of potential injury) are needed under certain conditions. Additionally or alternatively, the notification may include a recommendation to the healthcare provider or other caregiver associated with a recommended pose for the patient. The recommended pose may be based on tracked sensor data from one or more weight support devices 110 the patient has been supported by over the course of their treatment or hospital stay. For example, if an area of high pressure builds up on the patient's right shin, the computer recommends via the notification that the right shin should be adjusted so that the pressure is dispersed.

Figure 6B:
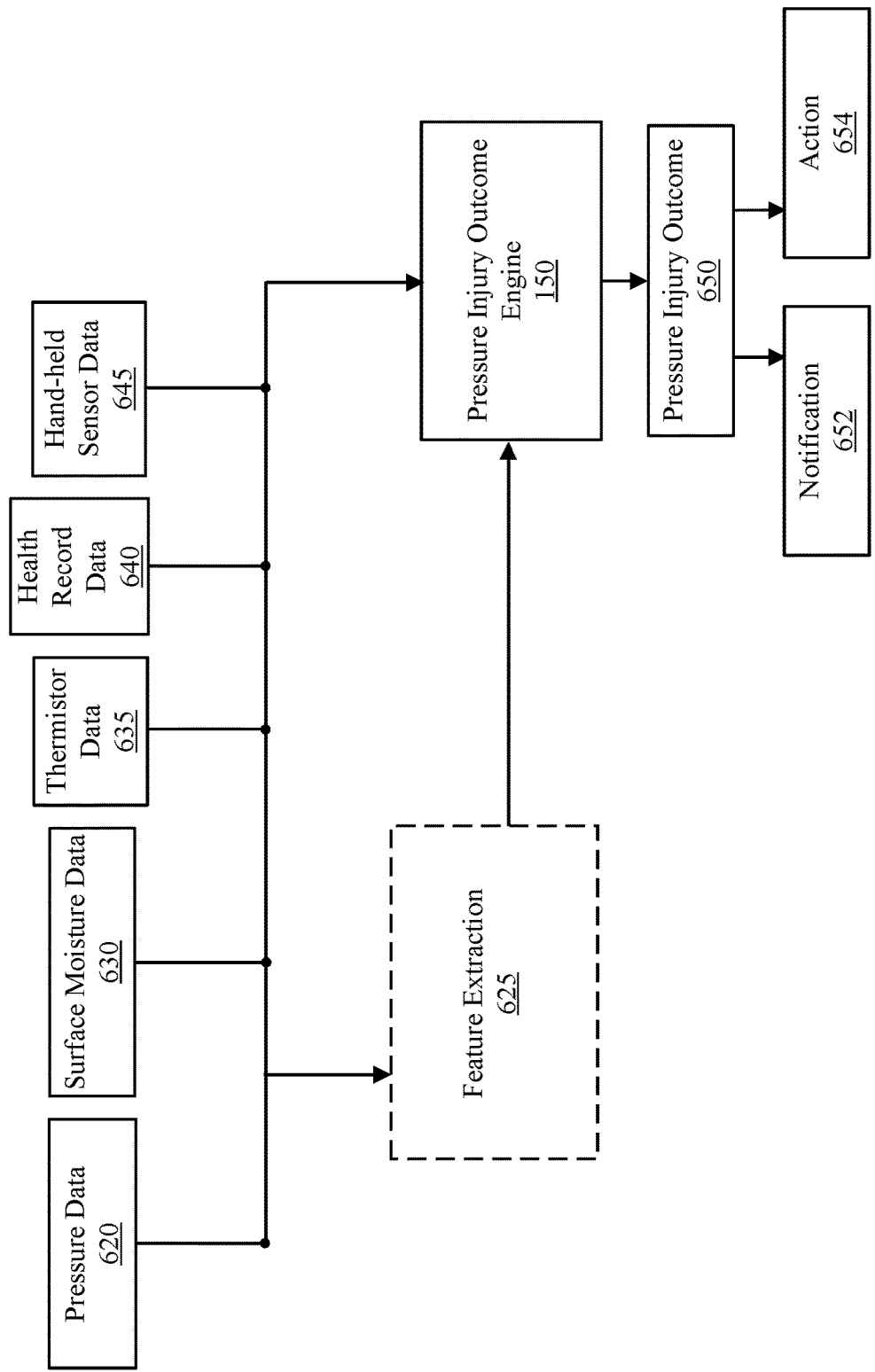
FIG. 6B is a block diagram illustrating an example algorithmic pipeline for predicting a pressure injury outcome, in accordance with some embodiments.

FIG. 6B is a block diagram illustrating an example algorithmic pipeline for predicting a pressure injury outcome 650 for a person, in accordance with some embodiments. The pipeline includes inputs, a feature extraction stage 625, and outputs of the pipeline.

The inputs may include pressure data 620, surface moisture data 630, thermistor data 635 about surface temperature, health record data 640, and hand-held sensor data 645. The pressure data 620, the surface moisture data 630, and the thermistor data 635 include raw sensor readings currently being collected by a weight support device (e.g., the weight support device 110) as described above. The health record data 640 is stored in a database or data store (e.g., the data store 155) and may include information about the person, such as an age, mobility information, nutrition information, pre-existing skin conditions, incontinent issues, medical history, current medications, one or more areas of the person that are to avoid pressure, etc. The health record data 640 may additionally include previously collected pressure data, surface moisture data, and/or surface temperature data for the person. For example, the health record data 640 may include aggregated pressure data, aggregated surface moisture data, and/or aggregated surface temperature data collected by one or more weight support devices the person has come into contact with. In some embodiments, the health record data 640 includes historic hand-held sensor data. The hand-held sensor data 645 include sensor readings currently being collected by a hand-held sensor (e.g., the hand-held sensor 115).

In some embodiments, the inputs are provided directly to the pressure injury outcome engine 150. In some embodiments, the inputs are provided to the feature extraction stage 625. The feature extraction stage 625 may perform operations discussed above in reference to the sensor mapping engine 142, the machine vision engine 144, the machine learning engine 146, and the vital analysis engine 148. The feature extraction stage 625 extracts particular features which may be input into the pressure injury outcome engine 150. The extracted features may include various position data 660 associated with the person (e.g., a pose of the person, a position of the person, joint locations of the person, and movement data), pressure data at particular body part locations with respect to the person, determined one or more areas of high shear at particular body part locations with respect to the person, surface moisture of weight support device at particular body part locations with respect to the person, surface temperature of weight support device at particular body part locations with respect to the person, and risk factors of the person that may contribute to developing a pressure injury.

The feature extraction stage 625 may analyze the inputs to determine one or more risk factors of the person that may contribute the person developing a pressure injury. Some example methods for determining risk factors are discussed in U.S. Pat. No. 9,320,665, patented on Apr. 26, 2016, entitled "Risk Modeling for Pressure Ulcer Formation," which is incorporated by reference herein for all purposes. In some embodiments, the feature extraction stage 625 may analyze the health record data 640 to determine risk factors.

For example, information related to age, mobility, nutrition, existing skin conditions, incontinency issues, medications, and medical history may be determined risk factors. Patient movement, accumulated pressure, surface moisture, humidity, shear, and other patient risk factors are key influencers in pressure injury development. Adding environmental moisture/humidity sensing would be an additional benefit, and surface temperature sensing. Thus, possible risk factors may include (1) pressure over time, (2) sensory perception, (3) moisture, (4) patient activity, (5) patient mobility, (6) patient nutrition, (7) friction and shear, (8) patient body type and weight, (9) patient skin condition, (10) patient sex and age, (11) patient incontinence issue, (12) patient tissue malnutrition, (13) patient neurological deficit, (14) patient major surgery or trauma, (15) general physical condition, (16) patient mental state, or another suitable risk factor, or any combination thereof. The pressure injury outcome engine 150 tracks and factors in the risk factors to predict if patient intervention is needed (e.g., if a patient's positioning should be adjusted to avoid pressure injury).

The feature extraction stage 625 may analyze the inputs to determine various position data 660 associated with the person by utilizing machine learning models discussed in detail with reference to FIG. 6C. The position data 660 (e.g., the joint locations 668) provides a two-dimensional and/or three-dimensional model of the person's body. In some embodiments, the model is a kinematic human body model.

The feature extraction stage 625 may analyze the inputs to determine areas of overlap. For example, the feature extraction stage 625 may utilize a body outline and/or the model of the person as discussed above and analyze the pressure data 620, the surface moisture data 630, and the thermistor data 635 to find particular locations where the person's body outline and/or model overlaps with areas of high pressure, with detected surface moisture, and/or high surface temperature. Areas of overlap and the corresponding pressure data 620, surface moisture data 630, and thermistor data 635 may be weighted by the feature extraction stage 625 to be of greater importance in the determination of the pressure injury outcome 650 of the person. As such, pressure data at particular body part locations with respect to the person, surface moisture of the weight support device at particular body part locations with respect to the person, and/or surface temperature of the weight support device at particular body part locations with respect to the person, where the particular body part locations are the same, are weighted more heavily than pressure data, surface moisture data, and/or surface temperature data at other locations. In some embodiments, the feature extraction stage 625 may weight areas of overlap higher based on one or more timing parameters. The timing parameters may include how long the areas have overlapped and/or how long the areas have overlapped over a specified time interval.

The pressure injury outcome engine 150 determines the pressure injury outcome 650 for the person. In some embodiments, the pressure injury outcome engine 150 utilizes a rules-based approach and/or a machine learning model (e.g., a CNN) to determine the pressure injury outcome 650. For example, the inputs may be directly fed into the machine learning model. In another example, the extracted features from the feature extraction stage 625 are fed into the machine learning model. In some embodiments, the machine learning model may be trained on a combination of historical input data and known pressure injury outcomes (e.g., historical patient data).

Additionally or alternatively, the hand-held sensor (and its corresponding hand held sensor data 645) can inform a user (e.g., a healthcare professional) of the pressure injury outcome 650 without applying a rules-based approach and/or a machine learning model to the hand held sensor data 645.

The pressure injury outcome 650 as described above may include a risk of the person developing a pressure injury, an area of the person's body at risk of developing the pressure injury, and an amount of time that indicates when an adjustment of a positioning of the person is needed to avoid pressure injury. The pressure injury outcome 650 may be communicated to a user (e.g., a healthcare professional, a caregiver, the person, etc.) via a notification 652. For example, the notification 652 may be displayed in a graphical user interface (e.g., the interface 165). In some embodiments, the notification 652 may be an audible message played for the user. The notification 652 may provide instructions to the user about when and how to adjust the position of the person to avoid pressure injury. The notification 652 may provide instruction to the user to use a hand-held sensor to collect additional information, such as an amount of moisture under the person's skin in particular body part locations. Based on the pressure injury outcome 650, an action 654 may take place. For example, instructions may be provided to the weight support device to adjust the positioning of the person. The weight support device may do so by inflating or deflating one or more bladders on the surface of the weight support device and/or by operating one or more servo motors that adjust the surface of the weight support device. In another example, the user may adjust the positioning of the person.

Figure 6C:
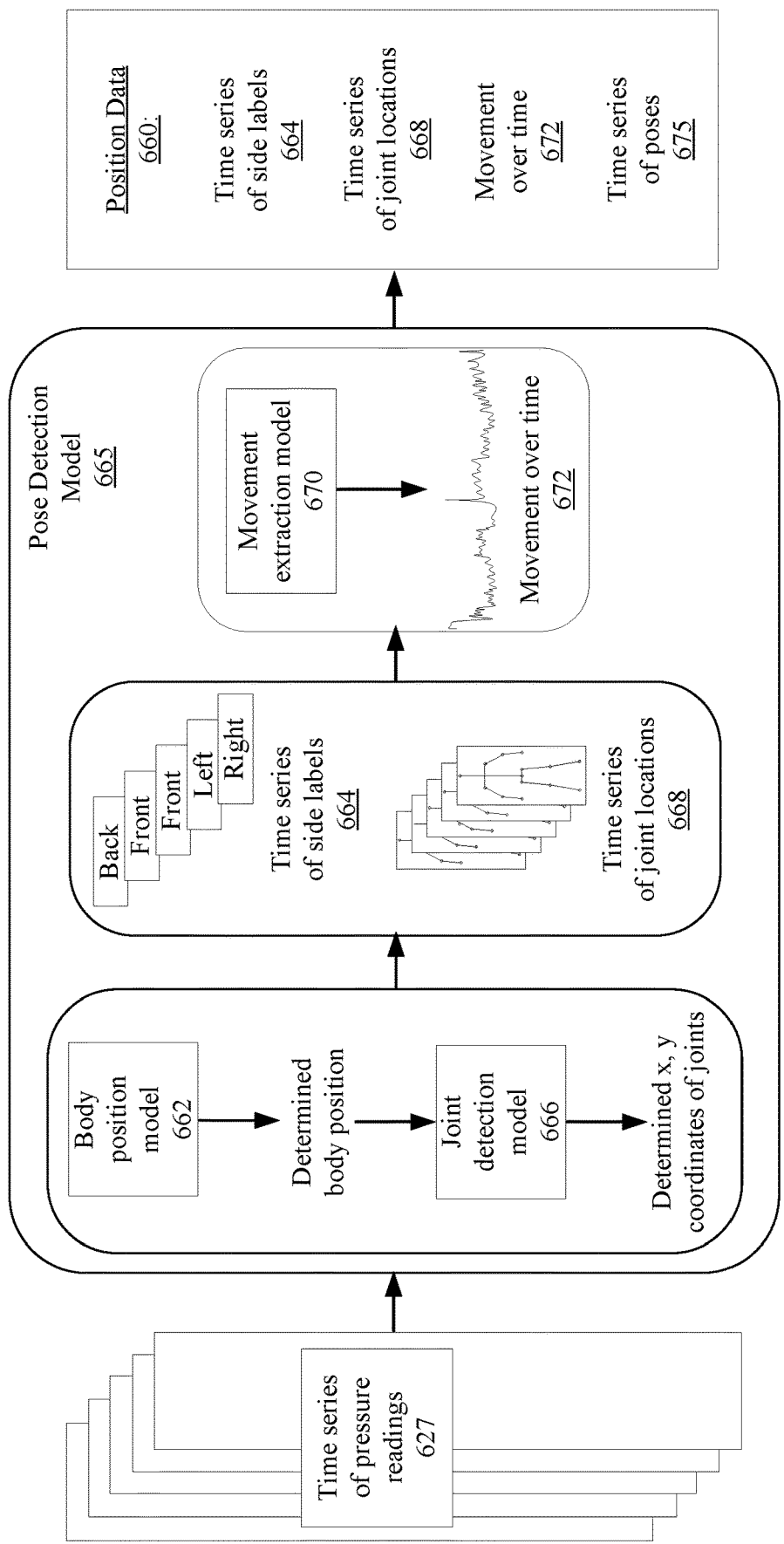
FIG. 6C is a conceptual diagram showing a pipeline of generating various position data related to a person supported by a weight support device, in accordance with some embodiments.

FIG. 6C is a conceptual diagram showing the pipeline of generating various position data 660 related to a person supported by a weight support device 110, in accordance with some embodiments. The computer may use a pose detection model 665 to determine the position data 660. The pose detection model 665 may receive a time series of pressure readings 627 (e.g., a time series of pressure data) and perform various analyses on the pressure readings 627. The analyses are related to the person's pose(s). The pose of the person may include some or all of the position data 660 for a single instance in time including joint location data and a side label. A time series of poses 675 may include some or all of the position data 660 for the time series (e.g., several instances in time over a time interval) including a time series of side labels 664, a time series of joint locations 668, and movement over time 672.

For example, the pose detection model 665 may include a body position model 662, which may be a machine learning model that generates a side label of the person given a particular instance in time or a time series of side labels 664 of the person given the time series. The computer may input the pressure sensor data to the body position model 662 to determine the side label(s) 664. The side label may determine whether a person is positioned on the left side, on the right side, on the front side, or on the backside. In one embodiment, the side label may include prone, supine, left side, right side, sitting, and sitting on the edge.

The computer may use a joint detection model 666 in the pose detection model 665. The joint detection model 666 may be a CNN that receives the pressure readings and identifies an outline (e.g., a body outline) and certain target joints of the persons. Depending on the model, there can be a predetermined number of identified target joints (such as 14). The target joints allow the computer to model the pose of the person similar to a stick figure. The CNN may output the joint locations 668 as two-dimensional coordinates (or three-dimensional coordinates) and a confidence probability between 0 and 1 for each joint location. The computer may then generate a skeleton of the user and determine the 2D spatial coordinates for the joints (e.g., the 14 joints) along with their probability. The example 14 joints may be hip, effector head, right shoulder, right forearm, right hand, left shoulder, left forearm, left hand, right thigh, right shin, right foot, left thigh, left shin, and left foot.

The computer may use a movement extraction model 670 to generate the body movements 672 of the person. Movement over time can be decomposed into the movement of specific body parts or joints over time given the information provided by the CNN. The body movements 672 may detect the magnitudes of the movement of the person over time.

In various embodiments, the body position model 662, the joint detection model 666, and the movement extraction model 670 of the pose detection model 665 may utilize a same machine learning model or separate machine learning models. For example, in one embodiment, a CNN can be trained to generate body position labels such as side labels 664, joint locations 668, and body movements 672 over time together using the time series of pressure readings 627. To determine a pose of the person, the computer may arrange, for a particular instance in time, the pressure readings as a matrix of pressure data. The computer may input the matrix of pressure data to a CNN for a particular pose at the particular instance in time. The computer may generate a time series of poses 675 for the time series of pressure readings 627 using the CNN. In some embodiments, the body position model 662, the joint detection model 666, and the movement extraction model 670 may be separate machine learning models that are specialized in generating certain types of position data 660. The CNNs may be trained on a combination of 2D matrices of pressure values and 3D motion-captured body data to generate the side labels 664, joint locations 668, and/or the body movements 672.

Figure 6D:
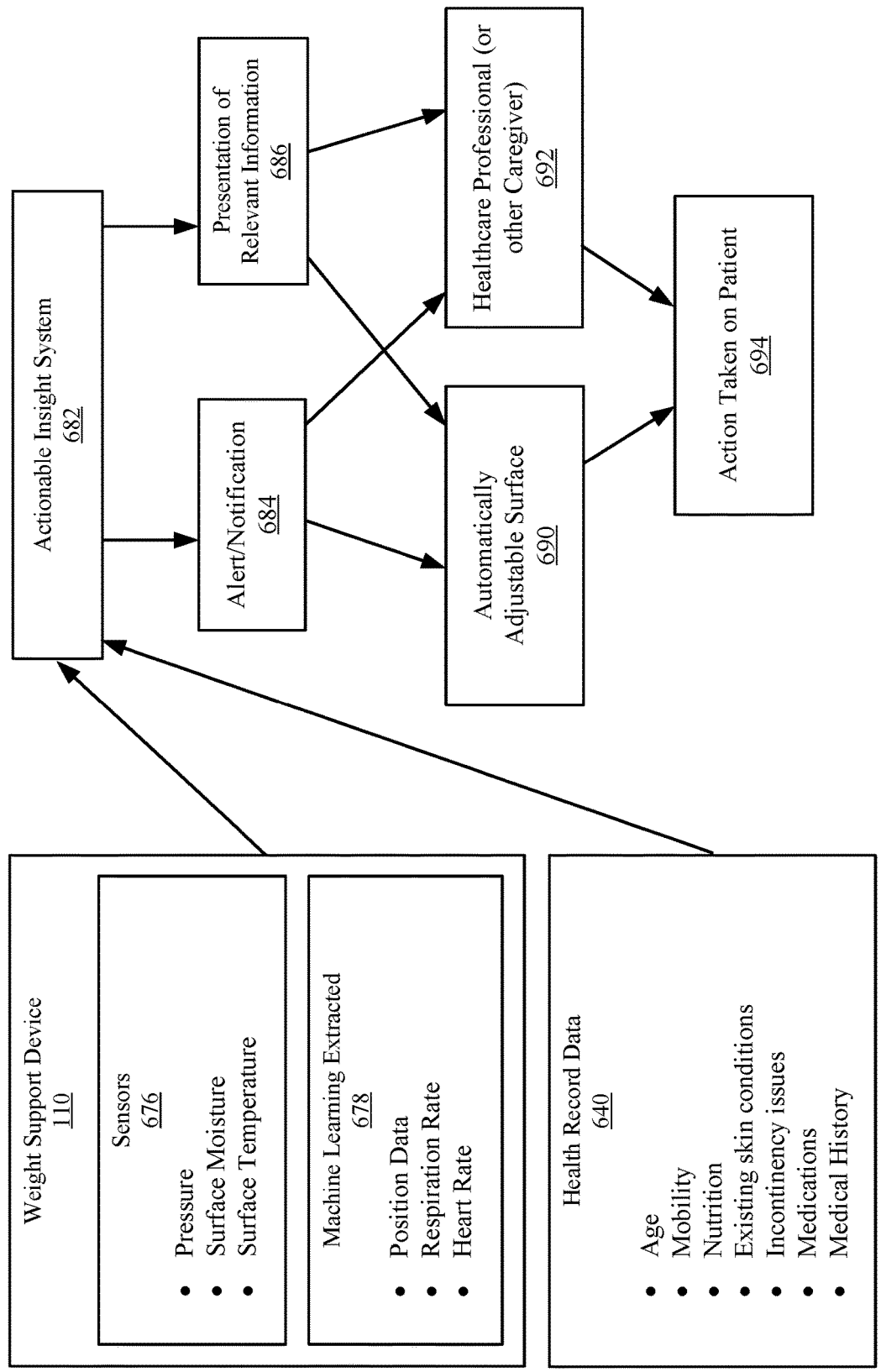
FIG. 6D is a block diagram illustrating an example system for monitoring a patient for pressure injury, in accordance with some embodiments.

FIG. 6D is a block diagram illustrating an example system 680 for monitoring a patient for pressure injury, in accordance with some embodiments. The system 680 may combine information from the weight support device 110 including sensors 676 and machine learning extracted information 678 for sending to an actionable insight system 682. For example, the sensors 676 measure data to be sent to the actionable insight system 682 which includes data from one or more pressure sensing elements, one or more surface moisture sensing elements, and/or one or more thermistors. The machine learning extracted information 678 to be sent to the actionable insight system 682 may include position data (e.g., position data 660 as described in FIG. 6C), a respiration rate, and/or a heart rate. Additionally, health record data 640 may be provided to the actionable insight system 682 and may include a patient's age, mobility, nutrition, existing conditions, incontinency issues, medications, medical history, any other suitable patient health record data 640, or any combination thereof. In some embodiments, the health record data 640 may include one or more pressure injury risk factors that can provide actionable insights to a healthcare professional.

The actionable insight system 682 may be an embodiment of the cloud actionable insight system 185 as described in FIG. 1B. The actionable insight system 682 analyzes all the information provided by the weight support device 110 and/or the health record data 640 to track the patient's condition on the weight support device 110 and provide actionable insights through alerts and/or notifications 684 and a presentation 686 of relevant information. The alerts/notifications 684 and/or presentation 686 of relevant information may be provided to an automatically adjustable surface 690 (e.g., a surface of the weight support device 110) and/or a healthcare professional 692 (e.g., via an interface 165 of a local computer 130). The alerts/notifications 684 are embodiments of the notification 652 as described in FIG. 6A. The presentation of relevant information 686 may include a visual representation of the patient currently supported by the weight support device 110 that highlights areas at risk of pressure injury. The presentation of relevant information 686 including visual representations is discussed in detail with reference to FIGS. 7A-7D. The automatically adjustable surface 690 and/or the healthcare professional 692 may adjust a positioning of the patient to mitigate the risk of the patient in developing a pressure injury. Thus, by adjusting the positioning of the patient an action 694 is taken on the patient to offload any body parts of the patient determined to be at risk.

Example Graphical User Interfaces

Figure 7A:
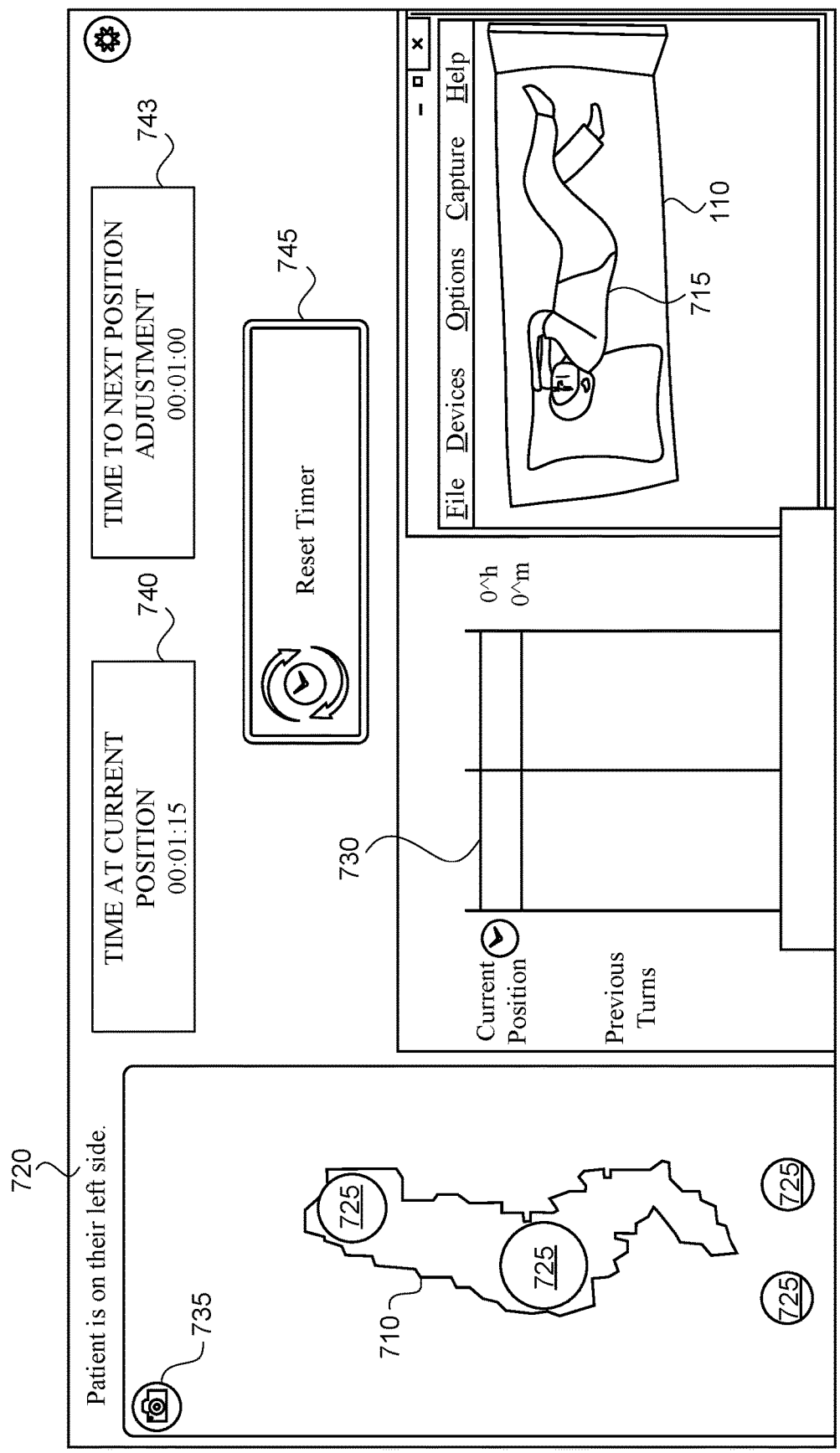
FIG. 7A is a conceptual diagram illustrating an example graphical user interface, in accordance with some embodiments.

FIG. 7A is a conceptual diagram illustrating an example graphical user interface 700, in accordance with some embodiments.

A computer (e.g., the local computer 130, the user device 160, and/or the management device 170) can display the graphical user interface (GUI) 700 that includes a heatmap 710 corresponding to a person 715 supported by a weight support device 110. The heatmap 710 may depict pressure data for the person 715, surface moisture data of the weight support device 110, surface temperature data of the person 715 and/or weight support device 110, area(s) of the person 710 at risk of a pressure injury, or any combination thereof. The GUI 710 may be an example of the interface 165 discussed in FIG. 1A. At a particular instance in time, the GUI 700 may display information related to the positioning (e.g., related to a pose 675) of the person 715, such as a side label 720. The GUI 700 may also display one or more symbols (e.g., circles 725 of different sizes, colors, etc.) that are used to represent specific areas of the heatmap 710. The specific areas may include body parts (e.g., joint locations), areas of surface moisture, areas of high surface temperature, areas of the person 715 at risk of developing pressure injury, or any combination thereof, detected by the computer. For example, in the example GUI 700, the circles 725 represent the areas of the person 715 at risk of developing pressure injury.

The GUI 700 may also include a time progress tracker 730 that tracks the poses and positions of the person 715 over time. The time progress tracker 730 may display turns and other position adjustments of the person 715 as a timeline. The time progress track 730 may also be interactive. For example, a user (e.g., the person 715 or a healthcare provider) may rewind to a particular time instance and the heatmap 710 will depict various information about the person 715 and the weight support device 110 at the particular time instance. The user may also capture the heatmap 710 using button 735.

The circles 725 may display different colors that represent various levels of pressure, surface moisture, surface temperature, and/or risk of developing pressure injury for a particular area or body part of the person 715. For example, the GUI 700 may provide various settings for the user to specify one or more threshold values for a circle 725 to change color. For example, a circle 725 may be in a first color (e.g., yellow) for a certain amount of pressure and may turn to a second color (e.g., red) if the amount of pressure detected at the body part exceeds a threshold pressure amount. In another example, a circle 725 may be in a first color (e.g., orange) for a certain amount of pressure detected at the body part and may turn to a second color (e.g., red) if surface moisture is detected at a same location as the body part. In some embodiments, the change of color may also be used to indicate other conditions, such as the particular body part is at greater risk of developing a pressure injury due to the area having been under pressure for a prolonged period of time (e.g., greater than a threshold amount of time), experiencing surface moisture for a prolonged period of time (e.g., greater than a threshold amount of time), experiencing high surface temperatures for a prolonged period of time (e.g., greater than a threshold temperature for greater than a threshold amount of time), or any combination thereof.

In some embodiments (not shown), the circles 725 may provide additional details other than simply designated specific areas (e.g., body parts) of the person 715. For example, in some embodiments, a circle 725 may include information displayed within the circle 725 or adjacent to the circle 725. In other embodiments, the circle 725 may be a link or other type of interface element that when selected by a user causes information to be displayed at a different location within the GUI 700. The information may include a countdown time until the corresponding body part of the person 715 may develop a pressure injury, a time when the corresponding body part may develop the pressure injury, a percentage (e.g., a percentage of progress until the pressure injury may occur), another suitable designation of timing of the pressure injury occurring, or some combination thereof. Additionally or alternatively, the circles 725 may provide information about accumulated pressure injury outcomes for corresponding body parts over a specified time interval (e.g., 2 hours, 6 hours, 12 hours, 24 hours, etc.). Depending on how and when the person's positioning is adjusted, certain body part(s) may have been at risk of developing a pressure injury at various times over the specified time interval. For each circle 725, information about accumulated pressure injury outcomes may include an amount of accumulated time the corresponding body part was at risk of developing a pressure injury over the specified time interval, how often the body part was at risk of developing the pressure injury over the specified time interval, and/or a magnitude of risk the body part has experienced over the specified time interval. The magnitude of risk may be a number quantifying how often and how long a certain body part has been at risk of developing a pressure injury. For example, the magnitude of risk may be a number from 1 to 10 with 10 being associated with a body part that has experienced greater risk and 1 being associated with a body part that has experienced less risk.

The computer monitors an amount of time the person 715 is positioned with a particular pose, such as on a particular side. The computer may display this amount of time in a timer 740 in the GUI 700. The computer may compare this amount of time displayed in the timer 740 to a maximum amount of time the person 715 should be positioned in the particular pose before the person 715 is at risk of developing a pressure injury as determined by the computer server 140. The GUI 700 may display a countdown timer 743 to keep track of a difference between the maximum amount of time and the amount of time the person 715 has maintained their current positioning or pose. The countdown timer 743 may inform the healthcare provider or caregiver when the positioning of the person 715 should be adjusted to avoid pressure injury. The computer may inform the healthcare professional and/or other caregiver via an alert or notification prior to the countdown timer 743 reaching zero that remedial measures are recommended. The remedial measures (e.g., adjusting the positioning of the patient) can take place in advance of any pressure injury taking place.

The computer may determine when the positioning of the person 715 is adjusted. For example, if the pressure data of the person 715 has altered and/or the areas (e.g., the circles 725) have updated, the positioning of the person 715 has been adjusted. The computer may automatically reset the timer 740 and the countdown timer 743. In some embodiments, the computer may automatically reset any times associated with each circle 725 (e.g., any countdown times, percentages, or other times). The computer may record a time the adjustment took place in the system memory. In some embodiments, a button 745 may also be used to reset either or both the timer 740 and the countdown timer 743 manually such as by a healthcare provider. The GUI 700 may display a visual warning (e.g., a notification, a message, etc.) to the person 715 or user that the countdown timer 743 is approaching zero and/or if the countdown timer 743 passes zero. In some embodiments, the computer may issue an audible warning to the person 715 or user that the positioning of the person 715 needs to be adjusted. The computer may generate a report that keeps track of the positioning of the person 715, time between adjustments, heatmaps 710, etc. that can be reviewed in a software application and/or stored in the person's health record in the data store 155.

In some embodiments, the GUI 700 may display additional information about the person 715. In some embodiments, the GUI 700 may display a visual representation (e.g., a generic body outline) of the person 715. For example, as illustrated in FIG. 7C, the GUI 700 may present a visual representation of the person 715 with certain body parts labeled with an amount of time until a pressure injury may occur at that particular body part. In some embodiments, the GUI 700 may display a graph, table, or other type of chart indicating a turn sequence for the person 715. For example, as illustrated in FIG. 7D, the GUI 700 may present a turn sequence for the person 715 that tracks position adjustments of the person 715 that occur on-time and/or that are overdue when compared to the pressure injury outcome (s) for that person 715.

Figure 7B:
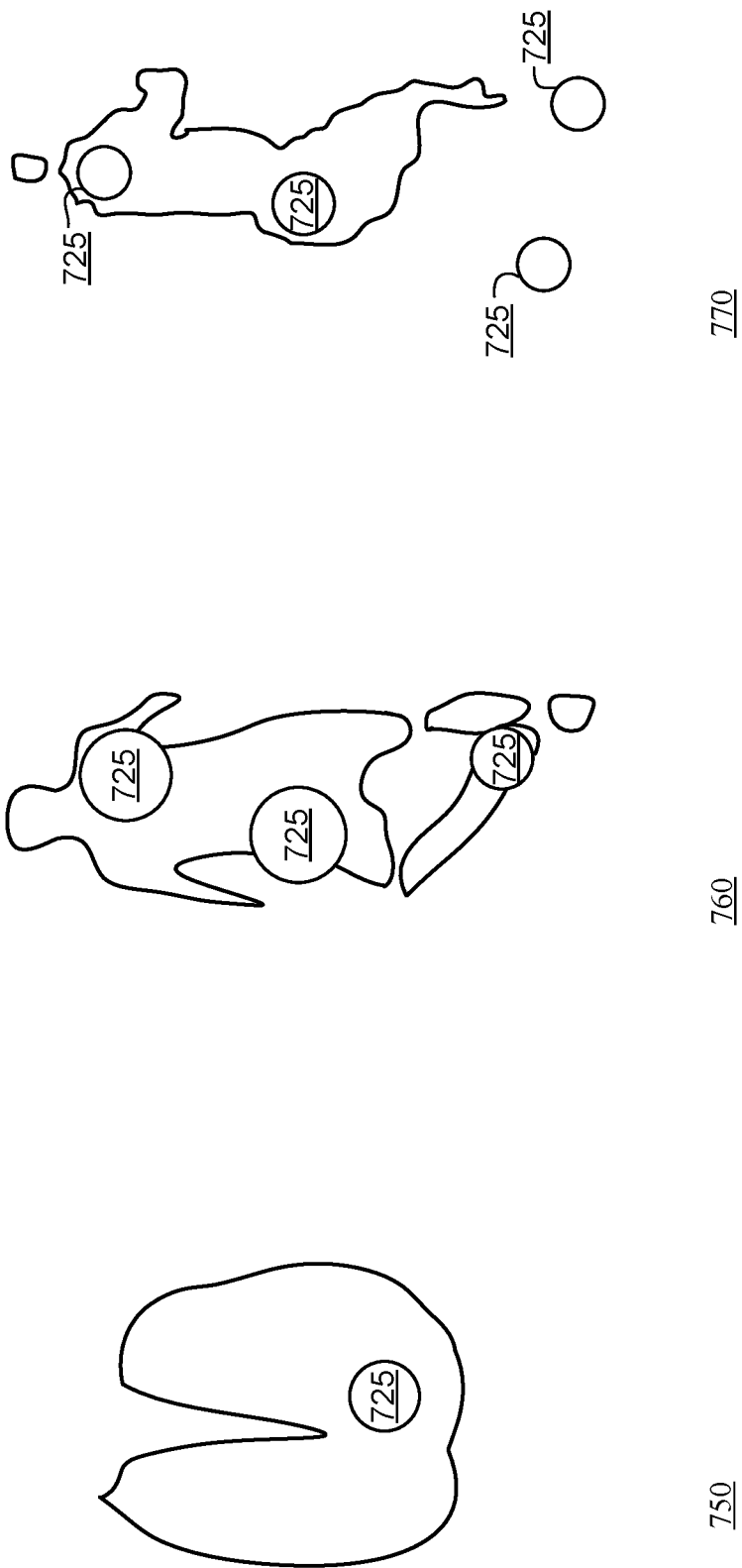
FIG. 7B is a conceptual diagram illustrating several example heatmaps, in accordance with some embodiments.
Figure 7C:
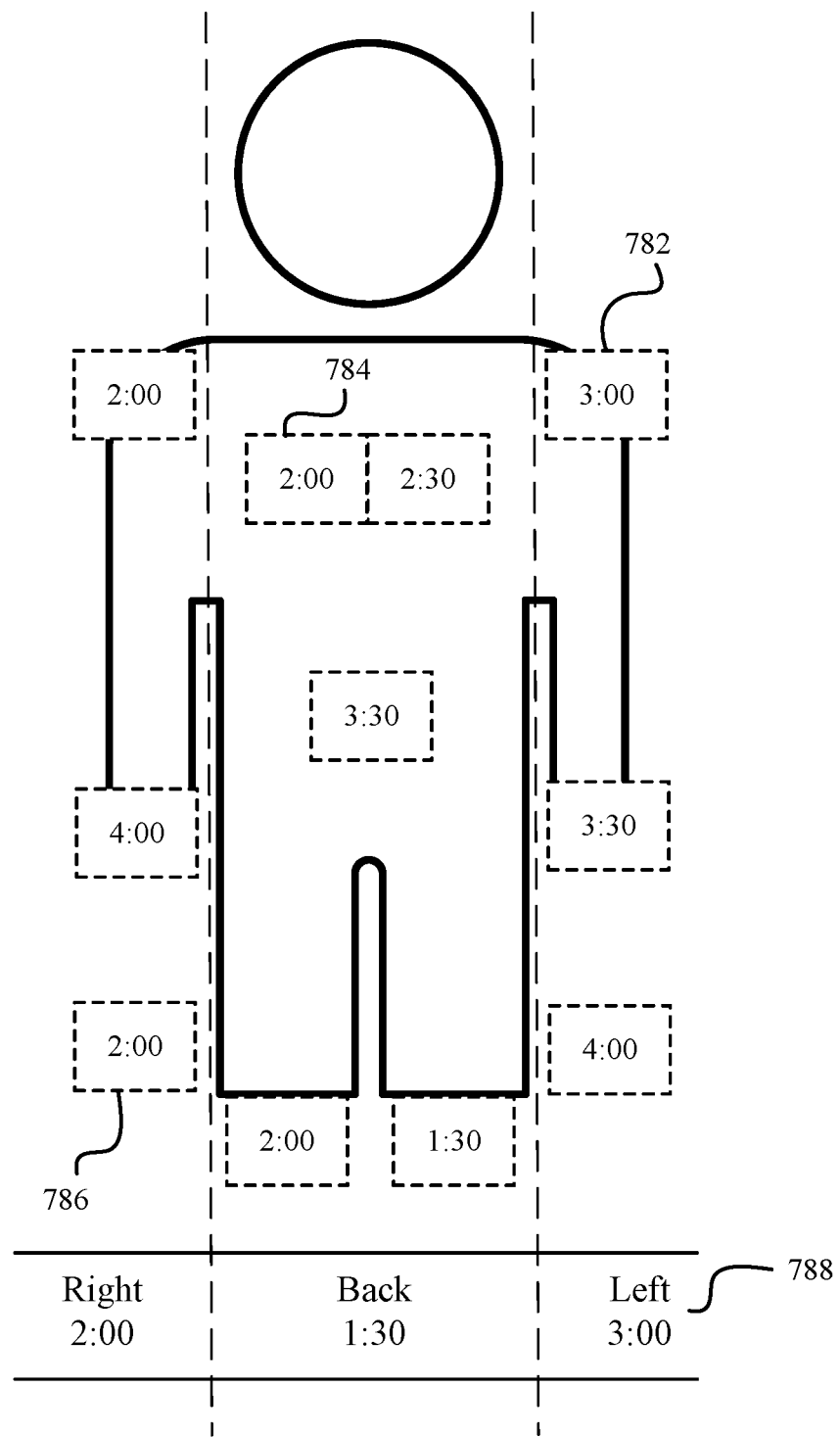
FIG. 7C is a conceptual diagram illustrating an example visual representation, in accordance with some embodiments.
Figure 7D:
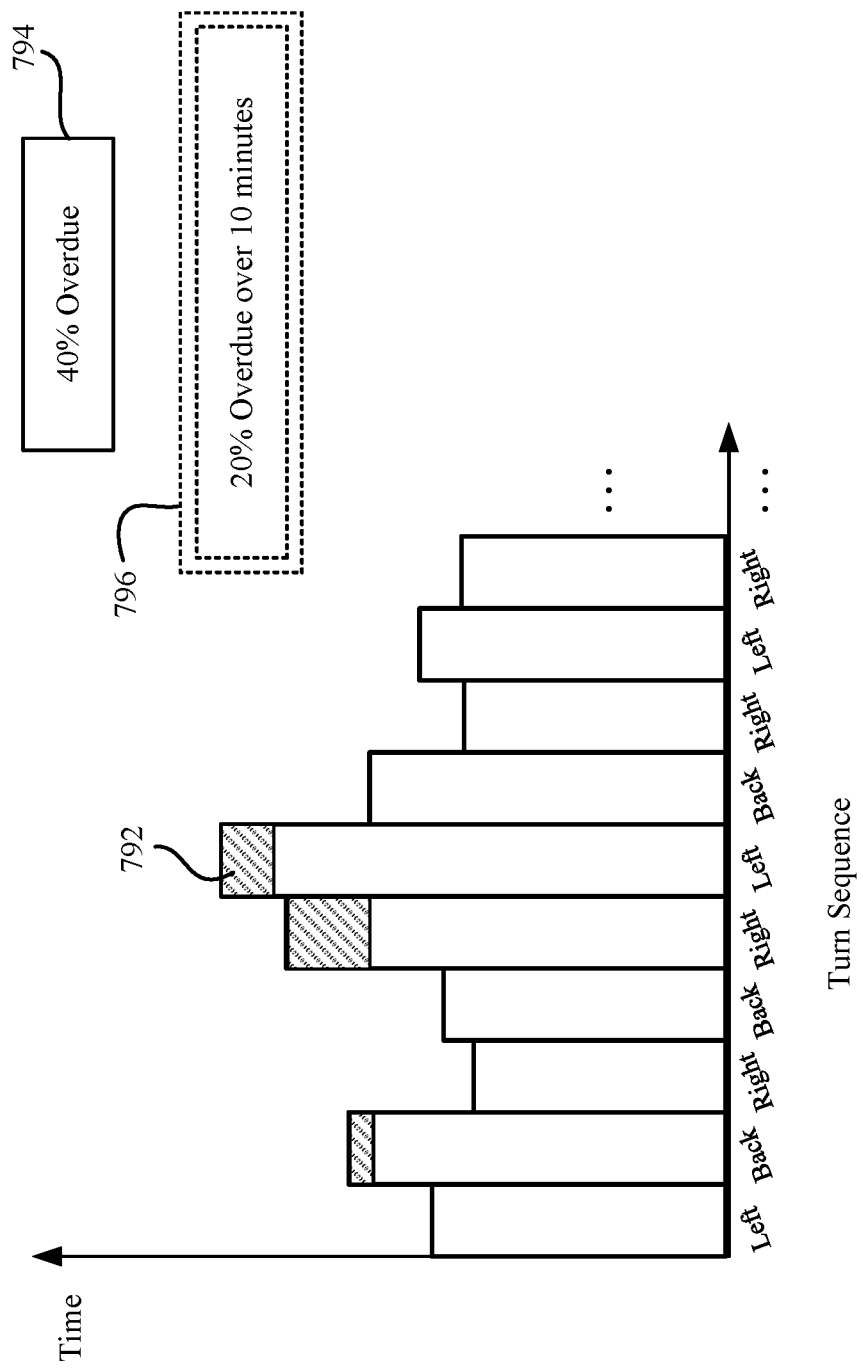
FIG. 7D is a graph illustrating an example turn sequence, in accordance with some embodiments.

FIG. 7B is a conceptual diagram illustrating several example heatmaps 750, 760, 770, in accordance with some embodiments.

The heatmaps 750, 760, 770 are embodiments of heatmap 710. Each include one or more circles 725 that represent various levels of pressure, surface moisture, surface temperature, and/or risk of developing pressure injury for a particular area or body part of a person. The first heatmap 750 corresponds to the person 715 seated upon a weight support device (e.g., a wheelchair). The heatmaps 760, 770 correspond to the person 715 laying upon a weight support device (e.g., a bed). In some embodiments, the heatmap 760 corresponds to the person 715 laying in a first weight support device (e.g., a bed in the emergency room) and the heatmap 770 corresponds to the person laying in a second weight support device (e.g., a bed in the operating room). In some embodiments, the heatmaps 750, 760, 770 and the associate data collected by the weight support devices used to generate the heatmaps 750, 760, 770 may correspond to a single visit to the hospital by the person 715. The heatmaps 750, 760, 770 and the associated data collected by the weight supporting devices are utilized by the computer in determining a pressure injury outcome for the person 715. The heatmaps 750, 760, 770 and the associated data collected by the weight supporting devices may also be added to the person's health record and stored in the data store 155.

FIG. 7C is a conceptual diagram illustrating an example visual representation 780 of a person, in accordance with some embodiments. The visual representation 780 may be displayed in the GUI 700. The visual representation 780 includes a generic body outline of the person 715. The visual representation 780 includes different body parts (e.g., joint locations) each labeled with a corresponding time label. The body parts (e.g., eleven parts) include a right shoulder, a left shoulder, a right shoulder blade, a left shoulder blade, the sacrum, a right hip, a left hip, a right ankle, a left ankle, a right heel, and a left heel. As shown in FIG. 7C, the left shoulder 782 has a time label of 3 hours, the right shoulder blade 784 has a time label of 2 hours, and the right ankle 786 has a time label of 2 hours. In some embodiments, the time labels may indicate a prediction of an amount of time until that corresponding body part develops a pressure injury based on the person's current position. In some embodiments, the time labels may indicate an amount of time until that corresponding body part develops a pressure injury based on the person's various positions over a specified time interval.

The body outline of the person 715 may be divided into three portions indicating three sides: right, back, and left. The right side corresponds to the right shoulder, the right hip, and the right ankle. The left side corresponds to the left shoulder, the left hip, and the left ankle. The back side corresponds to the right and left shoulder blades, the sacrum, and the right and left heels. Each side has a time label indicating a lowest time label of the corresponding body parts for that side. For example, the left side 788 has a time label of 3 hours which corresponds to the lowest time label of the left shoulder, the left hip, and the left ankle, where the left shoulder 782 has the lowest time label of 3 hours.

FIG. 7D is a graph 790 illustrating an example turn sequence, in accordance with some embodiments. In some embodiments, the GUI 700 may display the graph 790 indicating a turn sequence for the person 715. The graph 790 tracks position adjustments of the person 715 along the x axis labeled turn sequence. For example, the person 715 begins on their left side, adjusts positioning to their back side, adjusts positioning to their right side, and so on. The graph 790 also illustrates how long the person 715 remained on each side along the y axis labeled time. A portion 792 of the amount of time the person 715 remained on their left side is called out in the graph 790. The portion 792 indicates an amount of the time the person 715 remained on their left side over a determined amount of time (e.g., the lowest amount of time until a body part on that side may develop a pressure injury as described above in FIG. 7C). The graph 790 may indicate to the user how many position adjustments took place over the determined amounts of time with a message 794. The graph 790 may indicate to the user how many position adjustments took place over the determined amounts of time plus 10 minutes with another message 796.

The GUI 700 may display other relevant information about the person 715 in a table (not shown). For example, a table may track for each side (right, left, and back) of the person 715, how long the person was positioned (or currently positioned) on that side, how many times the person's position was adjusted from that side, how many times the person's position was adjusted over the determined amount of time, how many times the GUI 700 provided a notification to the user to adjust the positioning of the person 715, a total amount of time the notification(s) was displayed to the user, and which body parts of the side were at risk of developing a pressure injury (and contributing to the cause for notification).

Example Fall Outcome Detection Processes

Figure 8A:
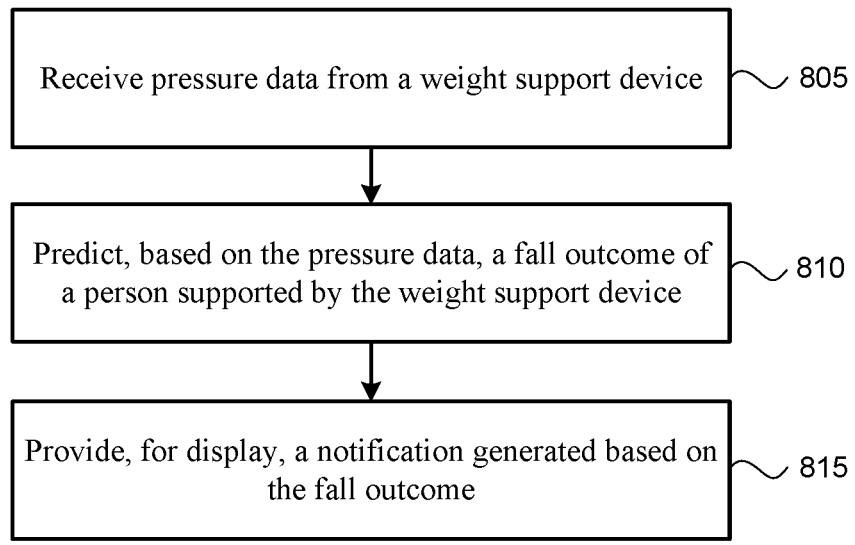
FIG. 8A is a flowchart depicting an example process for determining a fall outcome, in accordance with some embodiments.

FIG. 8A is a flowchart depicting an example process 800 for determining a fall outcome of a person supported by the weight support device 110, in accordance with some embodiments. A computer, which may be the computing server 140, the local computer 130, or the user device 160, may perform the process 800. Other entities may perform some or all of the steps in FIG. 8A in other embodiments. Embodiments may include different and/or additional steps or perform the steps in different orders.

The computer receives 810 pressure data from the weight support device 110. For example, the computer may receive the pressure data from the sensor grid layer 214 of the weight support device 100. The pressure data may be raw pressure data and include a time series of matrix readings (e.g., a tine series of pressure readings 627). The pressure data may also be processed data whose time series has been digitally filtered by various digital signal processing techniques such as a finite impulse response (FIR) filter, Gaussian filter, smoothing, etc. For each time instance, the pressure data may include two-dimensional data that correspond to the sensor grid of the weight support device 110.

The computer predicts 820, based on the pressure data, the fall outcome of the person supported by the weight support device 110. The prediction may also involve the use of other data such as position data 660 (e.g., side labels 667, joint locations 668, movement over time 672, and/or determined pose(s) 675 of the person). In some embodiments, the computer inputs the pressure data and position data 660 into a risk estimation module that utilizes a rule-based approach to predict the fall outcome. With the rule-based approach, the computer may determine a center of mass of the person based on the pressure data and the position data 660 and monitor a position of the center of mass of the person over time. The computer may determine a rate of movement of the person based on the movement over time 672 and monitor the rate of movement. The computer may monitor joint locations 668 relative to the weight support device 110 and/or positions of pressure readings relative to the weight support device 110. Based on the information the computer is monitoring, the computer predicts the fall outcome.

In some embodiments, the computer inputs the pressure data and position data 660 into one or more machine leaning models (e.g., a convolutional neural network (CNN)) to predict the fall outcome. In some embodiments, the models may monitor the data for any anomalies and based on a detected anomaly determine the fall outcome. In some embodiments, the models may be trained to detect a fall occurred (i.e., that the person experienced a fall) as opposed to the person getting off-of or out-of the weight support device 110 on purpose. In these embodiments, the fall outcome may include a risk of the person falling off of the weight support device 110 and/or an indication that a fall occurred.

The computer provides 830, for display, a notification generated based on the fall outcome. The notification may be displayed on the local computer 130, the user device 160, and/or the management device 170. The notification may include an alert or message to a user (e.g., a nurse) that the person supported by the weight support device 110 is at risk of falling off of the weight support device 110. The notification may also provide additional information, such as which side(s) of the weight support device 110 the person is at risk of falling off of and/or a recommendation for how best to adjust a positioning of the person to avoid the fall.

As described above, notifications may be routine or reactive. For example, some notifications may be periodically generated and include pressure values and vital information of the individual's different body parts. Other notifications may be alerts that are sent when actions (such as turning the patient or warning of potential fall) are needed under certain conditions. Any recommendations regarding position adjustments of the person may be based on tracked sensor data (e.g., aggregate sensor data) from one or more weight support devices 110 the patient has been supported by over the course of their treatment or hospital stay. For example, if the person consistently lays on a particular edge of the weight support device 110 (e.g., aggregate sensor data reflects a majority of pressure readings exceeding a pressure threshold come from pressure sensing elements located on the edge), the computer may recommend via the notification that one or more pillows or bolsters be placed on that edge to prevent the person from falling off that edge of the weight support device 110.

Figure 8B:
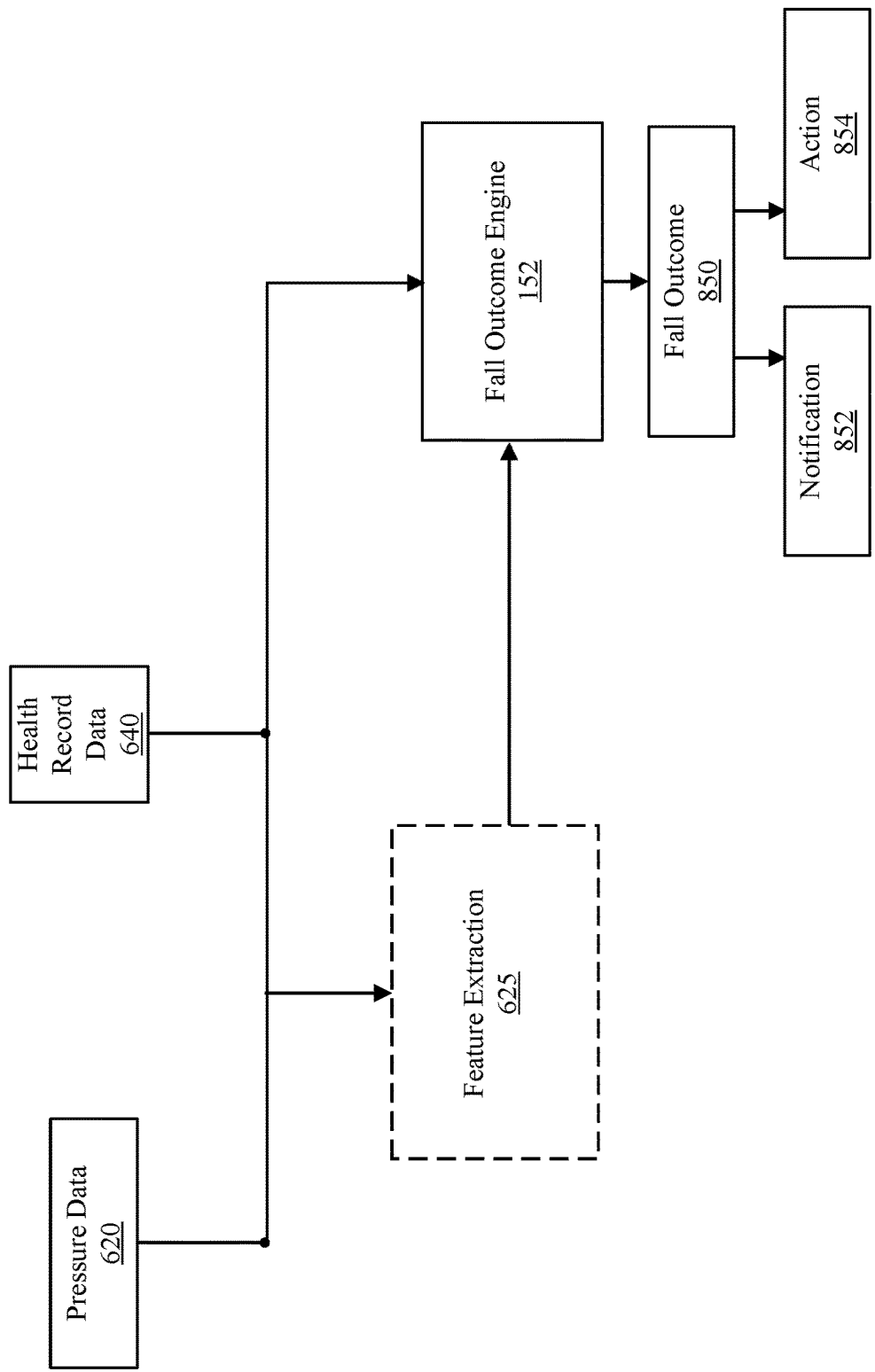
FIG. 8B is a block diagram illustrating an example algorithmic pipeline for predicting a fall outcome, in accordance with some embodiments.

FIG. 8B is a block diagram illustrating an example algorithmic pipeline for predicting a fall outcome 850 for a person, in accordance with some embodiments. The pipeline includes inputs, the feature extraction stage 625, and outputs of the pipeline.

The inputs include pressure data 620 and health record data 640. The pressure data 620 includes raw sensor readings currently being collected by a weight support device (e.g., the weight support device 110) as described above. The health record data 640 is stored in a database or data store (e.g., the data store 155) and may include information about the person, such as previously collected pressure data (e.g., historical sensor data) and various analyses (e.g., position data). For example, the health record data 640 may include aggregated pressure data collected by one or more weight support devices the person has come into contact with.

In some embodiments, the inputs are provided directly to the fall outcome engine 152. In some embodiments, the inputs are provided to the feature extraction stage 625. As described above, the feature extraction stage 625 may perform operations discussed in reference to the sensor mapping engine 142, the machine vision engine 144, and the machine learning engine 146. The feature extraction stage 625 extracts particular features which may be input into the fall outcome engine 152. The extracted features may include various position data 660 associated with the person (e.g., pose(s) 675 of the person, position(s) of the person, joint locations 668 of the person, and movement data over time 672). As described above, the feature extraction stage 625 may analyze the inputs to determine various position data 660 associated with the person by utilizing machine learning models discussed in detail with reference to FIG. 6C. The position data 660 (e.g., the joint locations 668) provides a two-dimensional and/or three-dimensional model of the person's body. In some embodiments, the model is a kinematic human body model.

The fall outcome engine 152 determines the fall outcome 850 for the person. The fall outcome engine 152 may utilize a rule-based approach and/or one or more machine learning models (e.g., a CNN) to determine the fall outcome 850. For example, the inputs may be directly fed into the fall outcome engine 152. In another example, the extracted features from the feature extraction stage 625 are fed into the fall outcome engine 152. The rule-based approach is discussed in further detail with reference to FIGS. 9A and 9B. The machine learning models are discussed in further detail with reference to FIGS. 9C and 9D.

The fall outcome 850 as described above may include a risk of the person falling off of the weight support device and/or an indication that the person experienced a fall (that a fall occurred). The fall outcome 850 may be communicated to a user (e.g., a healthcare professional, a caregiver, the person, etc.) via a notification 852. For example, the notification 852 may be displayed in a graphical user interface (e.g., the interface 165). In some embodiments, the notification 852 may be an audible message played for the user. The notification 852 may provide instructions to the user to adjust the position of the person to avoid a fall and how to adjust the position of the person to avoid the fall.

Based on the fall outcome 850, an action 854 may take place. For example, the user may adjust the positioning of the person. In another example, instructions may be provided to the weight support device to adjust the positioning of the person. The weight support device may do so by inflating or deflating one or more bladders or bolsters on the surface of the weight support device and/or by operating one or more servo motors that adjust the surface of the weight support device. In another example, instructions may be provided to the weight support device to adjust its positioning. The weight support device may do so by lowering (e.g., decreasing its height off of the ground) to minimize a potential fall distance. In another example, the weight support device may be provided instructions to activate one or more guard rails on one or more sides of the weight support device to prevent the fall and/or to active (inflate) one or more air bags positioned on the ground adjacent to the weight support device to reduce a fall impact.

Figure 9A:
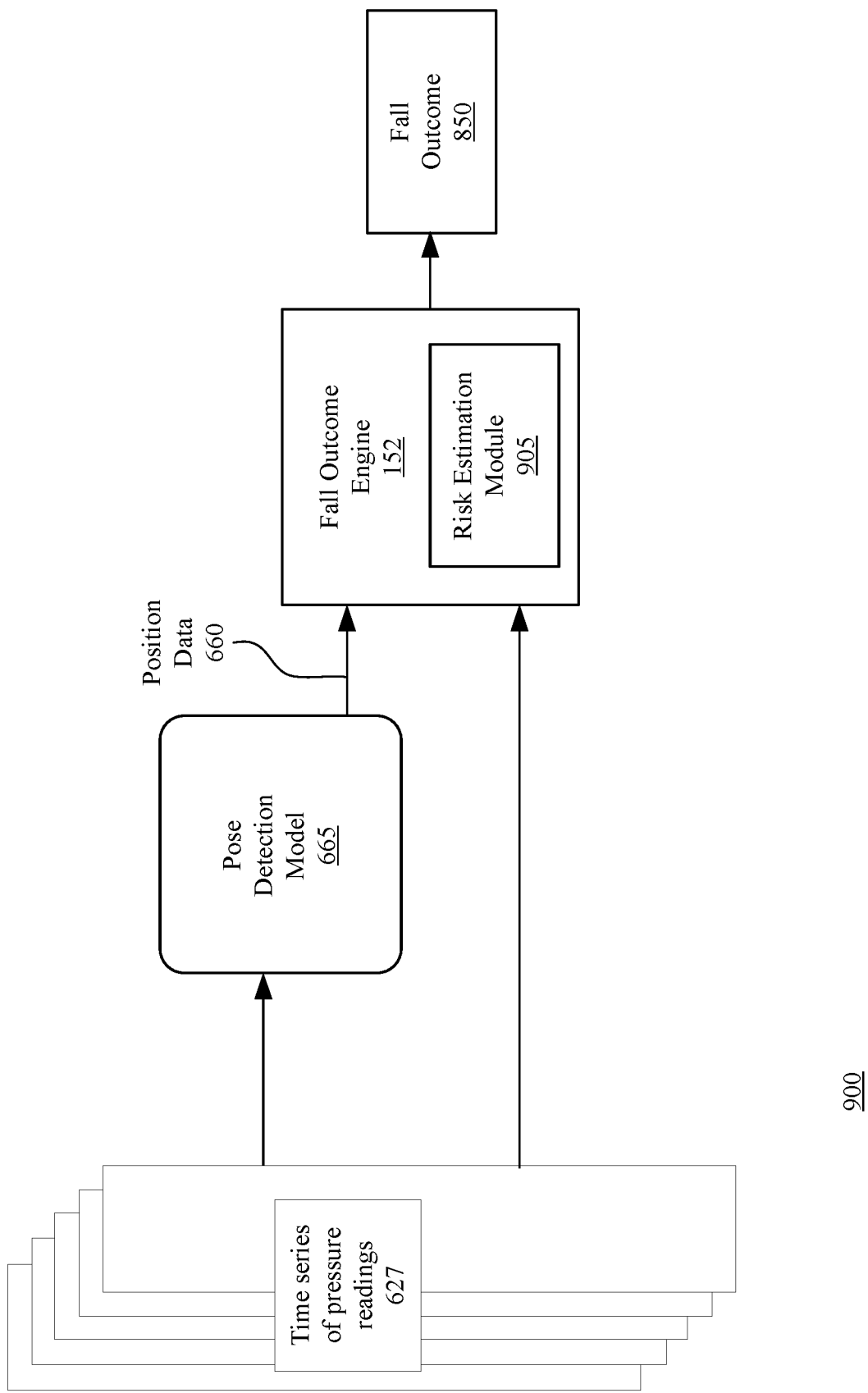
FIG. 9A is a first example data flow diagram for the fall outcome engine of FIG. 8B.

FIG. 9A is a first example data flow diagram 900 for the fall outcome engine 152 of FIG. 1A. The fall outcome engine 152, as illustrated, utilizes a risk estimation module 905 to predict the fall outcome 850. The risk estimation module 905 is a rule-based approach for predicting the fall outcome 850.

The fall outcome engine 152 receives pressure data from the weight support device 110 (e.g., from the sensor grid layer 214). The pressure data may be a time series of pressure readings 627. The fall outcome engine 152 can also receive position data 660 (e.g., side labels 664, joint locations 668, movement over time 672, and/or poses 675) from the pose detection model 665. In this embodiment illustrated in FIG. 9A, the fall outcome engine 152 utilizes a risk estimation module 905 to determine the fall outcome 850 based on the pressure data and the position data 660. The risk estimation module 905 can determine a center of mass for the person based on the time series of pressure readings 627 and the position data 660 (e.g., the pose of the person). The risk estimation module 905 can determine a rate of movement of the person based on the movement over time 672. For example, the risk estimation module 905 may determine how fast a person is moving (a speed or an acceleration) while sitting or lying on the weight support device 110 by analyzing a change in position of the person over time (i.e., by analyzing the movement over time 672).

The risk estimation module 905 analyzes a position of the center of mass relative to the weight support device 110, joint locations 668 relative to the weight support device 110, positions of pressure readings relative to the weight support device 110, and/or the rate of movement of the person to determine the fall outcome 850. The fall outcome 850 determined by the risk estimation module 905 is a risk of the person falling off of the weight support device 110. The risk may be binary, such as yes/no or 1/0, indicating the person is either at risk or not at risk. For example, the risk estimation module 905 may determine the position of the center of mass is located on an edge of the weight support device 110 and the resulting fall outcome 850 indicates the person is at risk of falling. In another example, the risk estimation module 905 may determine a majority of joint locations 668 (e.g., greater than 50%, 60%, 75%, etc.) are located at on an edge of the weight support device 110 and the rate of movement of the person is greater than a threshold rate, as such the fall outcome 850 indicates the person is at risk of falling. In another example, the risk estimation module 905 may determine a majority of pressure readings that are greater than a pressure threshold are coming from pressure sensing elements located in a center of the weight support device 110, thus the fall outcome 850 indicates the person is not at risk of falling.

The risk estimation module 905 may weigh certain features higher than others when determining the fall outcome 850. For example, the risk estimation module 905 may place a higher weight on the position of the center of mass relative to the weight support device 110 relative to the positions of pressure readings relative to the weight support device 110. For example, the risk estimation module 905 may determine the position of the center of mass is located in the center of the weight support device 110 and a majority of pressure readings that are greater than a pressure threshold are coming from pressure sensing elements located on an edge of the weight support device 110. With a higher (greater) weight placed on the position of the center of mass, the risk estimation module 905 outputs a fall outcome 850 indicating the person is not at risk of falling.

Figure 9B:
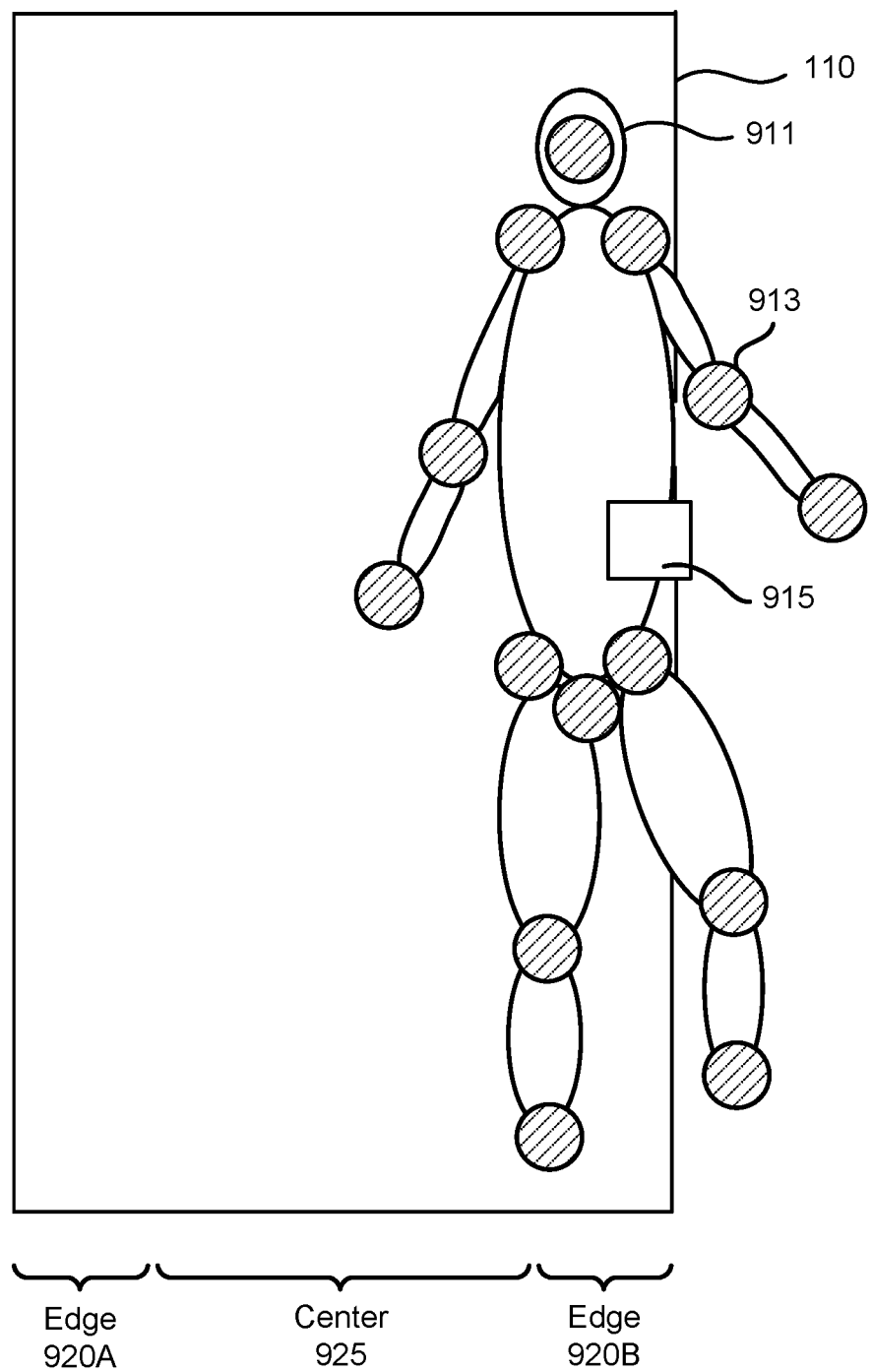
FIG. 9B is a conceptual diagram illustrating a high fall risk scenario detected by the fall outcome engine of FIG. 9A.

FIG. 9B is a conceptual diagram illustrating a high fall risk scenario 910 detected by the risk estimation module 905 of FIG. 9A. The high fall risk scenario 910 illustrates a person 911 lying on the weight support device 110 (e.g., a bedding system). The various circles represent the joint locations 668. For example, the left elbow joint 913 is not currently located above the weight support device 110. The square represents the determined position 915 of the center of mass of the person. The weight support device 110 includes two edges 920 (e.g., an edge 920A and an edge 920B) and a center 925. The risk estimation module 905 outputs a fall outcome 850 indicating the person is at risk of falling due to the position 915 of the center of mass being on the edge 920B and due to a majority (over 50%) of the joint locations 668 also being located on the edge 920B. Based on the fall outcome 850, a notification can be provided to a user (e.g., a caregiver or nurse) to adjust the positioning of the person so that a fall can be avoided.

Figure 9C:
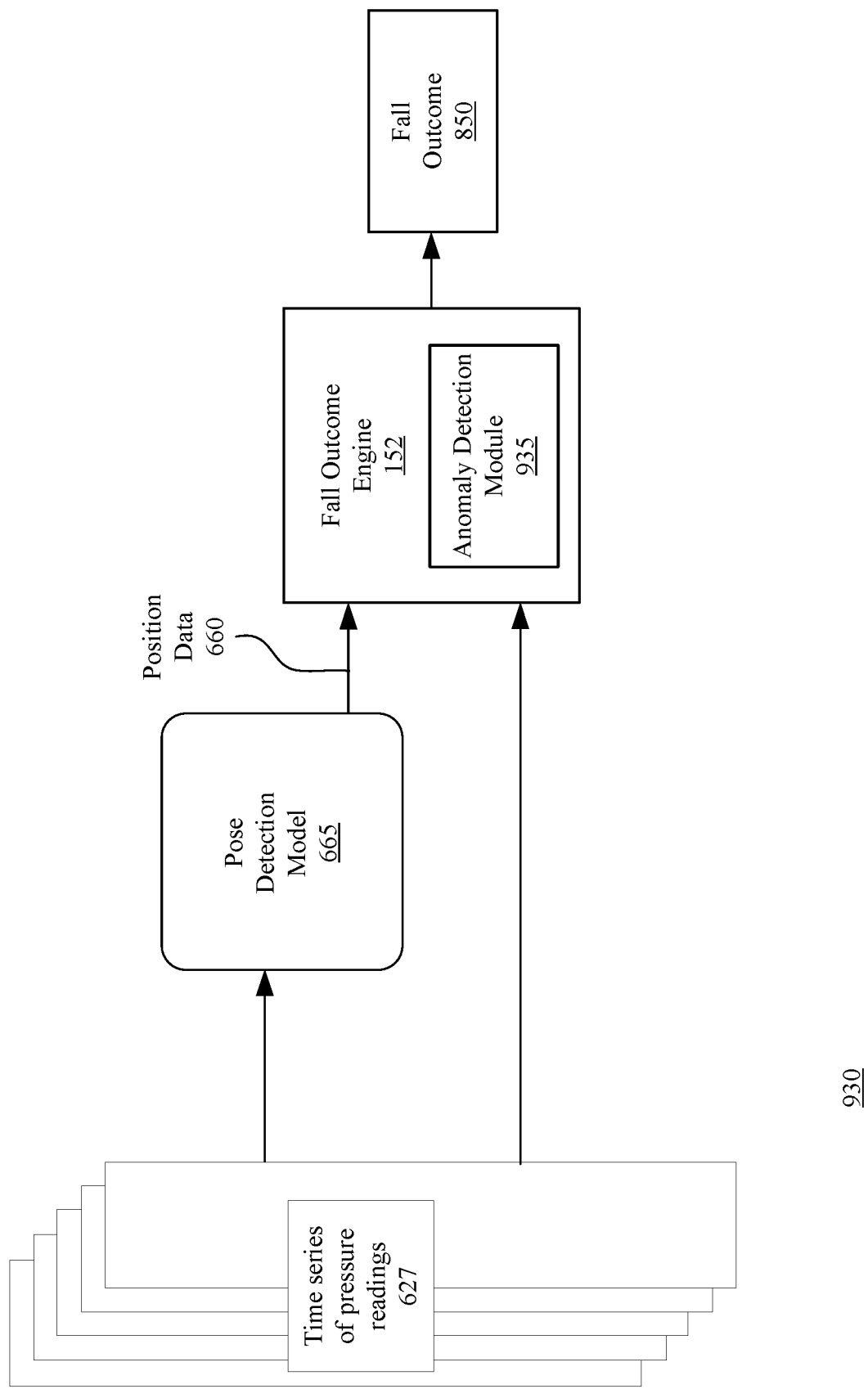
FIG. 9C is a second example data flow diagram for the fall outcome engine of FIG. 8B.

FIG. 9C is a second example data flow diagram 930 for the fall outcome engine 152 of FIG. 1A. The fall outcome engine 152, as illustrated, utilizes an anomaly detection module 935 to predict the fall outcome 850. The anomaly detection module 935 is a machine learning model for predicting the fall outcome 850.

As described above, the fall outcome engine 152 receives pressure data (e.g., the time series of pressure readings 627) from the weight support device 110 and can also receive position data 660 from the pose detection model 665. In this embodiment illustrated in FIG. 9C, the fall outcome engine 152 utilizes an anomaly detection module 935 to determine the fall outcome 850. The anomaly detection module 935 utilizes an unsupervised machine learning model to detect any anomaly in the pressure data and/or position data 660. The anomaly detection module 935 monitors incoming (current) pressure readings and/or position data 660 for anomalies. For example, the anomaly detection module 935 may compare the incoming pressure readings to aggregate sensor data and/or previously determined position data stored in the health record of the person. In an example, an anamoly may be determined whenever the person is not (e.g., whenever substantially all of the joint locations 668 are not) located in the center 925 of the weight support device 110. In another example, an anamoly may be determined if one or more joint locations 668 are no longer being supported by the weight support device 110 (e.g., the person's right shoulder, right forearm, and right hand are no longer on the weight support device 110). Whenever an anamoly is detected, the anomaly detection module 935 outputs a fall outcome 850 indicating the person is at risk of falling.

Figure 9D:
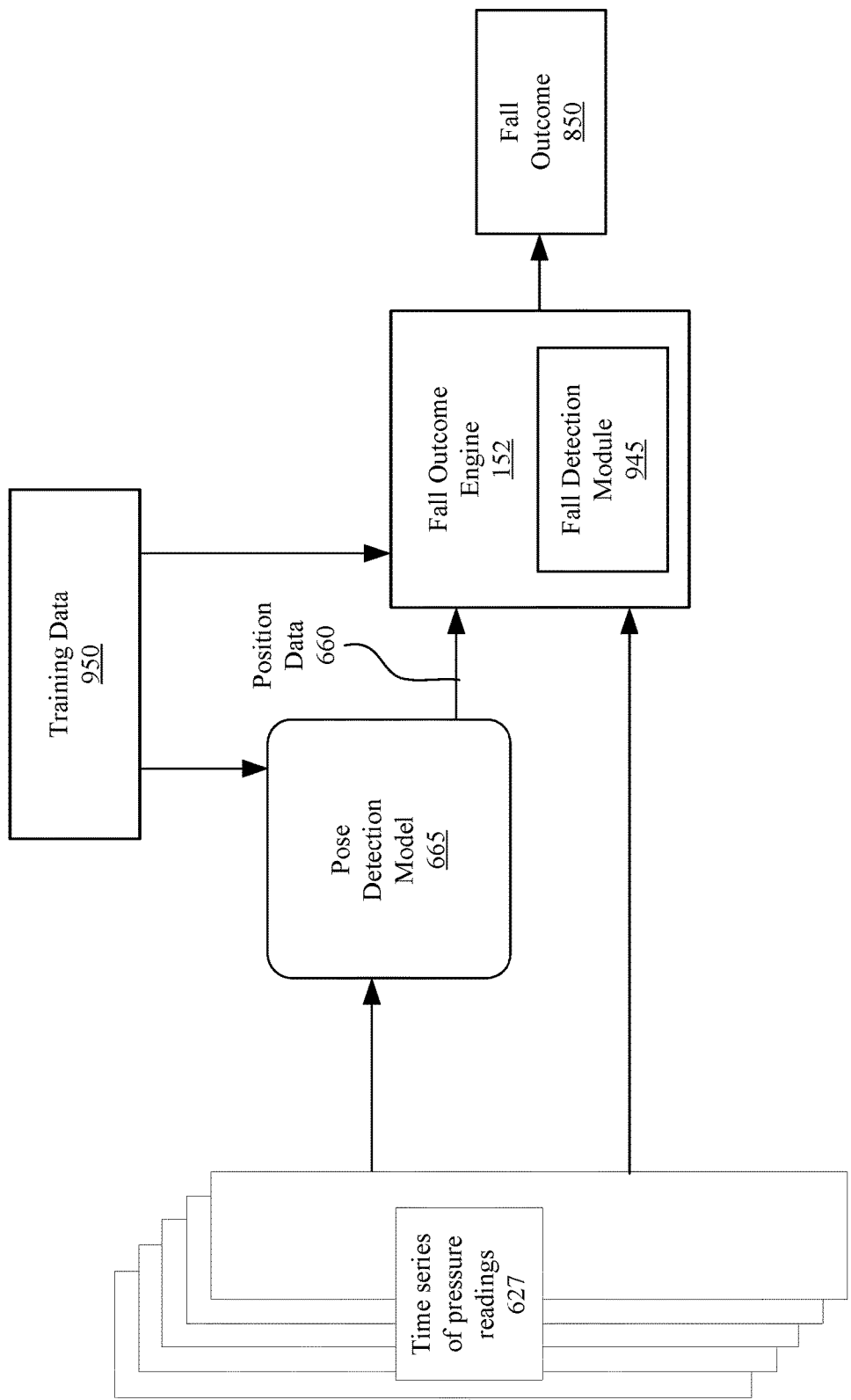
FIG. 9D is a third example data flow diagram for the fall outcome engine of FIG. 8B.

FIG. 9D is a third example data flow diagram 940 for the fall outcome engine 152 of FIG. 1A. The fall outcome engine 152, as illustrated, utilizes a fall detection module 945 to predict the fall outcome 850. The fall detection module 945 is a machine learning model for predicting the fall outcome 850.

As described above the fall outcome engine 152 receives pressure data (e.g., the time series of pressure readings 627) from the weight support device 110 and can also receive position data 660 from the pose detection model 665. In this embodiment illustrated in FIG. 9D, the fall outcome engine 152 utilizes a fall detection module 945 to determine the fall outcome 850. The fall detection module 945 utilizes a supervised machine learning model to determine the fall outcome 850. Here, the fall outcome 850 may include a risk of the person falling off of the weight support device 110 and/or if a fall has occurred. The fall detection module 945 may be trained using training data 950 that includes labeled pressure data and/or labeled position data. The labeled data may indicate whether a fall occurred or did not occur (e.g., when the person simply moved out-of or off-of the weight support device 110 on purpose). Based on the training, the fall detection module 945 can predict a risk of the person falling and can determine if a fall took place. Based on the fall outcome 850, a notification can be provided to a user (e.g., a caregiver or nurse) to adjust the positioning of the person so that a fall can be avoided or the notification may alert the user that a fall took place and the person needs immediate assistance.

Additionally or alternatively, piezoelectric sensors incorporated on the weight support device 110 may detect that a fall has occurred. Data (e.g., signals received) from the piezoelectric sensors may be used by the fall outcome engine 152 to determine a fall took place and subsequently provide a notification to a user (e.g., a healthcare professional) that the person (e.g., a patient) has fallen and needs assistance.

Additional Example Uses of the Weight Support Device

Additionally or alternatively, the detection of body movement, respiration and heart rates, and body, joint, and limb positions generated from the data analysis can be used on their own outside of pressure injury outcome detection and/or fall outcome detection to provide more information to clinicians.

Activity level can be derived from a number of different signals extracted from the intelligent surface. Average pressure over time can be used to identify when a body is moving on top of the intelligent surface. The change in body, joint, and limb position can be used to more granularly identify when a specific part of the user's body has moved. By combining those two together, activity level and the movement of a body segment can be used to inform clinical decisions.

Seizures, formally known as epileptic seizures, are a period of symptoms due to abnormal neuronal activity in the brain. Seizures that last for more than a brief period are considered a medical emergency and those lasting longer than 5 minutes are called status epilepticus (SE) and are a life-threatening medical emergency. The intelligent surface could be used to provide an alert and actionable information to clinical staff if a patient on top of the surface experiences a seizure. While signs and symptoms of seizures will vary with the type, the majority of seizures are known as convulsive, beginning as either a focal seizure and becoming generalized or starting and staying a generalized seizure. For focal seizures, symptoms may include jerking activity starting in a specific muscle group and moving to surrounding muscle groups such as the smacking of lips or unconscious jerking to pick up and object. For generalized seizures, symptoms will include the sudden loss of consciousness and may include uncontrolled contraction and extension of the limbs, the prolonged arching of the back for 10-30 seconds, convulsion of limbs in unison, muscles spasms in a few limbs or the entire body. Because the intelligent surface can be used to detect movement of the body as well as the movement of specific limbs or joints over time, these features can be fed into a system of machine learning models to detect seizure occurrence. For example, if when tracking the movement of the patient, all limbs convulse in unison, the time at which that set of movements started can be recorded and a notification sent to clinical staff to check on the patient. If they are experiencing a seizure, the start time can be used by the clinician to determine if the event is an SE or a regular seizure in order to better provide treatment, given the knowledge that SEs are considered medical emergencies and can be life threatening with delayed treatment.

Surface or bed occupancy can be useful clinical information for a variety of applications, including monitoring in long term care homes where patients are encouraged to adhere to an activity schedule and avoid roaming at certain times of the day. While a basic threshold can be used to determine occupancy based on a general average pressure value, more intelligent occupancy detection systems can be used by leveraging the intelligent surface's body, joint, and limb position systems.

Incontinency and/or excessive sweating detection provides an important service in both clinical and at-home settings. Detecting when a patient may have involuntarily relieved themselves and/or may be excessively sweating is important not only for the prevention of a pressure injury, but also for the patient's comfort and overall care. Incontinency and/or excessive sweating may be symptoms of an illness or disease the patient is suffering from or be a side-effect of medication the patient is taking. Regardless, knowledge of the symptom or side-effect is important for healthcare providers or other caregivers to know. With the capacitive sensor grid detecting surface moisture on the intelligent surface and alerting the healthcare provider or caregiver to it immediately, the patient may be provided immediate care or relief.

Respiratory and heart failure are major causes of death and can be caused by a variety of symptoms. If clinicians are able to catch patients at the onset or during a respiratory or a heart failure event, the patient's chances of survival are dramatically increased. Because the intelligent surface can monitor vital signs such as respiration and heart rate over time, if those detected breaths or beats per minute fall outside of healthy range and either reach extremely high or extremely low values, clinicians can be notified and provide treatment as needed depending on the type of failure and underlying causes.

Speaking, coughing, eating, and drinking are common events in both regular life and within the hospital. With certain treatments, compliance to eating or drinking may be important pieces of clinical information. For certain illnesses, the frequency and magnitude of coughing are important for clinicians. All of these events are respiration related in that they involve the pharynx and esophagus, parts of the respiratory system. In either aforementioned case, because the intelligent surface is able to extract a patient's thoracic effort when they are on the surface, this signal can be processed to understand whether the user is speaking, coughing, eating, or drinking based on the signal's characteristics.

Example Architecture of Machine Learning Models

In various embodiments, a wide variety of machine learning techniques may be used for detection of a pressure injury outcome, a person's pose such as side labels and joint locations, identification of the person's outline, identification of potential seizure, identification of imminent fall, and other uses described herein. The machine learning techniques include different forms of supervised learning, unsupervised learning, and semi-supervised learning such as decision trees, support vector machines (SVMs), regression, Bayesian networks, and genetic algorithms. Deep learning techniques such as neural networks, including convolutional neural networks (CNN) and recurrent neural networks (RNN) (e.g., long short-term memory networks (LSTM)), may also be used. For example, for the detection of a pressure injury outcome for a person that is described in FIGS. 6A and 6B, a CNN may be used.

In various embodiments, the training techniques for a machine learning model may be supervised, semi-supervised, or unsupervised. In supervised learning, the machine learning models may be iteratively trained with a set of training samples that are labeled. For example, for a machine learning model trained to classify body parts at risk of developing a pressure injury, the training samples may be different heatmaps of pressure data labeled with body parts that did and did not develop pressure injuries. In another example, in a machine learning model trained to detect a likely fall, the training samples may be different heatmaps of pressure data labeled with either a yes or no (e.g., a 1 or 0) indicating the person did experience a fall or did not experience a fall. Thus, the labels for each training sample may be binary or multi-class.

In another example for iteratively training a machine learning model to determine when a person should have their position adjusted to avoid a pressure injury, the training samples may be historical data of individuals who developed a pressure injury (e.g., each individual's pressure data and health record). For training a binary machine learning model (e.g., a model that identifies whether a person develops pressure injury, whether a particular body part of a person develops a pressure injury, etc.), training samples may include a positive training set (with training samples that have the label of having a pressure injury) and a negative training set (with training samples that have the label of not having a pressure injury). In some cases, an unsupervised learning technique may be used. The samples used in training are not labeled. Various unsupervised learning techniques such as clustering may be used. In some cases, the training may be semi-supervised with the training set having a mix of labeled samples and unlabeled samples.

A machine learning model may be associated with an objective function, which generates a metric value that describes the objective goal of the training process. For example, the training may intend to reduce the error rate of the model in generating predictions. In such a case, the objective function may monitor the error rate of the machine learning model. In object recognition (e.g., object detection and classification), the objective function of the machine learning algorithm may be the training error rate in classifying objects in a training set. Such an objective function may be called a loss function. Other forms of objective functions may also be used, particularly for unsupervised learning models whose error rates are not easily determined due to the lack of labels. In pressure injury outcome detection, the objective function may correspond to the difference between the model's prediction of a person developing a pressure injury and the manually identified development of a pressure injury in the training sets. In fall outcome detection, the objective function may correspond to the difference between the model's prediction that a person may experience a fall and the manually identified fall(s) experienced by the person in the training set. In various embodiments, the error rate may be measured as cross-entropy loss, L1 loss (e.g., the sum of absolute differences between the predicted values and the actual value), L2 loss (e.g., the sum of squared distances).

Figure 10:
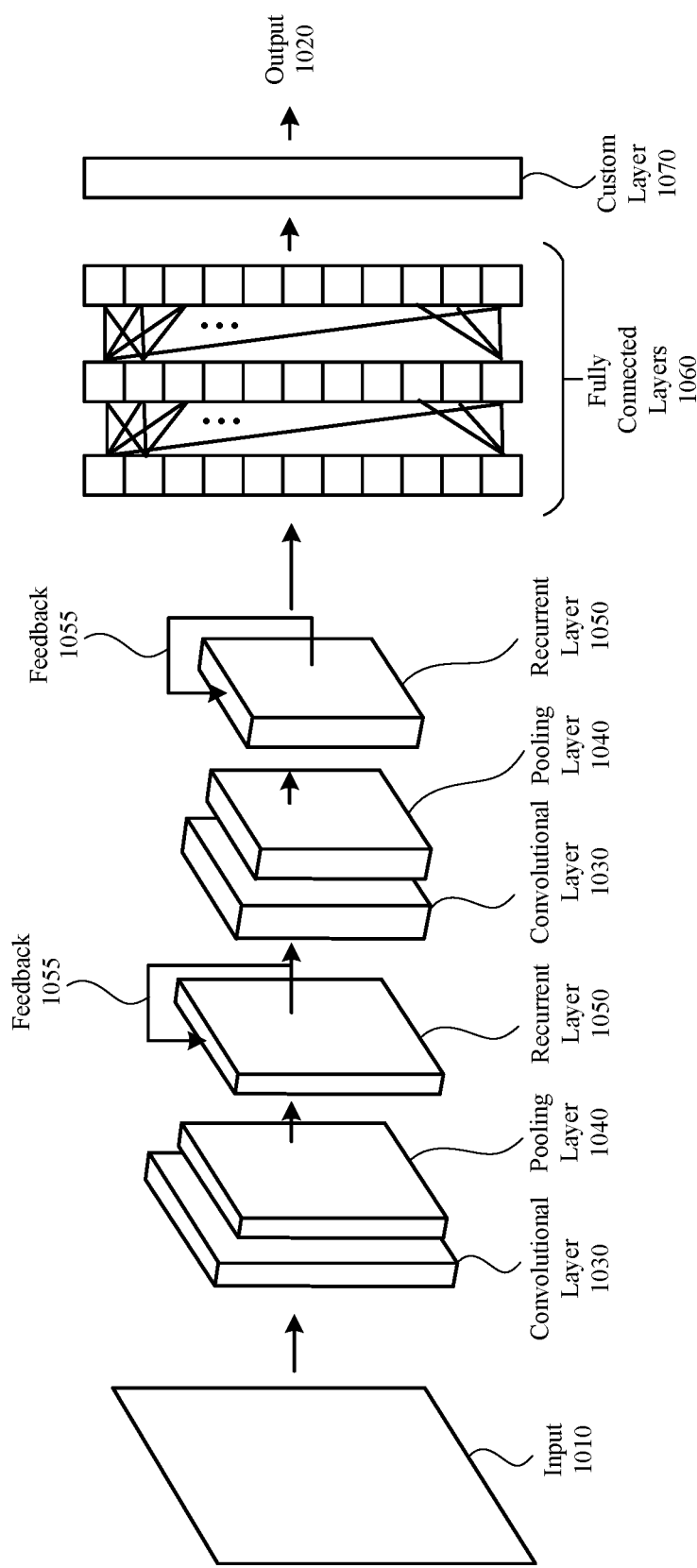
FIG. 10 is an example structure of a machine learning model, according to some embodiments.

FIG. 10 shows an example structure of a neural network, which may include layers that may present in various machine learning models. For example, a CNN may include the convolutional layers and the pooling layers shown in FIG. 10. An LSTM may include the recurrent layers shown in FIG. 10. Each machine learning models may have its own structure and layers (while omitting some layers in FIG. 10). The order of the layers in FIG. 10 is also an example. The order of layers may change, depending on the type of machine learning model used.

Referring to FIG. 10, a structure of an example neural network (NN) is illustrated, according to an embodiment. The NN 1000 may receive an input 1010 and generate an output 1020. The NN 1000 may include different kinds of layers, such as convolutional layers 1230, pooling layers 1040, recurrent layers 1050, full connected layers 1060, and custom layers 1070. A convolutional layer 1230 convolves the input of the layer (e.g., an image) with one or more kernels to generate different types of images that are filtered by the kernels to generate feature maps. Each convolution result may be associated with an activation function. A convolutional layer 1230 may be followed by a pooling layer 1040 that selects the maximum value (max pooling) or average value (average pooling) from the portion of the input covered by the kernel size. The pooling layer 1040 reduces the spatial size of the extracted features. In some embodiments, a pair of convolutional layer 1230 and pooling layer 1040 may be followed by a recurrent layer 1050 that includes one or more feedback loop 1055. The feedback 1055 may be used to account for spatial relationships of the features in an image or temporal relationships of the objects in the image. The layers 1230, 1040, and 1050 may be followed in multiple fully connected layers 1060 that have nodes (represented by squares in FIG. 10) connected to each other. The fully connected layers 1060 may be used for classification and object detection. In one embodiment, one or more custom layers 1070 may also be presented for the generation of a specific format of output 1020. For example, a custom layer may be used for image segmentation for labeling pixels of an image input with different segment labels.

The order of layers and the number of layers of the NN 1000 in FIG. 10 is for example only. In various embodiments, a NN 1000 includes one or more convolutional layers 1230 but may or may not include any pooling layer 1040, recurrent layer 1050, or fully connected layers 1060. If a pooling layer 1040 is present, not all convolutional layers 1230 are always followed by a pooling layer 1040. A recurrent layer may also be positioned differently at other locations of the CNN. For each convolutional layer 1230, the sizes of kernels (e.g., 3×3, 5×5, 7×7, etc.) and the numbers of kernels allowed to be learned may be different from other convolutional layers 1230.

A machine learning model may include certain layers, nodes, kernels and/or coefficients. Training of a neural network, such as the NN 1000, may include forward propagation and backpropagation. Each layer in a neural network may include one or more nodes, which may be fully or partially connected to other nodes in adjacent layers. In forward propagation, the neural network performs the computation in the forward direction based on outputs of a preceding layer. The operation of a node may be defined by one or more functions. The functions that define the operation of a node may include various computation operations such as convolution of data with one or more kernels, pooling, recurrent loop in RNN, various gates in LSTM, etc. The functions may also include an activation function that adjusts the weight of the output of the node. Nodes in different layers may be associated with different functions.

Each of the functions in the neural network may be associated with different coefficients (e.g. weights and kernel coefficients) that are adjustable during training. In addition, some of the nodes in a neural network may also be associated with an activation function that decides the weight of the output of the node in forward propagation. Common activation functions may include step functions, linear functions, sigmoid functions, hyperbolic tangent functions (tan h), and rectified linear unit functions (ReLU). After an input is provided into the neural network and passes through a neural network in the forward direction, the results may be compared to the training labels or other values in the training set to determine the neural network's performance. The process of prediction may be repeated for other images in the training sets to compute the value of the objective function in a particular training round. In turn, the neural network performs backpropagation by using gradient descent such as stochastic gradient descent (SGD) to adjust the coefficients in various functions to improve the value of the objective function.

Multiple rounds of forward propagation and backpropagation may be performed. Training may be completed when the objective function has become sufficiently stable (e.g., the machine learning model has converged) or after a predetermined number of rounds for a particular set of training samples. The trained machine learning model can be used for performing a pressure injury outcome detection, body part detection, joint identifications, fall outcome detection, or another suitable task for which the model is trained.

Computing Machine Architecture

Figure 11:
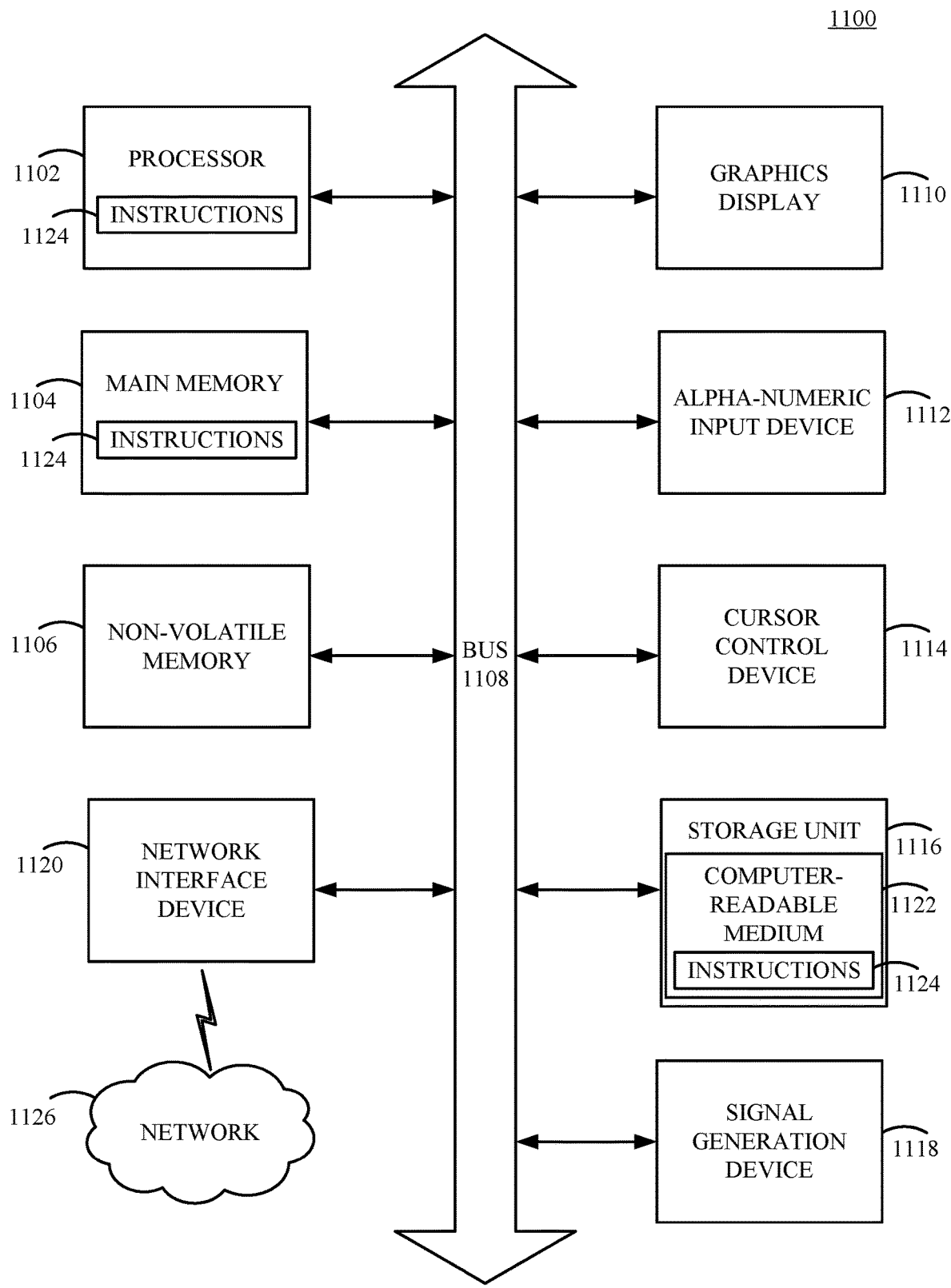
FIG. 11 is a block diagram illustrating components of example computing machines, according to some embodiments.

FIG. 11 is a block diagram illustrating components of an example computing machine that is capable of reading instructions from a computer-readable medium and executing them in a processor (or controller). A computer described herein may include a single computing machine shown in FIG. 11, a virtual machine, a distributed computing system that includes multiples nodes of computing machines shown in FIG. 11, or any other suitable arrangement of computing devices.

By way of example, FIG. 11 shows a diagrammatic representation of a computing machine in the example form of a computer system 1100 within which instructions 1124 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a network deployment, the machine may operate in the capacity of a server machine or a client machine in a server-client network environment, or as a peer machine in a peer-to-peer (or distributed) network environment.

The structure of a computing machine described in FIG. 11 may correspond to any software, hardware, or combined components shown in FIGS. 1A and 1B, including but not limited to, the computing server 140, the local computer 130, the data store 155, the user device 160, the cloud actionable insight system 185, and any computer that performs processes such as processes 600 and 800.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1124 that specify actions to be taken by that machine. Further, while only a single machine is illustrated, the term "machine" shall also be taken to include any collection of machines that individually or jointly execute instructions 1124 to perform any one or more of the methodologies discussed herein.

The example computer system 1100 includes one or more processors (generally, processor 1102) (e.g., a central processing unit (CPU), a graphics processing unit (GPU), a digital signal processor (DSP), one or more application-specific integrated circuits (ASICs), one or more radio-frequency integrated circuits (RFICs), or any combination of these), a main memory 1104, and a non-volatile memory 1106, which are configured to communicate with each other via a bus 1108. The computer system 1100 may further include graphics display unit 1110 (e.g., a plasma display panel (PDP), a liquid crystal display (LCD), a projector, or a cathode ray tube (CRT)). The computer system 1100 may also include alphanumeric input device 1112 (e.g., a keyboard), a cursor control device 1114 (e.g., a mouse, a trackball, a joystick, a motion sensor, or other pointing instrument), a storage unit 1116, a signal generation device 1118 (e.g., a speaker), and a network interface device 1120, which also are configured to communicate via the bus 1108.

The storage unit 1116 includes a computer-readable medium 1122 on which is stored instructions 1124 embodying any one or more of the methodologies or functions described herein. The instructions 1124 may also reside, completely or at least partially, within the main memory 1104 or within the processor 1102 (e.g., within a processor's cache memory) during execution thereof by the computer system 1100, the main memory 1104 and the processor 1102 also constituting computer-readable media. The instructions 1124 may be transmitted or received over a network 1126 via the network interface device 1120.

While computer-readable medium 1122 is shown in an example embodiment to be a single medium, the term "computer-readable medium" should be taken to include a single medium or multiple media (e.g., a centralized or distributed database, or associated caches and servers) able to store instructions (e.g., instructions 1124). The computer-readable medium 1122 may include any medium that is capable of storing instructions (e.g., instructions 1124) for execution by the machine and that cause the machine to perform any one or more of the methodologies disclosed herein. The computer-readable medium 1122 may include, but not be limited to, data repositories in the form of solid-state memories, optical media, and magnetic media. The computer-readable medium 1122 does not include a transitory medium such as a signal or a carrier wave.

Example Circuitry for Weight Support Device

Figure 12:
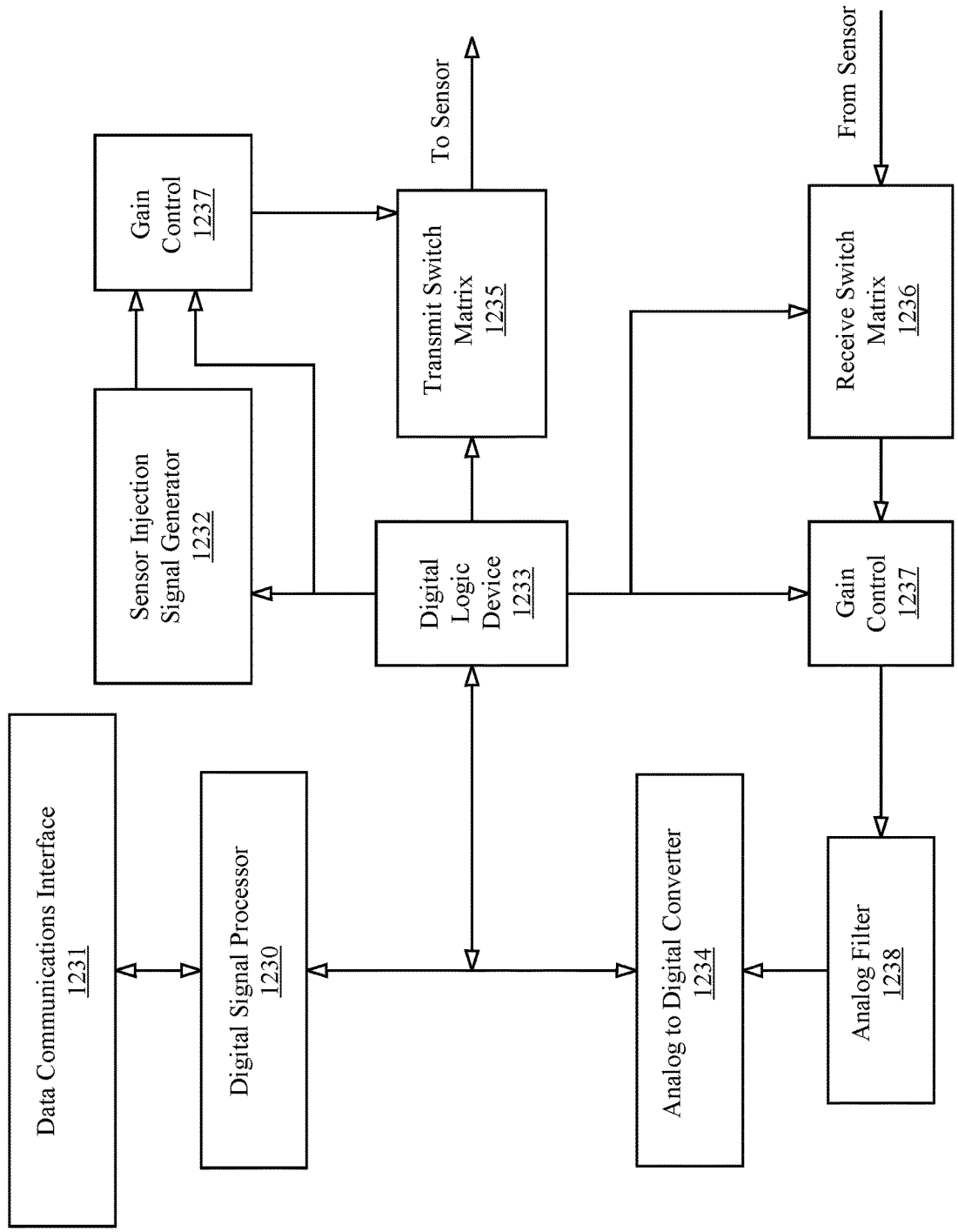
FIG. 12 is a block diagram illustrating example circuitry of a weight support device, in accordance with some embodiments.

FIG. 12 is a block diagram illustrating an example circuitry of a weight support device 110, in accordance with some embodiments. The circuitry of a weight support device 110 may include a digital signal processor (DSP) 1230, injection signal generation and control 1232, 1237, 1235, signal detection and control 1236, 1237, 1238, 1234, a digital logic device 1233, and a data communications interface 1231.

The DSP 1230 executes firmware that is designed to receive control messages from application software running on a personal computer or embedded computer via the data communications interface 1231. The control messages may include measurement requests that contain coordinates for an individual sensing element (sensel) within the pressure sensor array. The DSP 1230 selects a column for the injection signal and a row for signal detection. The detected signal is then converted from analog to digital 1234 for measurement processing by the DSP 1230. The measurement is then passed back to the application software via the data communications interface 1231.

The DSP 1230 may be a standalone device or include external memory such as Random Access Memory (RAM), Read Only Memory (ROM), or any other commonly used memory device. Memory devices can be accessed either serially or via parallel data bus.

The sensor injection signal generator 1232 is an electronic device or circuit used to create a sinusoidal injection signal at a selectable frequency. The injection signal can be in the range of 1 kHz to 5 MHz, or preferably 1 kHz to 250 kHz.

The gain control 1237 is an electronic device or circuit used to adjust the amplitude of the injection signal. The gain setting is controlled by the DSP 1230 via the digital logic device 1233. The amplified injection signal is connected to the transmit switch matrix 1235. The DSP 1230 configures the digital logic device 1233 to enable the appropriate switch in the transmit switch matrix 1235 in order to select a sensor column for transmitting the injection signal.

The injection signal passes through the pressure sensor and is detected on a row selected using the receive switch matrix 1236. The sensor row is selected by the DSP 1230 via the digital logic device 1233 and the selected signal is connected to the gain control 1237 for amplification.

An analog filter 1238 removes signal noise before the analog to digital converter (ADC) 1234. The analog filter 1238 is an electronic device or circuit that acts as a band pass or low pass filter and only passes frequencies near the injection signal frequency. For example, if the injection signal has a frequency of 250 kHz the filter only passes frequencies in the range of 200 kHz to 350 kHz and thereby rejects other interfering signals that are not within the pass band. The analog filter 1238 can be designed to accommodate pass bands of variable frequency spreads where tighter frequency spreads more effectively filter interfering signals.

The ADC 1234 is periodically sampled by the DSP 1230 in order to acquire sufficient samples for performing a measurement calculation. For example, 12, 24, 48, 96, or 192 samples can be acquired before performing a measurement calculation on the samples. The DSP 1230 can also execute firmware to perform additional digital filtering in order to further reduce the frequency spread of the pass band and more effectively filter interfering signals. Digital filtering requires more samples from the ADC 1234, for example in the range of 50 to 2500 samples, or preferably 512 samples.

The data communications interface 1231 passes data between the DSP 1230 and the application software running on the Control Processor Unit. The interface includes electronic devices or circuitry to perform wired or wireless communication. Examples of wired communication include RS232 serial, Universal Serial Bus (USB), Ethernet, fibre-optic, or any other serial or parallel data communication technology. Examples of wireless communication include, Zigbee, Bluetooth, WiFi, Wireless USB, or any other wireless data communication technology.

The digital logic device 1233 includes electronic devices or circuitry, for example complex programmable logic devices (CPLD), field programmable gate arrays (FPGA), application specific integrated circuits (ASIC), or discrete logic devices. Alternatively, the DSP 1230 has General Purpose Input Output (GPIO) pins that may be used in place of the digital logic device to control selectable electronic devices.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the disclosed embodiments but also any other combination of features from different embodiments. Various features mentioned in the different embodiments can be combined with explicit mentioning of such combination or arrangement in an example embodiment. Furthermore, any of the embodiments and features described or depicted herein can be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. A pressure injury prevention system for a patient, the pressure injury prevention system comprising:
   a weight support device configured to support the patient, the weight support device comprising:
      a sensor grid layer including a plurality of sensors configured to measure a time series of pressure data; and
      a plurality of inflation bladders forming an automatically adjustable surface;
   a computer configured to:
      predict a pressure injury outcome based on the time series of pressure data, the pressure injury outcome including at least a prediction of risk of the patient developing a pressure injury, wherein predicting the pressure injury outcome comprises:
         determining a time series of poses of the patient using a first machine learning model trained to receive the time series of the pressure data as input and to output the time series of poses of the patient, the time series of poses comprising a time series of side labels, a time series of joint locations, and movement over time, and
         determining a risk of the patient developing the pressure injury using a second machine learning model trained to receive the time series of poses of the patient determined using the first machine learning model and the time series of pressure data, wherein training samples for training the second machine learning model comprise historical data of individuals who have developed a pressure injury;

determine an instruction to adjust the automatically adjustable surface based on the pressure injury outcome predicted using the first and second machine learning models; and provide the instruction to the weight support device, wherein the plurality of inflation bladders of the weight support device are configured to adjust the automatically adjustable surface responsive to the instruction; and a display configured to present a notification generated based on the pressure injury outcome, the notification indicating that an adjustment of a positioning of the patient is needed.

2. The pressure injury prevention system of claim 1, wherein the weight support device further comprises a second sensor grid layer including a plurality of moisture sensors configured to measure surface moisture data, and wherein the computer is further configured to predict the pressure injury outcome based on the surface moisture data.

3. The pressure injury prevention system of claim 1, wherein the weight support device further comprises a temperature sensor configured to measure surface temperature data, and wherein the computer is further configured to predict the pressure injury outcome based on the surface temperature data.

4. The pressure injury prevention system of claim 1, wherein the weight support device is a first weight support device, and wherein the pressure injury prevention system further comprises:

a second weight support device configured to collect additional pressure data about the patient as the patient moves between the first weight support device and the second weight support device, the pressure data generated by the first and second weight support devices is uploaded to a database, the database stores the pressure data as aggregate data, and wherein the computer is further configured to predict the pressure injury outcome based on the aggregate data.

5. The pressure injury prevention system of claim 4, wherein the first weight support device has a first surface area configured to support the patient in a first posture and the second weight support device has a second surface area configured to support the patient in a second posture.

6. The pressure injury prevention system of claim 4, wherein the first weight support device is a bed and the second weight support device is a wheelchair.

7. The pressure injury prevention system of claim 1, further comprising:

a hand-held sensor configured to measure an amount of moisture under the patient's skin, and wherein determining, using the second machine learning model, the risk of the patient developing the pressure injury comprises determining the risk of the patient developing the pressure injury based on the amount of moisture under the patient's skin.

8. The pressure injury prevention system of claim 1, wherein determining, using the second machine learning model, the risk of the patient developing the pressure injury comprises determining the risk of the patient developing the pressure injury based on a health record of the patient.

9. The pressure injury prevention system of claim 1, wherein the computer is further configured to determine one or more areas of high shear based on the pressure data, and wherein the computer is configured to predict the pressure injury outcome based on the one or more areas of high shear.

10. The pressure injury prevention system of claim 1, wherein the display is further configured to present a visual representation of the pressure data collected by the weight support device, the visual representation displaying an area of the patient at risk of developing the pressure injury.

11. The pressure injury prevention system of claim 1, wherein the pressure injury outcome includes one or more of: an amount of time that indicates when the adjustment of the positioning of the patient is needed and an indication of an area of the patient where the pressure injury is likely to develop.

12. A method comprising:

receiving a time series of pressure data from a weight support device that comprises a sensor grid including a plurality of sensors that generates the pressure data and a plurality of inflation bladders forming an automatically adjustable surface;

predicting, based on the time series of the pressure data, a pressure injury outcome of a patient supported by the weight support device, the pressure injury outcome including at least a prediction of risk of the patient developing a pressure injury, wherein predicting the pressure injury outcome comprises:

determining a time series of poses of the patient using a first machine learning model trained to receive the time series of the pressure data as input and to output the time series of poses of the patient, the time series of poses comprising a time series of side labels, a time series of joint locations, and movement over time, and determining a risk of the patient developing the pressure injury using a second machine learning model trained to receive the time series of poses of the patient determined using the first machine learning model and the time series of pressure data, wherein training samples for training the second machine learning model comprise historical data of individuals who have developed a pressure injury;

determining an instruction to adjust the automatically adjustable surface based on the pressure injury outcome predicted using the first and second machine learning models;

providing the instruction to the weight support device, wherein the plurality of inflation bladders of the weight support device are configured to adjust the automatically adjustable surface responsive to the instruction; and providing, for display, a notification generated based on the pressure injury outcome, the notification indicating that an adjustment of a positioning of the patient is needed.

13. The method of claim 12, further comprising:

receiving surface moisture data from a second sensor grid of the weight support device, the second sensor grid generates the surface moisture data, and wherein predicting the pressure injury outcome is further based on the surface moisture data.

14. The method of claim 12, wherein the weight support device is a first weight support device, and the method further comprising:

receiving additional pressure data from a second weight support device, the additional pressure data including pressure data about the patient as the patient moves between the first weight support device and the second weight support device; and providing the pressure data generated by the first and second weight support devices to a database, the database storing the pressure data as aggregate data, and wherein predicting the pressure injury outcome is further based on the aggregate data.

15. The method of claim 13, further comprising:

receiving information about an amount of moisture under the patient's skin from a hand-held sensor, the hand-held sensor generates the information, and wherein determining, using the second machine learning model, the risk of the patient developing the pressure injury comprises determining the risk of the patient developing the pressure injury based on the amount of moisture under the patient's skin.

16. The method of claim 12, further comprising:

determining one or more areas of high shear based on the pressure data, and determining, using a second machine learning model, a risk of the patient developing the pressure injury comprises determining the risk of the patient developing the pressure injury based on the one or more areas of high shear.

17. The method of claim 12, further comprising:

providing, for display, a visual representation of the pressure data collected by the weight support device, the visual representation indicating an area of the patient at risk of developing the pressure injury.

18. The method of claim 12, wherein the pressure injury outcome includes one or more of: an amount of time indicating when the adjustment of the positioning of the patient is needed and an indication of an area of the patient where the pressure injury is likely to develop.

* * * * *